United States Patent [19]
Rajala et al.

[11] Patent Number: 5,660,657
[45] Date of Patent: Aug. 26, 1997

[54] COMPOSITE METHOD FOR FABRICATING GARMENTS

[75] Inventors: Gregory John Rajala, Neenah; Paul Daniel Suke, Appleton; Steven Craig Gehling, Oshkosh; Gerald Leigh Rabe, Appleton, all of Wis.

[73] Assignee: Kimberly-Clark Worldwide, Inc., Neenah, Wis.

[21] Appl. No.: 381,389

[22] Filed: Jan. 31, 1995

[51] Int. Cl.⁶ ................................... B29C 65/08
[52] U.S. Cl. .............. 156/64; 156/73.2; 156/73.3; 156/164; 156/200; 156/229; 156/253
[58] Field of Search ................ 156/73.1, 73.2, 156/73.3, 160, 163, 164, 229, 252, 253, 268, 290, 494, 495, 515, 516, 522, 580.1, 580.2, 581, 582, 583.1, 196, 199, 200; 83/956, 30, 660

[56] References Cited

U.S. PATENT DOCUMENTS

| | | | |
|---|---|---|---|
| 3,217,957 | 11/1965 | Jarvie | 223/1 |
| 3,242,029 | 3/1966 | Deans | 156/380 |
| 4,081,301 | 3/1978 | Buell | 156/164 |
| 4,227,952 | 10/1980 | Sabee | 156/164 |
| 4,261,782 | 4/1981 | Teed | 156/361 |
| 4,309,236 | 1/1982 | Teed | 156/164 |
| 4,353,762 | 10/1982 | Bouda | 156/164 |
| 4,405,397 | 9/1983 | Teed | 156/164 |
| 4,425,173 | 1/1984 | Frick | 156/204 |
| 4,464,217 | 8/1984 | Dickover et al. | 156/164 |
| 4,479,836 | 10/1984 | Dickover et al. | 156/164 |
| 4,617,082 | 10/1986 | Oshefsky et al. | 156/447 |
| 4,650,530 | 3/1987 | Mahoney et al. | 156/73.1 |
| 4,713,132 | 12/1987 | Abel et al. | 156/73.1 |
| 4,743,241 | 5/1988 | Igaue et al. | 604/385 A |
| 4,889,293 | 12/1989 | Duke et al. | 242/75.51 |
| 4,897,084 | 1/1990 | Ternstrom et al. | 604/385.2 |
| 4,925,520 | 5/1990 | Beaudoin et al. | 156/494 |
| 5,055,103 | 10/1991 | Nomura et al. | 604/385.2 |
| 5,087,320 | 2/1992 | Neuwirth | 156/580.2 |
| 5,091,039 | 2/1992 | Ujimoto | 156/519 |
| 5,092,861 | 3/1992 | Nomura et al. | 604/385.2 |
| 5,110,403 | 5/1992 | Ehlert | 156/580.1 |
| 5,171,239 | 12/1992 | Igaue et al. | 604/385.2 |
| 5,188,627 | 2/1993 | Igaue et al. | 604/385.2 |
| 5,545,275 | 8/1996 | Herrin et al. | 156/73.1 |

FOREIGN PATENT DOCUMENTS

| | | |
|---|---|---|
| 0475419A1 | 3/1992 | European Pat. Off. . |
| 0487921A2 | 6/1992 | European Pat. Off. . |
| 0626161A1 | 11/1994 | European Pat. Off. . |
| 62-280155 | 12/1987 | Japan . |
| 1176766 | 7/1989 | Japan . |
| 4-28364 | 1/1992 | Japan . |
| 4-28363 | 1/1992 | Japan . |
| 2241424 | 9/1991 | United Kingdom . |
| WO9104724 | 4/1991 | WIPO . |

OTHER PUBLICATIONS

An Active Dancer Roll System for Tension Control of Wire And Sheet–Kuribayashi and Nakijima 1984.

*Primary Examiner*—James Sells
*Attorney, Agent, or Firm*—Mark L. Davis; Thomas D. Wilhelm; Brian R. Tumm

[57] ABSTRACT

This invention pertains to methods for use in constructing a garment including a stretched elastic. Specifically, the invention contemplates incorporating stretched elastic into a continuous web, including one or more segments which exert retractive forces in directions counterproductive to the function of either the web, the garment, or both, and nullifying that portion of the stretched elastic which would be counterproductive. The elastics may be cut at appropriate loci. The stretch may be intermittently reduced or eliminated on one or more selected ones of the elastics as the elastics are incorporated into the web. A special coating may be used on the processing rolls to maintain the width dimension of the web at loci disposed after incorporation of elastic stretched across the transverse dimension of the web. Transverse bonds may be formed on the web using a rotary carrying drum, and energy application devices which rotate with the drum, to increase bond forming time.

72 Claims, 44 Drawing Sheets

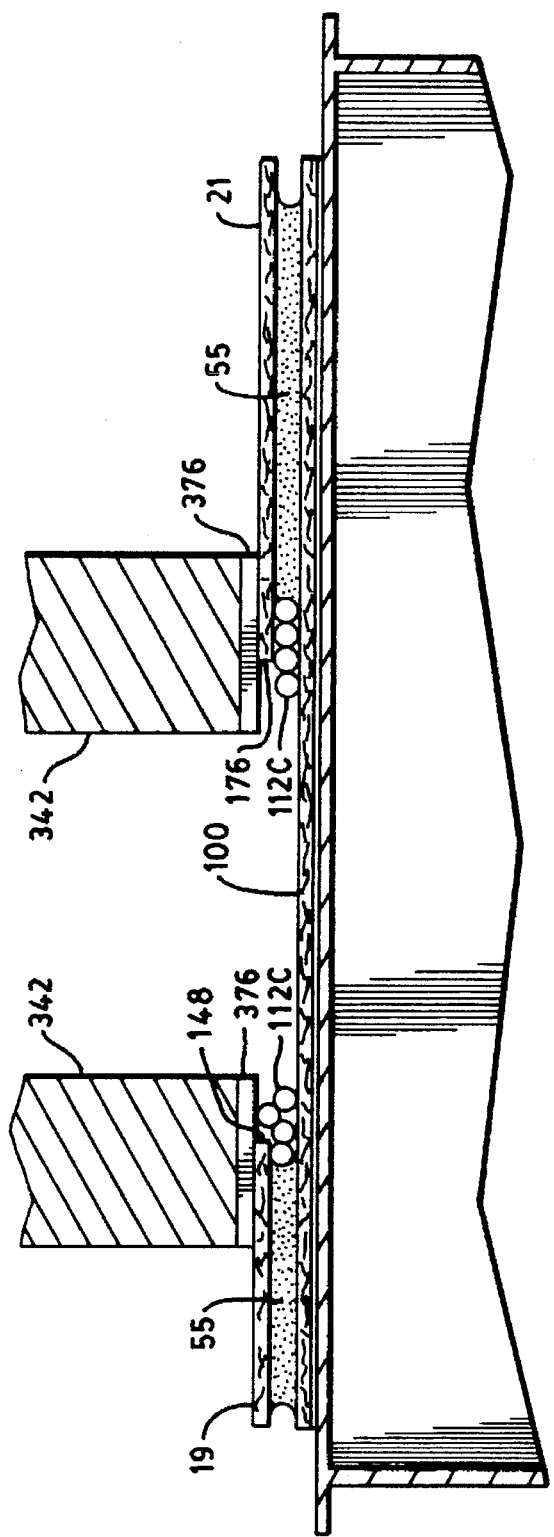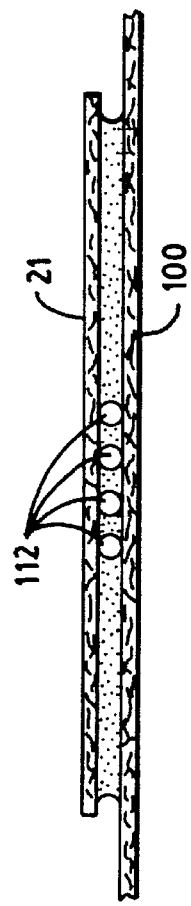

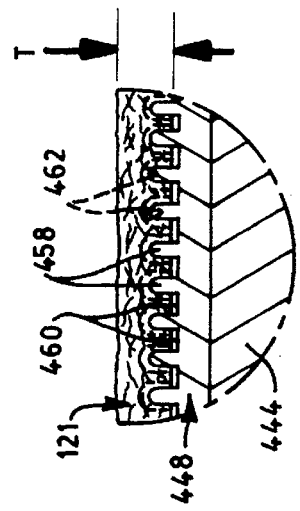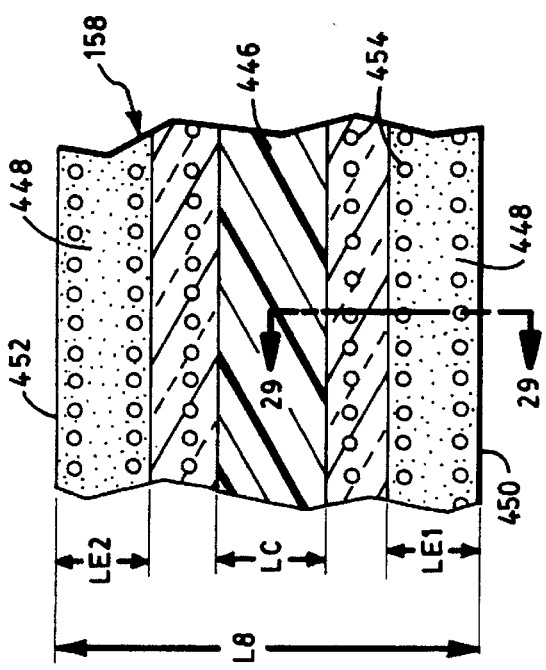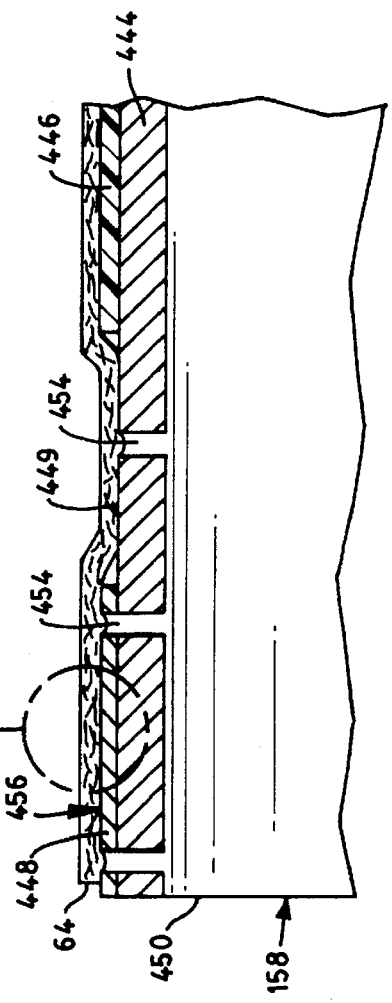

COMPOSITE METHOD FOR FABRICATING GARMENTS

FIELD OF THE INVENTION

This invention relates to methods and apparatus for use in constructing a garment including leg elastics at leg openings. Specifically, this invention contemplates incorporating stretched elastics into a continuous web, including one or more segments of the elastics which exert retractive forces in directions counterproductive to the function of either the web, the garment, or both. The methods and apparatus nullify the counterproductive aspects of the forces exerted by the elastics.

BACKGROUND OF THE INVENTION

In fabricating disposable garments using a continuous web to form discrete garment blanks, and optionally the garments, themselves, it is known to incorporate elastic threads, both stretched and unstretched, into the garment structure, in both the with machine direction and the cross machine direction. When stretched elastic threads are incorporated into the web in the cross machine direction, the elastic threads urge retractive forces on the web in the cross machine direction, tending to reduce the width of the web.

In addition, to the extent the elastic extends across the crotch portion of the garment being fabricated, the cross-crotch elastics urge a bunching up of the material extending across the crotch, whereby the crotch portion of the garment will not lie flat against the body of the user.

Further, to the extent portions of the workpieces are to be bonded to each other with bonds extending in the cross machine direction, it is desirable to have substantial dwell time at the bonding station in the apparatus, in order to effect fabrication of the requisite bonds.

Thus it is an object of this invention to provide methods and apparatus for relieving and/or otherwise nullifying the retractive effect of elastics incorporated in the web in the cross machine direction.

It is a further object to provide methods and apparatus for severing the cross crotch elastics.

It is still a further object to provide apparatus for relieving the stretch in the elastics as the elastics feed into the web at the locus that forms the crotch of each workpiece, and for exerting a stretched condition on the elastics as the elastics feed into the web at loci not forming the crotch of the respective workpieces.

It is another object to provide methods and apparatus for treating cross crotch elastics in order to avoid having the cross crotch elastics causing the crotch to bunch up on the user.

Still another object is to provide method and apparatus for placing crotch elastics on each workpiece to extend in a transverse direction across the web, such that opposing portions of the crotch elastics extend to, and coact with, front and back leg elastics in the garment.

Another object is to use friction surface such as obtained with plasma coatings on processing rolls, optionally with suction on the rolls, to stabilize the width dimension of the web after incorporating stretched elastics into the web in a direction transverse to the with machine direction.

It is yet another object to provide bonding apparatus and methods which provide for fabricating bonds in a direction transverse to the with machine direction, and to give substantially more dwell time for forming the bonds than applies as a workpiece passes a planar-type bonding apparatus, such as a plunge bonder.

Yet another object is to form such transverse bonds using a rotary carrying drum and energy application devices, preferably to apply ultrasonic energy to so form the bonds.

Summary of the Disclosure

This invention describes methods and apparatus for use in constructing a garment including leg elastics at leg openings, using a continuous web as a base substrate. Specifically, the invention describes incorporating leg elastics in a continuous process wherein stretched elastics are incorporated into the continuous web, including across the crotch, but wherein the elastics exert little if any substantially reduced retractive forces across the crotch in the finished garment or the respective garment blank. Further, the stretched elastics extend in a transverse direction across the width dimension of the continuous web. The apparatus and methods of the invention are adapted to control shrinkage of the web in the width dimension to less than 5% shrinkage, in spite of the transverse direction retractive forces exerted by the transversely oriented stretched elastics.

In a first family of embodiments, the invention comprehends a method for use in constructing, in a processing system, a garment including leg elastics at leg openings, the method comprising fabricating a garment blank, as one of a series of consecutive workpieces in a continuous web, the workpieces comprising cutout portions corresponding to the leg openings in the garment blanks, each leg opening having a front portion corresponding with a front body portion of the garment blank, a back portion corresponding with a back body portion of the garment blank, and a crotch portion, each workpiece and corresponding garment blank having first and second leg openings and a crotch between the respective leg openings. The method includes, with respect to respective blanks, the steps of stretching first leg elastics, and incorporating the first leg elastics into the continuous web along the front portion of the first leg opening, across the crotch, and along the front portion of the second leg opening, in stretched condition; stretching second leg elastics, and incorporating the second leg elastics into the continuous web along the back portion of the first leg opening, across the crotch, and along the back portion of the second leg opening, in stretched condition, the second leg elastics being separate from the first leg elastics; and subsequently relieving stretch, preferably substantially all the stretch, in the first and second leg elastics across the crotch while maintaining the stretch, preferably substantially all the stretch, in the first and second leg elastics along the respective front and back portions of the first and second leg openings.

In some embodiments, the relieving of stretch in the first and second leg elastics across the crotch comprises severing at least one of the strands of the first and second leg elastics at the crotch without effecting corresponding severing of the continuous web, for example, by applying ultrasonic energy to the outer surface of the workpiece at at least one selected locus in the crotch, sufficient to effect severing of the strands of elastics without corresponding cutting of the continuous web. Where the first and second leg elastics comprise elements of elastic disposed on the interior of the workpiece, the method may include severing the at least one strand of the first and second leg elastics by applying ultrasonic energy to the outer surface of the workpiece at selected loci in the crotch over the first and second leg elastics, sufficient to effect severing of at least one of the threads of elastic on the interior of the workpiece without corresponding severing of the continuous web.

In other embodiments, the relieving of stretch in the first and second leg elastics across the crotch comprises using a dancer roll to control tension on the first and second leg elastics as the first and second leg elastics are incorporated into the continuous web, including applying an active force to the dancer roll, effecting active movement of the dancer roll for each workpiece entering into the processing system, and preferably substantially releasing the force applied, in cycles, each cycle thus causing movement of the dancer roll and corresponding substantially relieving of tension in the first and second leg elastics as the first and second leg elastics are incorporated into the web at the crotch of the corresponding workpiece, and imposing tension as the first and second leg elastics are incorporated into the web along the respective front and back portions of the leg openings.

The velocity of the dancer roll is preferably effected with a prime mover, and the method includes measuring a first velocity of the web after the dancer roll, measuring a second velocity of the web at the dancer roll, measuring velocity of the dancer roll, sensing the position of the dancer roll, measuring web tension before the dancer roll, measuring web tension after the dancer roll, and controlling the prime mover with a computer controller providing control commands to the prime mover based on the sensed position and the measured tensions and velocities, and thereby controlling the active force imparted to the dancer roll by the prime mover.

The method may further include stretching third leg elastics, orienting the third leg elastics in a direction transverse to the longitudinal dimension of the web, and incorporating the transverse, stretched third leg elastics along opposing edges of the crotch, with opposing ends of the third leg elastic being disposed adjacent respective ones of the first and second leg elastics.

With respect to handling the web, the method may include incorporating the first and second leg elastics into the continuous web on a first rotary transport device (e.g. a first processing roll) having a first outer working surface including a first set of protuberances thereon, interacting with the web and thereby inhibiting shrinkage of the web in the width dimension on the first rotary transport device, transferring the web from the first rotary transport device to a second outer working surface of a second rotary transport device (e.g. a second processing roll), the first and second outer working surfaces being aligned with each other at the locus of closest approach of the first and second outer working surfaces, the second outer working surface including a second set of protuberances thereon, the second set of protuberances being aligned with the first set of protuberances along the direction of advance of the web, and interacting with the web and thereby inhibiting shrinkage of the web in the width dimension on the second rotary transport device.

Preferably, the method includes aligning the first and second outer working surfaces at their loci of closest approach to each other, across the entire width of the web, and maintaining such alignment while transferring the web from the first rotary transport device to the second rotary transport device, and may include applying suction to the web at at least one of the first and second outer working surfaces, to assist in inhibiting shrinkage of the web in the width dimension.

At least one of the first and second rotary transport devices preferably comprises a substrate including a support for the respective outer working surface, and a coating on the substrate, incorporating the respective set of protuberances, and a release agent (e.g. polytetrafluoroethylene) in the composition of the coating.

The above described method of handling the web is typically effective to retain the width of the web dimensionally stable such that shrinkage in the width dimension, between first and second edges of the web, is no more than about 5%, usually substantially less, such as no more than about 0.5%.

In preferred embodiments, the workpiece is disposed in a transverse orientation in the web, with the front and back body portions on opposing sides of the web, the method further including folding the web such that the front and back body portions of the respective workpieces are facing each other, and forming side seam bonds joining the front and back body portions to each other in the web, and thereby effectively joining the respective first and second leg elastics at the side seam bonds, to thereby provide effective continuity of stretching capacity at the respective leg openings between the third leg elastics and respective ones of the first and second leg elastics. Preferably, the method includes simultaneously forming the side seam bonds, joining the front body portion to the back body portion, in adjoining ones of the workpieces in the continuous web.

The forming of the side seam bonds preferably includes the steps of rotating a drum about a first axis in a given direction, the drum having a third, and circumferential outer working surface, a first energy application device mounted on the drum adjacent the third outer working surface and extending transverse to the direction of rotation of the drum; providing a second energy application device, mounted for rotation with the drum; moving the second energy application device in a direction transverse to the direction of rotation of the drum and thereby extending the second energy application device over the first energy application device and operating the first and second energy application devices in combination and thereby applying energy to the workpiece during rotation of the drum; and withdrawing the second energy application device from over the first energy application device during rotation of the drum.

In preferred applications of this method, an ultrasonic horn is used as one of the energy application devices, and an anvil adapted to cooperate with the ultrasonic horn is used as the other energy application device.

The method may include, after forming the side seam bonds, severing the respective workpiece from the web, optionally as a garment.

The method preferably includes the steps of traversing the second energy application device along an energy application path over the first energy application device, the first energy application device comprising an anvil, the second energy application device comprising a wheel mounted for rotation about a second axis, the method comprising applying energy to the workpiece, preferably ultrasonic energy, through either the first or the second energy application device, at a locus of points moving progressively across the workpiece as the wheel traverses the energy application path. The locus of points may consist of a point, a series of points, a line or a series of lines.

In a second family of embodiments, the invention comprehends a processing system for use in constructing a garment, including a garment blank precursor, as one of a series of consecutive workpieces in a continuous web, the garment and garment blank having leg elastics at leg openings, the workpieces comprising cutout portions corresponding to the leg openings in the garment blanks, each leg opening having a front portion corresponding with a front body portion of the garment blank, a back portion corresponding with a back body portion of the garment blank, and a crotch portion, each workpiece and corresponding garment blank having first and second leg openings and a crotch between the respective leg openings. The apparatus thus comprises apparatus for stretching first leg elastics, and apparatus for incorporating the first leg elastics into the continuous web along the front portion of the first leg opening, across the crotch, and along the front portion of the second leg opening, in stretched condition; apparatus for stretching second leg elastics, and apparatus for incorporating the second leg elastics into the continuous web along the back portion of the first leg opening, across the crotch, and along the back portion of the second leg opening, in stretched condition, the second leg elastics being separate from the first leg elastics; and apparatus for subsequently relieving stretch, preferably substantially all the stretch, in the first and second leg elastics across the crotch while maintaining the stretch in the first and second leg elastics along the respective front and back portions of the first and second leg openings.

In some embodiments, the apparatus for relieving stretch in the first and second leg elastics across the crotch comprises apparatus for severing the first and second leg elastics at the crotch without effecting corresponding severing of the continuous web, for example, apparatus for applying ultrasonic energy to the outer surface of the workpiece at at least one selected locus in the crotch, sufficient to effect the cutting of the elastics without corresponding cutting of the continuous web.

In other embodiments, the apparatus for relieving stretch in the first and second leg elastics across the crotch comprises a dancer roll adapted to control tension on the first and second leg elastics as the first and second leg elastics are incorporated into the continuous web, including apparatus for applying an active force to the dancer roll, to effect active movement of the dancer roll for each workpiece entering into the processing system, and preferably apparatus for releasing the force applied, in cycles, each cycle thus causing movement of the dancer roll and correspondingly relieving of tension in the first and second leg elastics as the first and second leg elastics are incorporated into the web at the crotch of the corresponding workpiece, and imposing tension as the first and second leg elastics are incorporated into the web along the respective front and back portions of the leg openings.

Preferably, the processing system includes a prime mover for effecting the velocity of the dancer roll, apparatus for measuring a first velocity of the web after the dancer roll, apparatus for measuring a second velocity of the web at the dancer roll, apparatus for measuring velocity of the dancer roll, apparatus for sensing the position of the dancer roll, apparatus for measuring web tension before the dancer roll, apparatus for measuring web tension after the dancer roll, and apparatus for controlling the prime mover with a computer controller providing control commands to the prime mover based on the sensed position and the measured tensions and velocities, and thereby controlling the active force imparted to the dancer roll by the prime mover.

In preferred embodiments, the processing system includes means for stretching third leg elastics, apparatus for orienting the third leg elastics in a direction transverse to the longitudinal dimension of the web, and apparatus for incorporating the transverse, stretched third leg elastics along opposing edges of the crotch, such that opposing portions of the third leg elastic are disposed adjacent respective ones of the first and second leg elastics.

The processing system preferably includes novel apparatus for handling the web where the web has a width dimension, the processing system including apparatus for incorporating the first and second leg elastics into the continuous web on a first rotary transport device, the first rotary transport device having a first outer working surface including a first set of protuberances thereon, adapted for interacting with the web and thereby inhibiting shrinkage of the web in the width dimension on the first rotary transport device, a second rotary transport device having a second outer working surface, the first and second outer working surfaces being aligned with each other at the locus of closest approach of the first and second outer working surfaces such that the web can be transferred from the first rotary transport device to the second rotary transport device, the second outer working surface including a second set of protuberances thereon, the second set of protuberances being aligned with the first set of protuberances along the direction of advance of the web, and being adapted for interacting with the web and thereby inhibiting shrinkage of the web in the width dimension on the second rotary transport device.

Preferably, the first and second outer working surfaces are aligned at the locus of closest approach of the first and second outer working surfaces to each other, across the entire width of the web, and are maintained in alignment while transferring the web from the first rotary transport device to the second rotary transport device The processing system may include apparatus for applying suction to the web at at least one of the first and second outer working surfaces, to assist in inhibiting shrinkage of the web in the width dimension.

At least one of the first and second rotary transport devices preferably comprises a substrate comprising a support for the first outer working surface, and a coating on the substrate, incorporating the first set of protuberances, and a release agent in the composition of the coating.

The processing system preferably includes apparatus for folding the web, wherein the workpiece is disposed in a transverse orientation in the web, with the front and back body portions on opposing sides of the web, such that the front and back body portions of the respective workpieces are facing each other, and apparatus for forming side seam bonds joining the front body portion to the back body portion in the web, and thereby effectively joining the respective first and second leg elastics at the side seam bonds, to thereby provide effective continuity of stretching capacity at the respective leg openings between the third leg elastics and respective ones of the first and second leg elastics. Preferably, the processing system includes apparatus for simultaneously forming the side seam bonds, joining the front body portion to the back body portion, in adjoining ones of the workpieces in the continuous web.

In the processing system, the first rotary transport device may comprise a drum mounted for rotation about a first axis in a given direction, the drum having a third circumferential outer working surface, a first energy application device mounted on the drum adjacent the third outer working surface and extending transverse to the direction of rotation of the drum; a second energy application device, mounted for rotation with the drum, and adapted to move in a direction transverse to the direction of rotation of the drum and thereby to extend the second energy application device over the first energy application device, and apparatus for operating the first and second energy application devices in combination, thereby to apply energy to the workpiece during rotation of the drum; and apparatus for withdrawing the second energy application device from over the first energy application device during rotation of the drum.

In preferred embodiments, one of the energy application devices is an ultrasonic horn, and the other is an anvil adapted to cooperate with the ultrasonic horn.

The processing system may include apparatus for severing the respective workpiece from the web after the forming of the side seam bonds, thereby to provide a garment.

The processing system preferably includes apparatus for causing the second energy application device to traverse along an energy application path over the first energy application device, the first energy application device comprising an anvil, the second energy application device comprising a wheel mounted for rotation bout a second axis, the processing system further comprising apparatus for applying energy to the workpiece, preferably ultrasonic energy, through either the first or the second energy application device, at a locus moving progressively across the workpiece as the wheel traverses the energy application path.

BRIEF DESCRIPTION OF THE DRAWINGS

The present invention will be more fully understood and further advantages will become apparent when reference is made to the following detailed description of the invention and the drawings, in which:

FIG. 21 is a fragmentary cross-section of the web taken at 21—21 of FIG. 20.

FIG. 22 is a cross-section of the web, and corresponding ultrasonic horn and anvil, taken at 22—22 of FIG. 8.

FIG. 28 is a top view of a fragment of one of the processing rolls, taken at 28—28 of FIG. 13.

FIG. 29 is a fragmentary cross-section of a process roll, showing a representative coating applied to rolls of the invention, and incorporating protuberances therein, taken at 29—29 of FIG. 28.

FIG. 30 is an enlarged cross-section of a portion of the roll of FIG. 29, taken at the broken circle 30 in FIG. 29.

DETAILED DESCRIPTION OF THE ILLUSTRATED EMBODIMENTS

The following detailed description is made in the context of an article including a disposable garment, and corresponding garment blanks and blank pre-forms, for holding a sanitary pad in place as a primary absorbent during use of the garment. It is readily apparent, however, that the present invention can be employed with other disposable sanitary articles, such as feminine tampons, incontinent pads and other products and the like.

Figure 1:
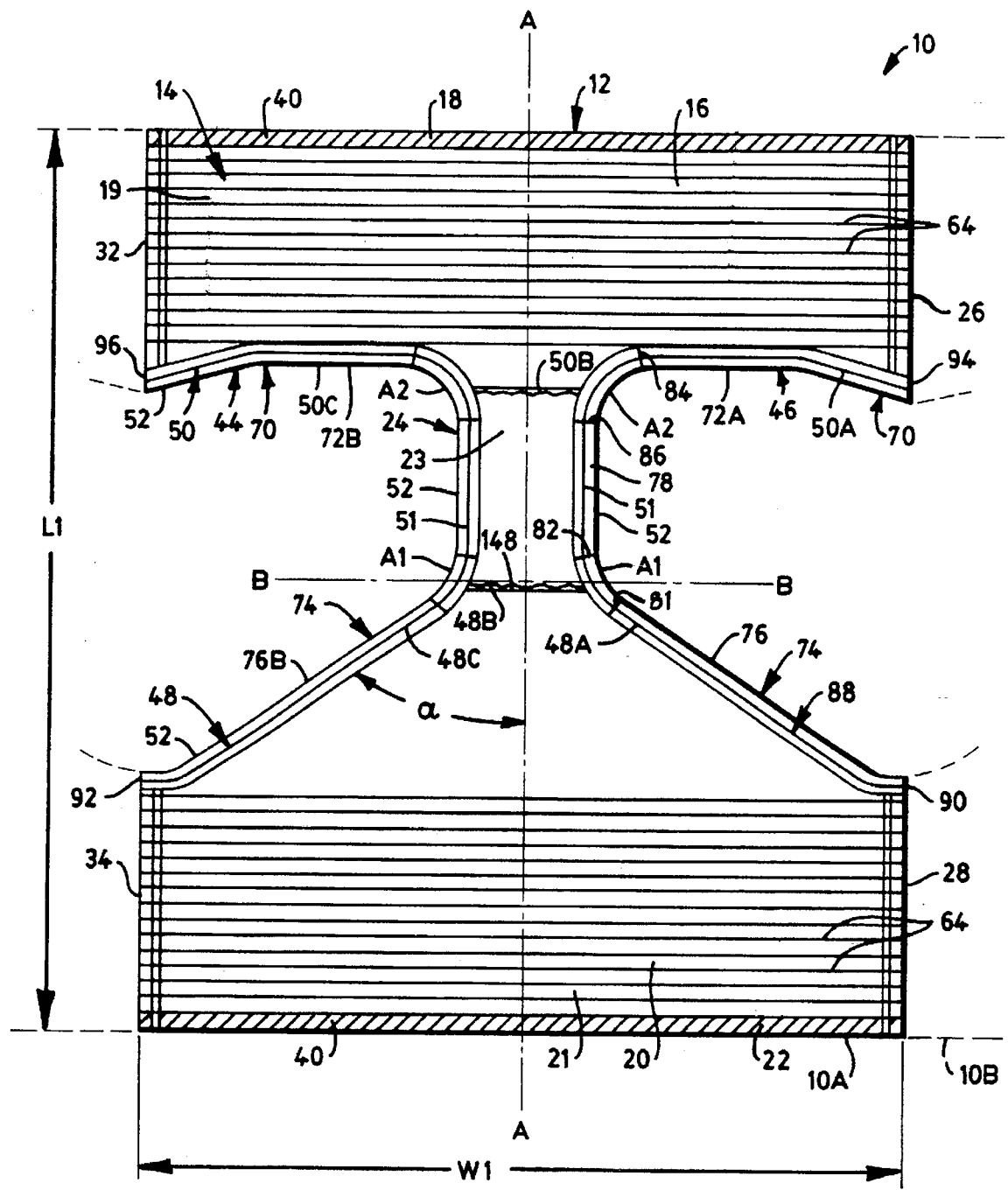
FIG. 1 is a plan view of a garment blank relating to a panty of the invention.
Figure 2:
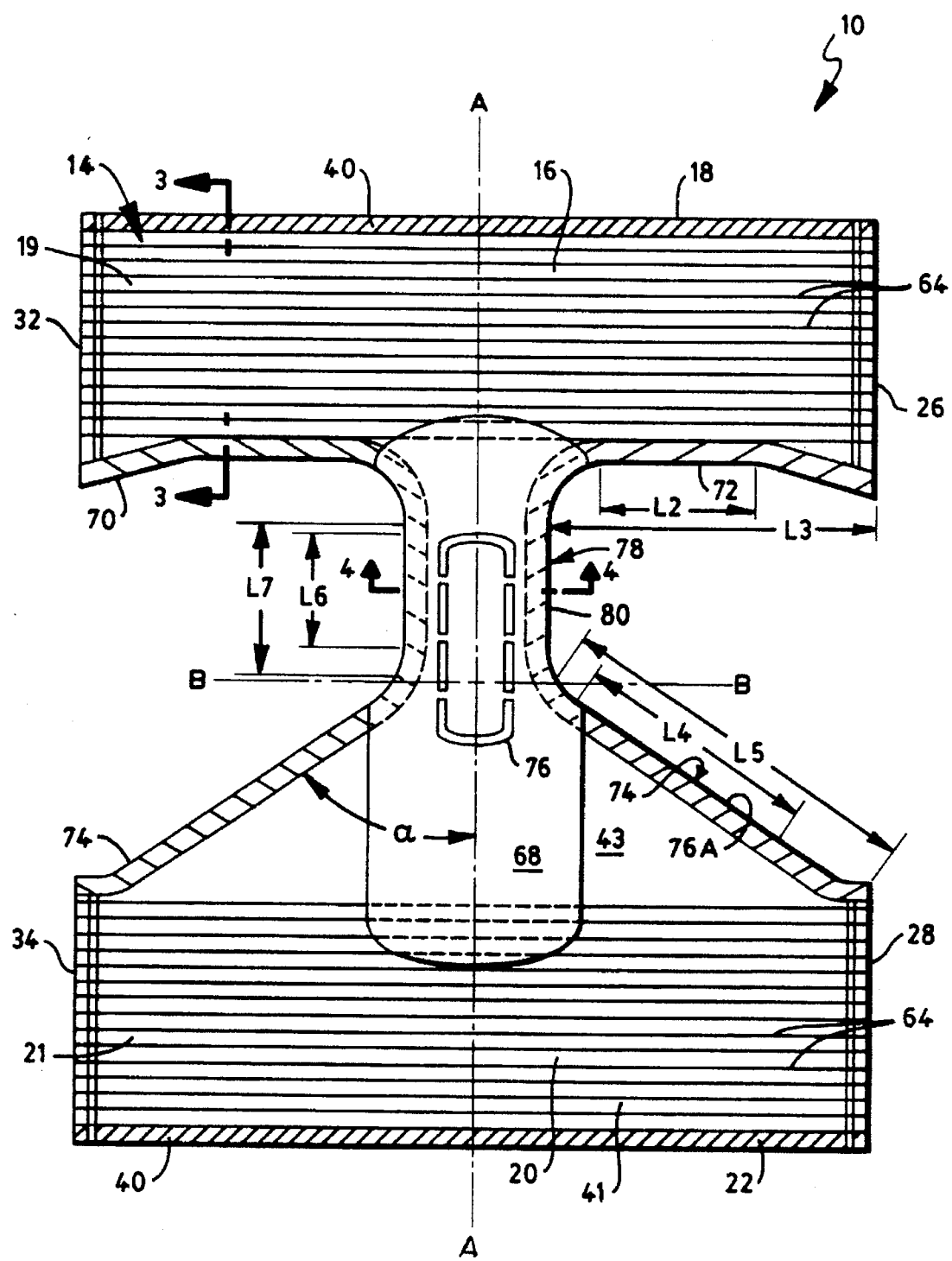
FIG. 2 is a plan view of the garment blank of FIG. 1, including a secondary absorbent in the crotch.
Figure 5:
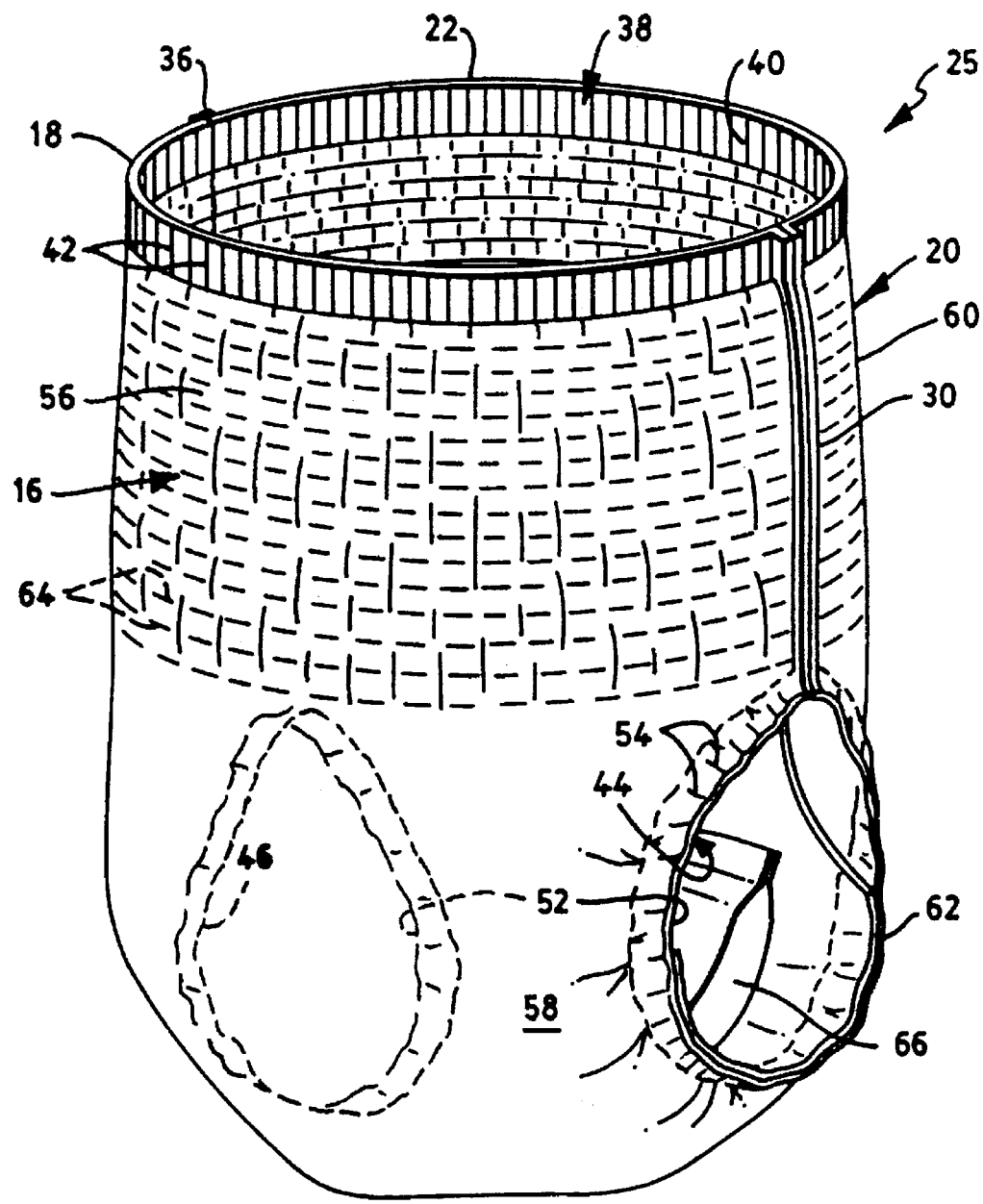
FIG. 5 is a perspective view of a disposable garment of the invention.

The garment blank 10 of FIG. 1 illustrates the preferred embodiment of the two-layer garment blank prior to incorporation of the secondary absorbent. The garment blank of FIG. 2 illustrates the preferred embodiment of the finished garment blank including all elements, but before the final steps of assembling the composite to form the garment structure. FIG. 5 shows the finally-assembled disposable garment structure.

Figure 3:
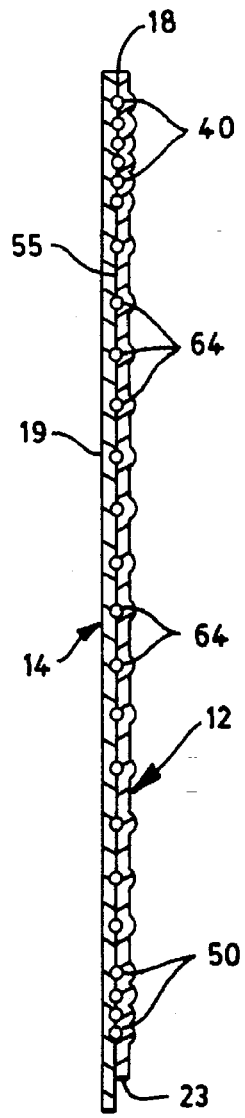
FIG. 3 is a cross section of the garment blank taken at 3—3 of FIG. 2.

Referring to FIGS. 1–3, the garment blank 10 has an outer cover layer 12 generally defining the overall garment length "L1" and garment width "W1" of the blank, and a body side layer 14 secured to the outer cover layer. The garment blank 10 generally includes a front body portion 16 terminating at a front waist portion 18 as a first edge of the blank, a back body portion 20 terminating at a back waist portion 22 as a second edge of the blank, and a crotch 24.

The body side layer 14 includes a front layer element 19 generally overlying and secured to the outer cover layer 12 on the front body portion 16, and a back layer element 21 generally overlying and secured to the outer cover layer 12 on the back body portion 20. A space 23, shown in FIG. 1, separates the front layer element 19 from the back layer element 21.

Referring to FIGS. 2 and 5, for assembling the blank of FIG. 2 to form a garment 25 as in FIG. 5, a first side edge 26 of front body portion 16 is assembled with a corresponding first side edge 28 of the back body portion 20 to form a first side seam 30. Similarly, a second side edge 32 of the front body portion 16 is assembled with a second side edge 34 of the back body portion 20 to form a second side seam 36. The waist portions 18, 22 when assembled, form a waist opening 38 for putting on and taking off the garment 25. The waist opening 38 is surrounded at least in part by a waist elastic 40. The waist elastic 40 is stretched, and incorporated into the waist portions 18, 22, in the stretched state. The waist elastic 40 is released after being secured in the waist, thereby producing waist folds or pleats 42 to allow expansion of the waist opening 38 so that the garment 25 can fit various sizes of people. Because users of this invention generally prefer a brief style garment, the front waist portion 18 preferably comes as high as the navel and is level around the wearer's waist. Having the garment at this height provides a snug fit. Alternative garment styles include bikini (e.g. regular leg cut or french leg cut) and hipster (e.g. regular leg cut or french leg cut).

Figure 4:
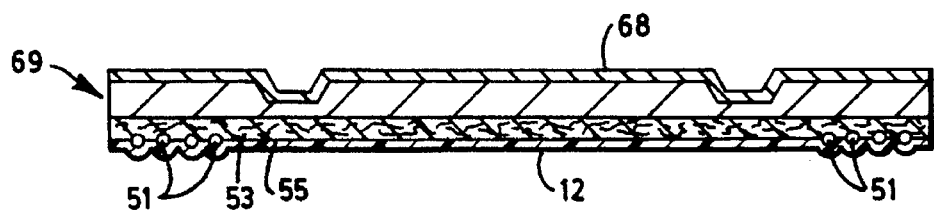
FIG. 4 is a cross section of the garment blank taken at 4—4 of FIG. 2.

Referring to FIGS. 1 and 5, the front body portion 16, the back body portion 20, and the crotch 24, in combination, form left and right leg openings 44 and 46, respectively, in the finally assembled garment 25. The leg openings 44, 46 are formed by cutting away portions of the outer cover layer 12, and corresponding portions, if any, of body side layer 14, as will be discussed briefly hereinafter. Each leg opening 44, 46 is surrounded at least in part by a back leg elastic 48, a front leg elastic 50, and a crotch elastic 51 between the back leg elastic and the front leg elastic. Each of the respective elastics 48, 50, 51 is adjacent the respective one of the edges 52 of the corresponding leg openings. The front and back leg elastics 48, 50 are generally secured between the outer cover layer 12 and the body side layer 14 by adhesive 55. The crotch elastics 51 are secured between outer cover layer 12 and a crotch elastic support sheet 53, also by adhesive 55 (shown in FIG. 3). The elastics 48, 50, 51 are in the stretched state when secured to the outer cover layer 12. Accordingly, when the elastics, the outer cover layer, the body side layer, and the support sheet 53 (shown in FIG. 4), are released after the elastics are secured to the outer cover layer, the elastics produce folds 54 at the edges of the leg openings 44, 46 to allow expansion of the leg openings 44, 46 to fit various sizes of legs.

The front body portion 16 may be divided into a front upper portion 56 and a front lower portion 58. Similarly, the back body portion 20 may be divided into a back upper portion 60 and a back lower portion 62. The upper portions 56 and 60 are preferably designed to include body elastics 64 which readily stretch to allow the wearer to put on the garment 25 and then readily contract toward a rest/release state of the body elastics. This ensures a close or snug fit to different body sizes and forms. A number of elements of body elastics 64 are positioned on both the front and the back upper portions 56, 60, respectively, at positions between the waist opening 38 and the leg openings 44, 46, so that the garment 25 has a good fit, particularly around the body of the wearer.

The lower body portions 58, 62 generally do not require the spaced elastics as in the upper body portions 56, 60, although the elastic may be used.

The width of the crotch 24 between the left and right crotch elastics 51 should be wide enough to accommodate laying the primary absorbent 66 between the edges 52 of the leg openings at crotch 24 without having the primary absorbent 66 obstruct the crotch elastics 51. This allows the crotch elastics 51 to contract and draw up the sides of the crotch about the primary absorbent, to thus accommodate the thickness of the primary absorbent 66, and to give surface area within the crotch 24 of the garment, adjacent edges 52, to contain leakage, of e.g. menses, from the primary absorbent 66.

The width of the crotch 24 between the elastics 51 should not be so wide as to seem bulky or uncomfortable. A suitable width is at least about 2.75 inches (70 mm) between the crotch elastics. Width of crotch 24 is advantageously from about 3 inches (76 mm) to about 3.5 inches (89 mm). Preferably, the width is about 3 inches (76 mm).

Preferably, each crotch elastic 51 at the opposing leg openings 44, 46 comprises a number of elements of elastic, acting in combination to perform the crotch elastic function. Each crotch elastic 51 preferably has an effective width of from about 0.375 inch (10 mm) to about 0.625 inch (16 mm). More preferably, the effective width of each crotch elastic is about 0.5 inch (13 mm). Preferably, ruffle material on the edge of the leg openings 44, 46 outside the leg and crotch elastics 48, 50, 51 is less than about 0.25 (6 mm). More preferably, the ruffle material is less than about 0.125 inch (3 mm). It is most desirable to eliminate any ruffle material from the edges of the leg openings 44, 46.

The overall width of the crotch 24 includes the width between the left and right crotch elastics 51, the width of the crotch elastics, and any ruffle material outside the crotch elastics to the edges 52 of the leg openings. Preferably, the overall width of the crotch 24 should be at least about 4 inches (102 mm).

FIG. 2 shows the garment blank 10 of FIG. 1 with a secondary absorbent 68 secured in the crotch 24, over the outer cover layer 12 and over parts of the front and back layer elements 19, 21 of the body side layer 14. The width of the secondary absorbent 68 is generally sized in relation to the width of the crotch 24. Preferably, the width of the secondary absorbent 68 is at least as great as the distance between the crotch elastics 51. More preferably, the width of the secondary absorbent is equivalent to the overall width of the crotch 24.

The secondary absorbent 68 should have sufficient capacity to absorb any flow or seepage of body fluid around or through the primary absorbent 66. The secondary absorbent 68 should preferably have a capacity and thickness substantially less than that of the primary absorbent 66, thus providing a nonbulky and flexible fit. The secondary absorbent 68 should have a total liquid-holding capacity of about one-half the capacity of the primary absorbent 66. Preferably, the secondary absorbent 68 should have a total liquid-holding capacity of at least about 3 grams and not more than about 6 grams. More preferably, the total capacity of the secondary absorbent 68 should be from about 4 grams to about 6 grams. However, the basis weight of, or the type of, the secondary absorbent 68 should be selected to provide resistance to flexibility of less than around 400 grams, as measured by INDA Standard Test method IST 90.3-92 Standard Test Method for Handle-O-Meter Stiffness of Nonwoven Fabrics.

The secondary absorbent has a low stiffness. The low stiffness allows the absorbent and its corresponding barrier layer 69 (shown in FIG. 4) to remain attached to the conformable outer cover layer 12 and to the body side layer 14, which together, conform to a substantial range of body sizes and shapes. Preferably, the secondary absorbent has a stiffness of less than 400 grams along any axis tested, more preferably less than 300 grams along any axis and less than 100 grams along the axis parallel to the waist opening. The secondary absorbent alone should have a stiffness of less than 250 grams and preferably less than 100 grams along any axis and more preferably less than 75 grams along the axis parallel to the waist opening.

The overall length of the secondary absorbent 68 should be adequate to extend beyond the ends of the primary absorbent 66, in order to be properly positioned to receive liquid which flows or seeps around the edges of the primary absorbent 66. This overall length is typically at least about 15 inches (382 mm) thus extending beyond the crotch 24 along the longitudinal centerline A—A of the blank 10. The length should generally be in the range of about 15 inches (382 mm) to about 19 inches (484 mm). Preferably, the length of the secondary absorbent 68 is about 17 inches (433 mm).

The width of the secondary absorbent 68 beyond the crotch 24 should be at least as wide as the width of the crotch 24. The width of the secondary absorbent 68 may be narrowed beyond the crotch 24 but may thus compromise the containment of liquid flowing or seeping from the primary absorbent. More preferably, the width outside the crotch is wider than in the crotch, and is from about 5 inches (127 mm) to about 12 inches (306 mm), alternatively from about 5.5 inches (140 mm) to about 7.5 inches (191 mm). Most preferably, the width is about 6.5 inches (165 mm).

Referring to FIGS. 1, 2, 3, and 4, the waist elastics 40, the body elastics 64, and the leg elastics 48, 50, 51 are generally covered by the front and back layer elements 19, 21 of the body side layer 14.

Both outer cover layer 12 and body side layer 14 are compliant and soft feeling to the wearer. The following description of materials from which the outer cover layer 12 can be made applies equally to the material of the body side layer 14.

The outer cover layer 12 may be liquid previous, permitting liquids to readily penetrate into its thickness, or impervious, resistant to the penetration of liquids into its thickness. Outer cover layer 12 may be made from a wide range of materials, such as natural fibers (e.g. wood or cotton fibers), synthetic fibers (e.g. polyester or polypropylene fibers) or from a combination of natural and synthetic fibers or reticulated foams and apertured plastic films. The outer cover layer 12 may be woven, nonwoven such as spunbonded, carded, extruded, or the like. A suitable outer cover layer 12 is carded, and thermally bonded by means well known to those skilled in the fabric art. Alternatively, the outer cover layer 12 is derived from a spunbonded web, preferably a generally continuous web. In preferred embodiments, the outer cover layer is spunbonded polypropylene nonwoven with a wireweave bond pattern having a grab tensile of 19 pounds as measured by ASTM D1682 and D-1776, a Taber 40 cycle abrasion rating of 3.0 as measured by ASTM D-1175 and Handle-O-Meter MD value of 6.6 grams and CD value of 4.4 grams using TAPPI method T-402. Such spunbonded material is available from Kimberly-Clark Corporation, Roswell, Ga. The outer cover layer 12 has a weight of from about 0.3 oz. per square yard (osy) to about 2.0 osy, preferably about 0.7 osy.

The position and shape of the leg openings 44, 46 are important to avoid tightness in the crotch and groin area of the wearer, to obtain adequate buttocks coverage, and to prevent the garment 25 from tilting forward, e.g. tilting such that the front waist edge dips lower in relationship to the back waist edge. FIGS. 1 and 2 illustrate the most preferred design for leg fit and buttocks coverage. The shape of the curve across the top of the leg is important. If the curve is too deep, the garment 25 will shift downward and backward resulting in a short front waist, increased back length and bagginess in the seat of the garment. This would cause the garment 25 to appear tilted when worn as evidenced by an unevenness around the waist of the wearer.

Thus, the majority of the edge 70 of the front portion of each leg opening 44, 46 is defined by a straight section 72 having a length "L2" at least about 70% of the length "L3" of the entire edge 70. The straight section 72 should form an angle with the centerline A—A of between about 75° and about 100°, and most preferably about 90°.

With the garment blank 10 laid out flat as in FIG. 1, the majority of the edge 74 of the back portion of each leg opening is defined by a straight section 76 having a length "L4" at least about 70% of the length "L5" of the entire edge 74. The straight section 76 forms an acute angle with the longitudinal centerline A—A of the blank 10. Preferably, the straight section 76 of the edge 74 forms an acute angle $\alpha$ with the centerline A—A of the garment 25 of between about 50° and 65° and most preferably about 60°.

The majority of the edge 78 of the crotch of each leg opening 44, 46 is defined by a straight section 80 having a length "L6." Preferably, the straight sections 80 are straight for at least about 70% of the entire lengths "L7" of the respective edges 78.

Each back leg edge portion 74 includes an arcuate section "A1" extending from one end 81 of the respective straight section 76 to a second end 82 connecting the respective back leg edge portion 74 to the respective back end of edge 78 of the crotch.

Each front leg edge portion 70 includes an arcuate section "A2" extending from one end 84 of the respective straight section 72 to a second end 86 connecting the respective front leg edge portion 70 to the front end of respective edge 78 of the crotch.

The shape of the arcuate section "A2" at the inner groin area is important. If the arc is too shallow, tightness may be experienced at the inner groin area.

The preferred narrow crotch width reduces coverage of the buttocks. To compensate for such reduction, the arcuate section "A1" is preferably adjusted toward back waist portion 22, such that the end 82 of the arcuate section "A1" should be positioned somewhat forward of centerline B—B as shown in FIGS. 1 and 2.

The waist, back leg, front leg and body elastics 40, 48, 50, 64 respectively are attached to the garment blank 10, generally between the outer cover layer 12 and the body side layer 14, using apparatus and processes described hereinafter.

Materials suitable for use as the elastics include a wide variety, but not limited to, of elastic threads, yarn rubber, flat rubber (e.g. as bands), elastic tape, film-type rubber, polyurethane, and, tape-like elastomer, or foam polyurethane or formed elastic scrim. Each elastic may be unitary, multipart, or composite in construction. The elastomerics used in the elastics may be latent and nonlatent.

The composite width of waist elastic 40 is typically about 0.5 inch (13 mm). The elastic may comprise threads, ribbons, a film, or composite. Threads or ribbons, where used, may be multiple and may be applied as a composite. Preferably, the waist elastic is threads, more preferably four threads are used as the waist elastic and the threads are spaced about 0.17 inch (4.3 mm) apart. The threads may be made of any suitable elastomeric material. One suitable material is spandex such as Lycra® threads available from Dupont in Wilmington, Del. Suitable waist elastics include threads having a total decitex (g/1000 m) of about 3760 for 0.5 inch (13 mm) wide elastic.

Adhesive 55 is used to bond the elastic between the outer cover layer 12 and the body side layer 14. A suitable adhesive includes, for example Findley H2096 hot melt adhesive, available from Findley Adhesives, Milwaukee, Wis.

The leg elastics 48, 50 and crotch elastic 51, including multiple threads in each, are typically about 0.5 inch (13 mm) wide. The elastic may comprise threads, ribbons, a film or composite. The threads, ribbons, etc., may be multiple and may be applied as a composite. The front leg elastics and the crotch elastics may be threads, preferably numbering three threads which are spaced about 0.17 inch (4.3 mm) apart. Back leg elastics numbering up to six threads may have a width of about 0.75 inch (19 mm) and a spacing of about 0.15 inch (3.8 mm) apart. The threads may be made of any suitable elastomeric material. As with the waist elastics, one suitable material is spandex such as Lycra® threads available from Dupont, Wilmington, Del. Suitable leg elastics include threads having a total decitex (g/1000 m) of about 3760 for a 0.5 inch (13 mm) wide elastic.

Adhesive 55 is used to bond the several elastics 48, 50, and 51 to the outer cover layer 12, the body side layer 14, and the support sheet 53.

To provide a snug leg fit and to draw up the sides of the crotch 24 to generally form a cradle to receive the primary absorbent, the leg elastics 48, 50, and the crotch elastics 51, are elongated/stretched when applied to the layers 12, 14 respectively.

Preferably, the leg elastics 48, 50 are applied in multiple segments, with the amount of elongation of each segment while being incorporated into the blank 10 being determined according to the position to be occupied by the respective segment. Regarding the front and back leg elastics, the front leg elastics are elongated less than the back elastics. Regarding the combination of the front elastics, the back elastics, and the crotch elastics, the front and crotch elastics are elongated less than the back elastics. Preferably, the front and crotch elastics are elongated to about 150% and the back elastics, along the leg openings, are elongated to about 300%. Using different elongations in the different sections of elastics, and corresponding differing tensions via different combinations of number of elements, various decitex of the elastic elements and elongations, facilitates attachment of the primary absorbent pad 66, reduces tightness in the groin area, and reduces bunching of the crotch 24 caused by high leg elastic retraction. The back leg elastic is under higher elongation to help keep the seat of the garment from creeping up with movement during use.

Figure 6:
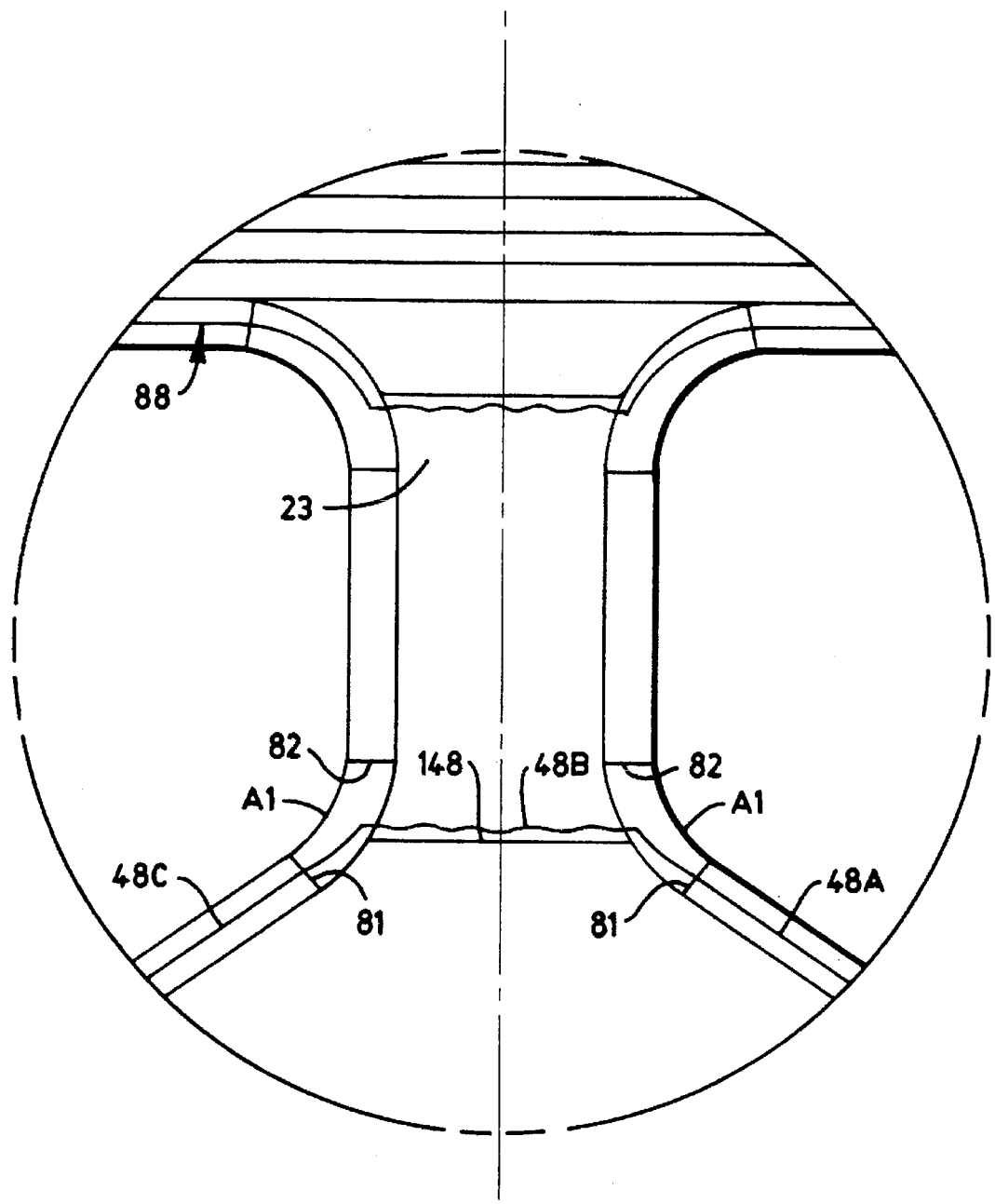
FIGS. 6 and 7 are enlarged cut-away views of a fragment of the blank of FIG. 1, showing detail of the cross-crotch elastics.
Figure 7:
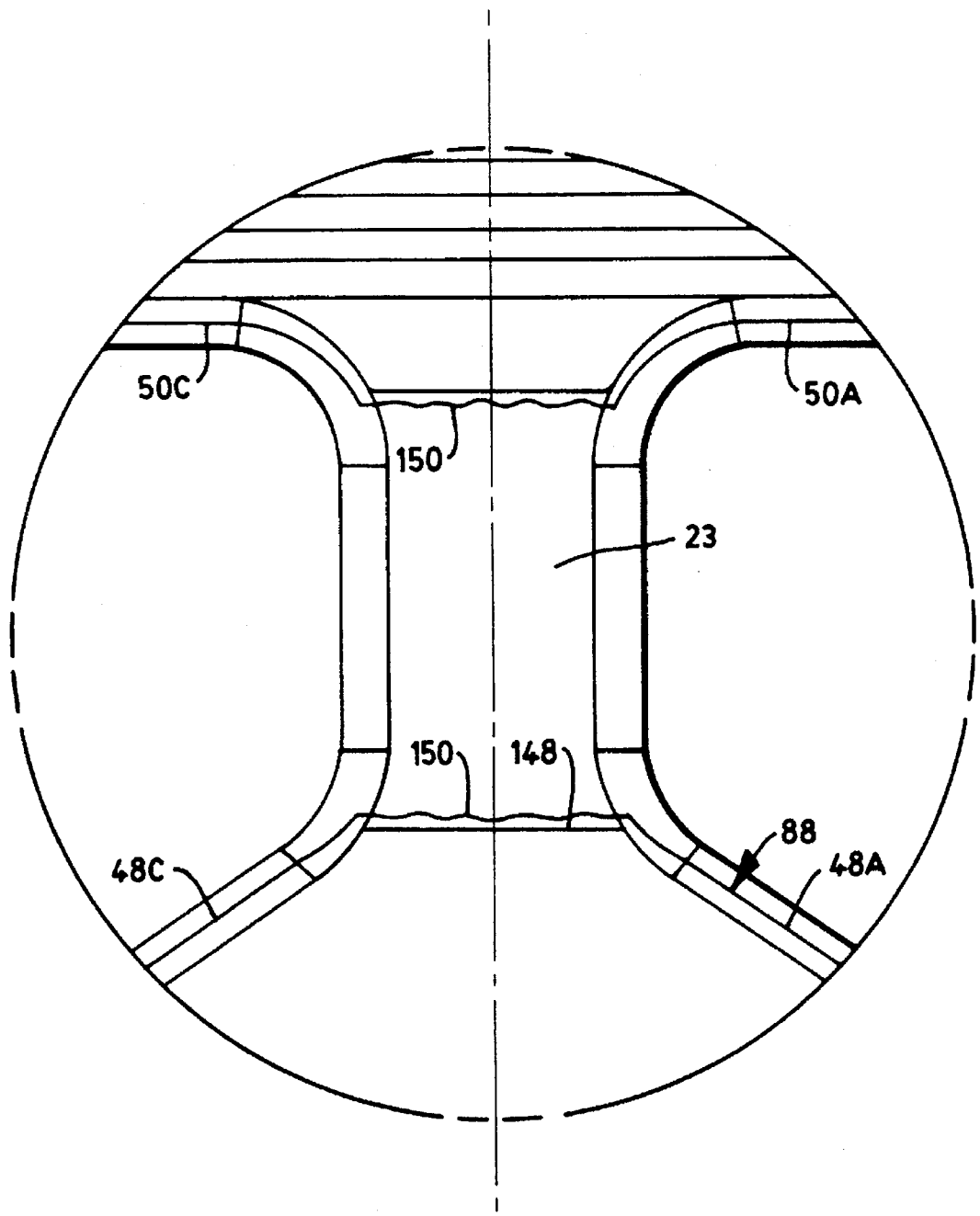

Referring now to FIGS. 1, 6, and 7, the suggested six (back) and three (front) threads of elastic on the respective back and front leg elastics 48 and 50 are each represented as single threads 88 of elastic. The following description of the characteristics and use of the single threads applies to the usual multiple threads suggested above.

The composite of the elastics extending about each of the leg openings 44 and 46 comprises a portion of the back leg elastics 48, a portion of the front leg elastics 50, and one of the left and right crotch elastics 51. Referring specifically to FIGS. 1, 2, 6, and 7, the back leg elastic 48 extends, as a first section 48A, from a first locus 90 at or adjacent the edge 28 of the blank, width-wise across the blank at a substantially consistent acute angle $\alpha$ with the centerline A—A toward a first edge of the blank at front waist portion 18, and generally follows the back edge 74 of the leg opening 46 along the straight section 76A and onto the first arcuate section "A1" toward the crotch 24, generally terminating in the first arcuate section "A1," at or near the crotch 24. Back leg elastic 48 extends, as a second section 48B, from the first arcuate section "A1" across the crotch to the second arcuate section "A1." From the second arcuate section "A1," the back leg elastic 48 extends, as a third section 48C, at an acute angle $\alpha$ with the centerline A—A away from the front waist portion 18, generally following the back edge 74 of the leg opening 44 along the straight section 76B to a second locus 92 at or adjacent edge 34. In the flat configuration shown for the blank in FIGS. 1, 2, 6, and 7, sections 48A and 48C are elongated 250%, while section 48B is substantially relaxed. Preferably, section 48B includes a modest amount of slack in the elastic.

The front leg elastic 50 extends, as a first section 50A, from a third locus 94 at or adjacent the side edge 26 of the blank width-wise across the blank and generally following the front leg edge portion 70 along its longitudinal straight section 72A, and onto the first arcuate section "A2" toward the crotch 24, generally terminating in the first arcuate section "A2," at or near the crotch 24. Front leg elastic 50 extends, as a second section 50B, from the first arcuate section "A2" across the crotch to the second arcuate section "A2." From the second arcuate section "A2," the front leg elastic 50 extends, as a third section 50C, width-wise across the blank and generally following the front leg edge portion 70 along its longitudinal straight section 72B to a fourth locus 96 at or adjacent side edge 32. In the flat configuration shown for the blank in FIGS. 1, 2, 6, and 7, sections 50A and 50C are elongated 150%, while section 50B is substantially relaxed. Preferably, section 50B includes a modest amount of slack in the elastic. Thus, in the embodiment seen in FIGS. 1, 2, 6, and 11, the front and rear leg elastics extend across the width W1 of the blank 10 as one or more continuous threads.

The crotch elastics 51 extend generally between the back and front leg elastics 48 and 50, with respective ends of the crotch elastics generally being disposed at or adjacent the respective arcuate sections "A1" and "A2." Accordingly, the elastic properties extant about each leg opening result from the combined contributions of the respective back leg section (e.g. 48A), the respective front leg section (e.g. 50A), and the respective crotch elastic 51.

The reason for providing leg elastics in multiple sections is at least two-fold. First, using multiple sections of elastics facilitates placing of the elastics on the outer cover layer 12 while maintaining advantageous production speeds. As suggested in FIGS. 1, 8, and 9, a continuous series of blanks or blank pre-forms of e.g. FIG. 1 is made as a sequence of such blanks and/or blank pre-forms on a continuous web 100 including outer cover layer 12 as a substrate, with the garment width "W1" of the blanks disposed in the "with machine" direction of the processing apparatus, and the garment length "L1" of the blanks disposed transversely in e.g. the cross machine direction of the processing apparatus and the web 100. In such arrangement, the front and back waist elastics 40, the front and back body elastics 64, and the front and back leg elastics 50, 48 respectively can all be assembled into the blank by appropriate continuous feeding of respective continuous threads of elastics into the processing apparatus in the "with machine" direction while the web 100 advances continuously in the "with machine" direction at an essentially constant speed.

Given the orientation of the crotch elastics at essentially 90° to the direction of advance of the web 100, the step of placing the crotch elastics as a portion of a continuous element of either the front or back leg elastics would suggest either (1) momentarily, regularly, intermittently stopping the advance of the web 100 while the crotch elastic is fed into place, or (2) severely slowing the web 100 and severely driving an elastics guide, in a direction transverse to the web in order to apply the crotch elastic while the web was thus slowed. In either scenario, the speed changes would place severe stresses on the respective drive apparatus for slowing and accelerating the web, as well as placing severe stresses on the web.

The invention contemplates, rather, placing the crotch elastics in the blank 10 as a separate operation, placing separate elastics segments as described hereinafter, where the crotch elastics segments are first elongated and oriented transverse to the web 100 and are then placed on the web as the web passes the appropriate operating station subsequent to placing the leg, body and waist elastics in the blank, though the sequence of placing the elastics is not critical.

Figure 8:
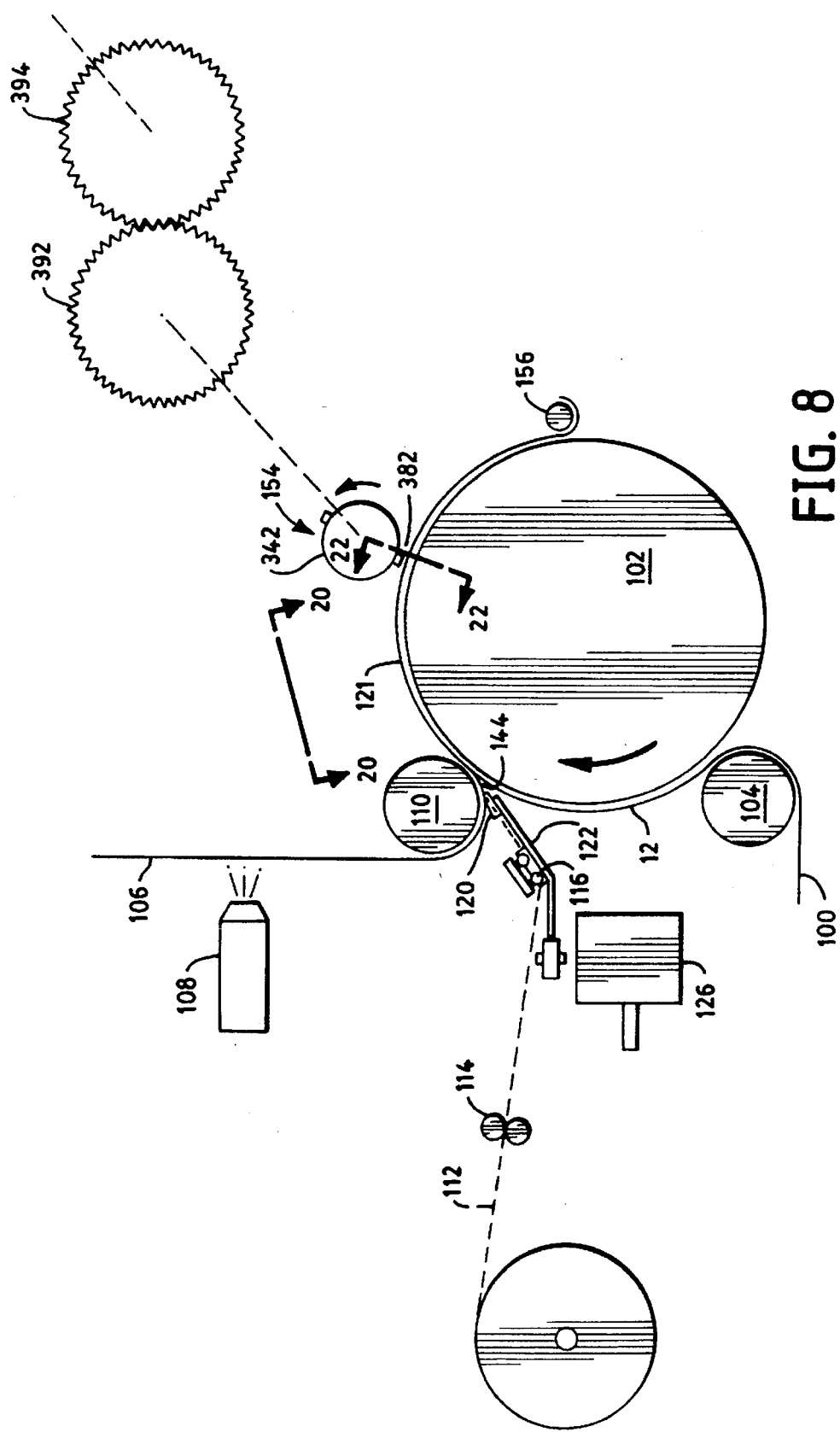
FIG. 8 is a side elevation view of a portion of an equipment layout for fabricating and otherwise processing the blanks of the invention.
Figure 9:
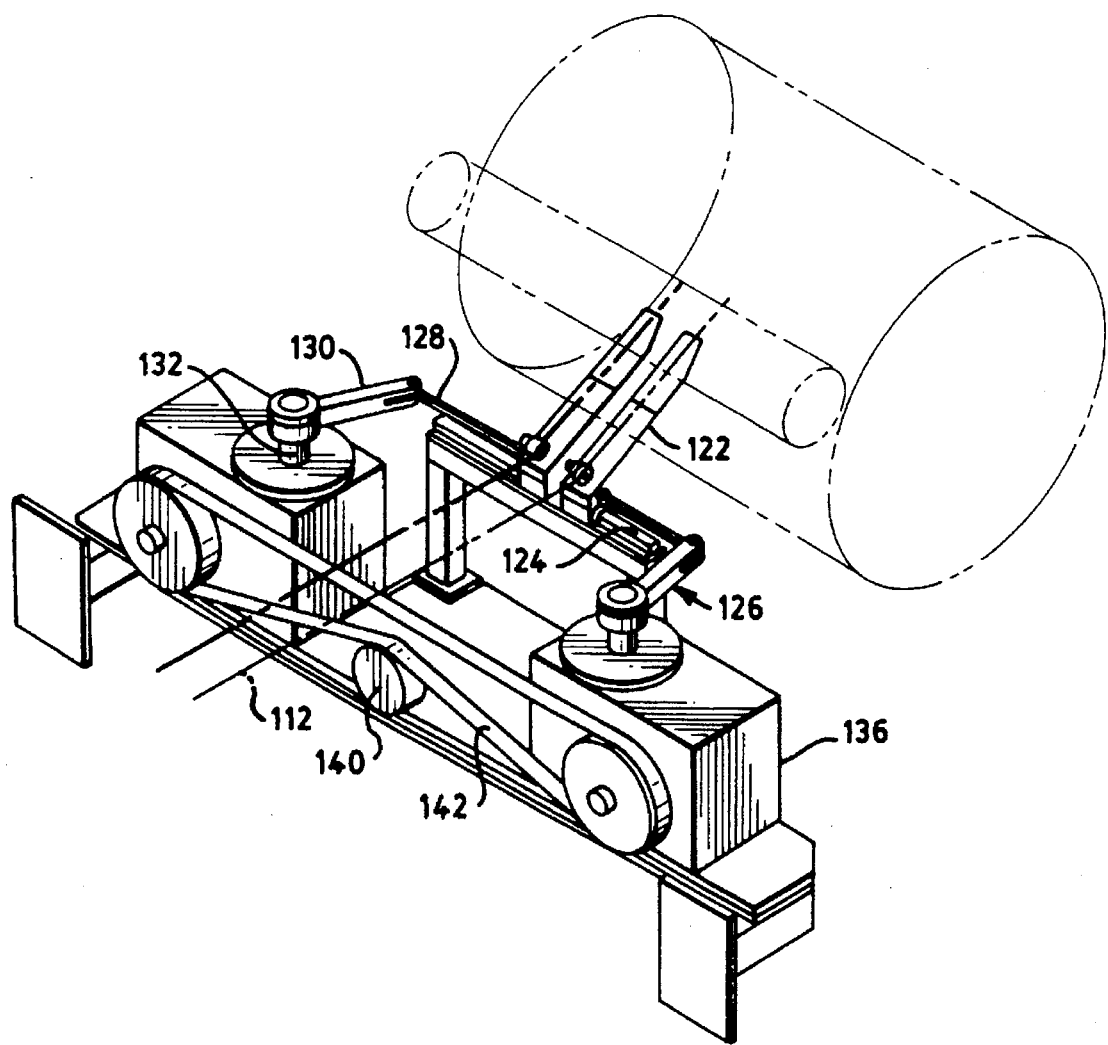
FIGS. 9 and 10 are pictorial views of the nip area of the elevation shown in FIG. 8.
Figure 10:
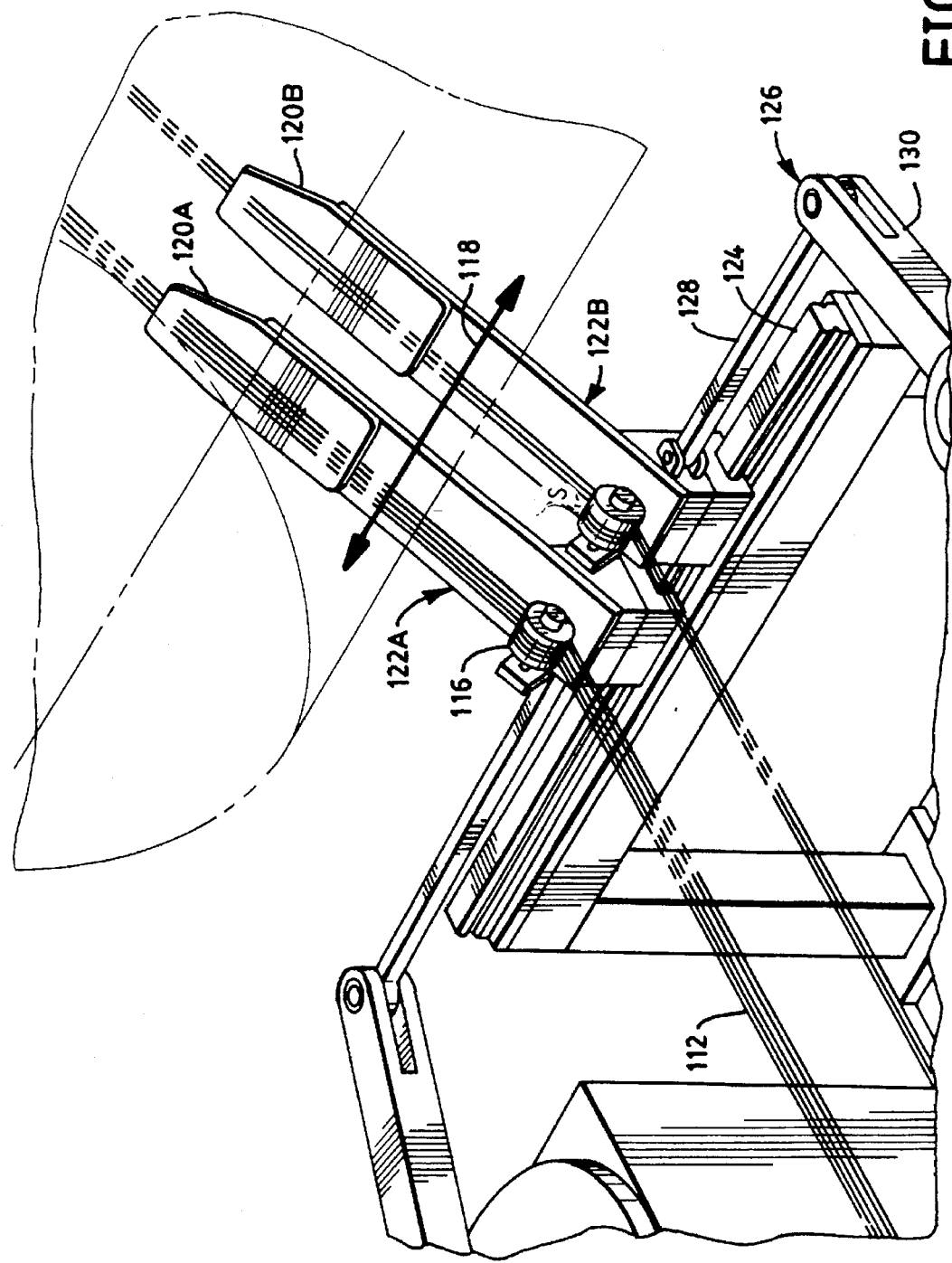

Referring now to FIGS. 8, 9 and 10, a first continuous web 100, which ultimately becomes cover layer 12, is presented to the outer cover construction roll 102 by turning roll 104. A second continuous web 106, which ultimately becomes body side layer 14, passes by adhesive applicator 108 and over turning roll 110, and is pressed against the construction roll 102 by turning roll 110. Elastic threads 112 are fed from a continuous supply of elastic thread (not shown), through feed nip 114, through thread guides 116 and sets of guide fingers 120A and 120B, and between continuous web 100, now incorporating therein the continuous webs 106 that form elements 19, 21 of the body side layer 14, at the nip 144 formed by construction roll 102 and turning roll 110.

Figure 11:
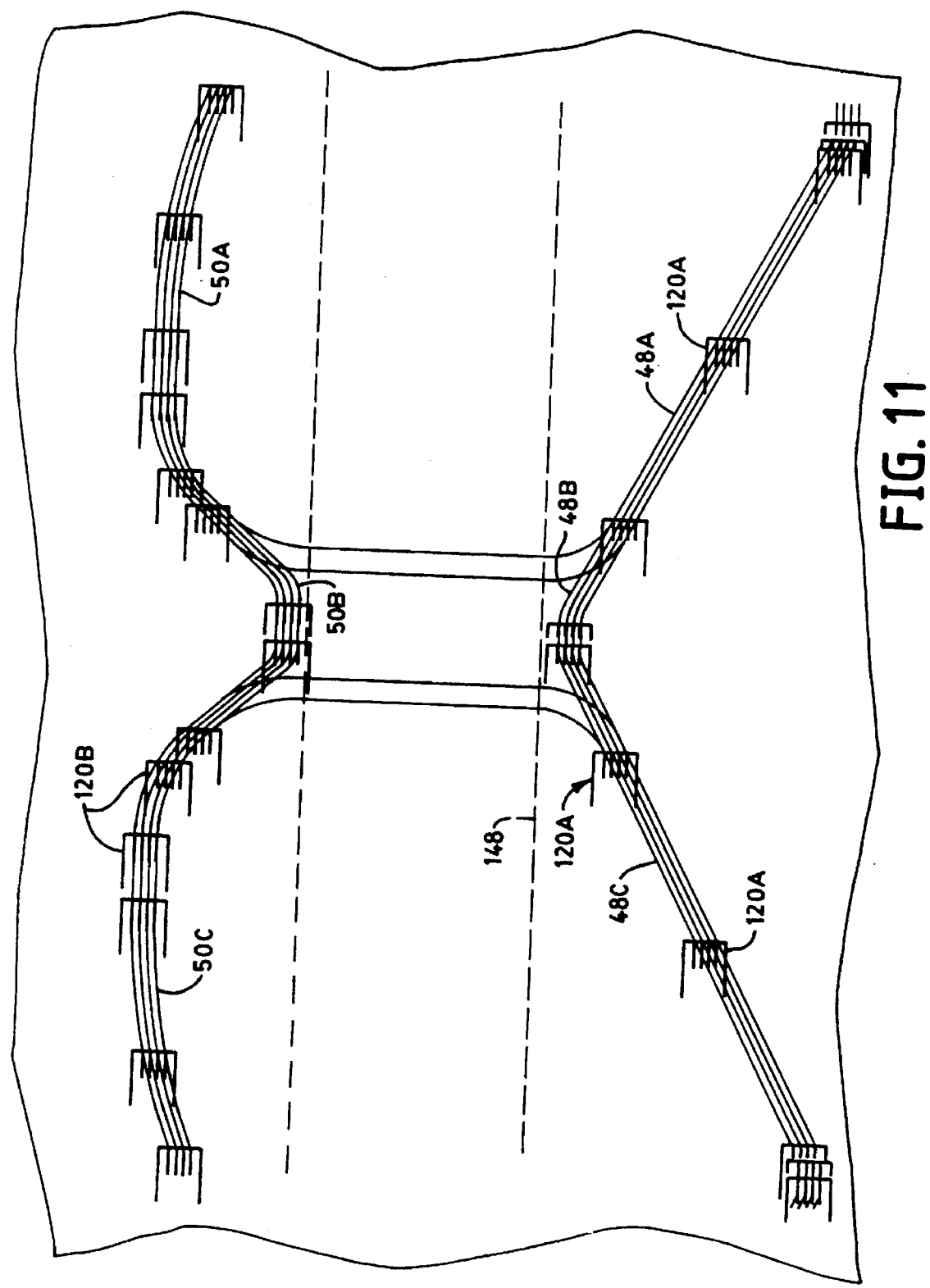
FIG. 11 is a plan view showing the relative transverse positioning of the front and back leg elastics along the advancing web while the outer cover layer and body side layer are being joined.

Referring especially to FIGS. 10 and 11, thread guides 116 and corresponding sets of guide fingers 120A and 120B are elements of lateral thread guides 122A and 122B respectively. Each of the lateral guides 122A and 122B is mounted on a transverse slide bar 124 for sliding transverse to the with machine direction of travel of the webs 100, 106. Each lateral guide 122 is connected to a transverse drive mechanism 126 including linkage arms 128 and 130, vertical drive shaft 132, and a cam follower inside cam housing 136. The cam followers follow corresponding cams inside the respective cam housings. The cams are linked to the machine drive shaft 140 by drive belt 142. Thus, the linkage arms 128, 130, and correspondingly the thread guides and the sets of guide fingers, move transversely with respect to the with machine direction of the webs as the drive shaft turns. The end result is that rotation of the processing line drive shaft 140 effects oscillating transverse motion of the thread guides and the sets of guide fingers, as indicated by the direction arrow 118 shown in FIG. 10, in cooperation with the design of the cams and cam followers.

Referring to FIG. 8, the guide fingers 120 are positioned close to the nip 144 so that they closely control the transverse positions of the leg elastics with respect to the webs 102 and 106 as the webs 102 and 106 enter the nip 144 and correspondingly trap the elastics between them, fixing the position of the elastics between them by means of adhesive 55. Accordingly, the guide fingers 120 are preferably physically positioned, and provide guidance to the threads of elastic, within two inches of the nip 144. To the extent the fingers can be placed closer to the nip 144, they provide more positive guidance to the elastic. By careful design of the guide fingers 120, and by careful control of the positioning of the guide fingers 120 with respect to nip 144, the guide fingers 120 can be advantageously positioned within 0.5 inch of the line of contact defined at the nip between rolls 102 and 110.

The limitation on how close the guide fingers 120 can be placed to the nip is controlled by the ability to design fingers which can affirmatively guide the threads of elastic while avoiding having the fingers themselves drawn into the nip. The criticality of urging the fingers as ultimately close as possible to the nip can be somewhat attenuated by directing the threads 112 onto the adhesive-coated layer 14 ahead of nip 144, preferably instantaneously ahead of the nip 144, as suggested by the depiction in FIG. 8. By directing the threads of elastic onto web 106 ahead of the nip, the open distance spanned by the threads between the fingers 120 and the adhesive-coated web 106 is minimized, being held to less than 0.5 inch, for example 0.25-0.375 inch (6 mm to 10 mm).

The transverse movement of the lateral guides 122, and thus fingers 120, as the webs advance along the processing line, creates transverse positioning of the elastic threads 112 with respect to the with machine direction of the advancing webs 100 and 106. FIG. 11 shows the general pattern of transverse movement of the sets of guide fingers 120A and 120B relative to the movement of the webs in the with machine direction, along the processing line. In FIG. 11, the sets of fingers 120A and 120B are depicted at several locations along what will, later in the processing, become the front and back edges of the leg openings 44, 46, to indicate that it is the positioning of the sets of fingers 120A and 120B, and the dynamic changing of that positioning by the drive mechanism 126, that determines the instantaneous transverse location of the elastics in the web at any point and time while the elastics are being placed in the web at nip 144 as shown in FIGS. 8-11.

Comparing FIGS. 1, 8, 10, and 11, it is seen that the set of fingers 120A generally places the threads of the back leg elastics generally parallel to each other in the combined web 121, while the set of fingers 120B generally places the threads of the front leg elastics generally parallel to each other in the combined web, both along their respective portions of the designed paths defining the front 70 and back 74 edges of the leg openings 44 and 46. The threads of elastic deviate slightly from their parallel relationships with each other as the elastic threads traverse paths that deviate from the with machine direction, the distance between the threads 88 being generally constant as they emerge from the fingers 120. Such deviations from the parallel, resulting from the cross machine traverse of the elastics, are included herein within the phrase "generally parallel" as respects the relationships of the threads of elastic to each other.

It will be understood that FIG. 11 represents only one garment in the continuous sequence of garment blanks or blank pre-forms 10 contained in the combined web 121 through nip 144. It will also be understood that the web passing through the nip 144 is further acted upon at a cutter, described hereinafter, to cut away material from the combined web 121 in creating the leg openings 44 and 46.

In general, then, webs 100 and 106 are provided as substantially endless rolls from unwind stands (not shown). Web 106 is typically provided as first and second, side-by-side front and back layer elements, separated by the space 23, and ultimately become the elements 19 and 21 of the body side layer 14. Space 23 separates the elements 19 and 21, and generally corresponds with the crotch and the portion of the blank 10 which is cut out to form leg openings 44 and 46. Adhesive 55 is applied to the front and back elements 19 and 21 of web 106 by adhesive applicator 108. Webs 100 and 106 are joined adhesively, with elastic threads being interposed between the webs at nip 144, and with space 23 interposed between the front and back elements 19, 21, to thereby form the outer cover layer 12 and the body side layer 14 comprised in the blank 10.

The transverse positions of the elastics change according to a pre-set path of transverse movements, driven by the drive shaft 140 which drives and times the several operations along the processing line. The threads of elastic 112, as placed by the guide fingers 120, traverse respective paths whereby the threads of elastics ultimately follow the front and back edges of the leg openings 44 and 46, as defined at the subsequent cutter for cutting the leg openings, in registration with the advance of the web, and accordingly, with the advance of the series of garment blanks 10 being defined in the web at nip 144 and at a subsequent cut-off cutter, described hereinafter.

The portions of the threads of elastic located along the front and back edges of the leg openings are stretched. The portions traversing across the width of the crotch are substantially relaxed. The crotch elastics 51 are separately placed in the blank 10 at a later processing station, described hereinafter.

Figure 12:
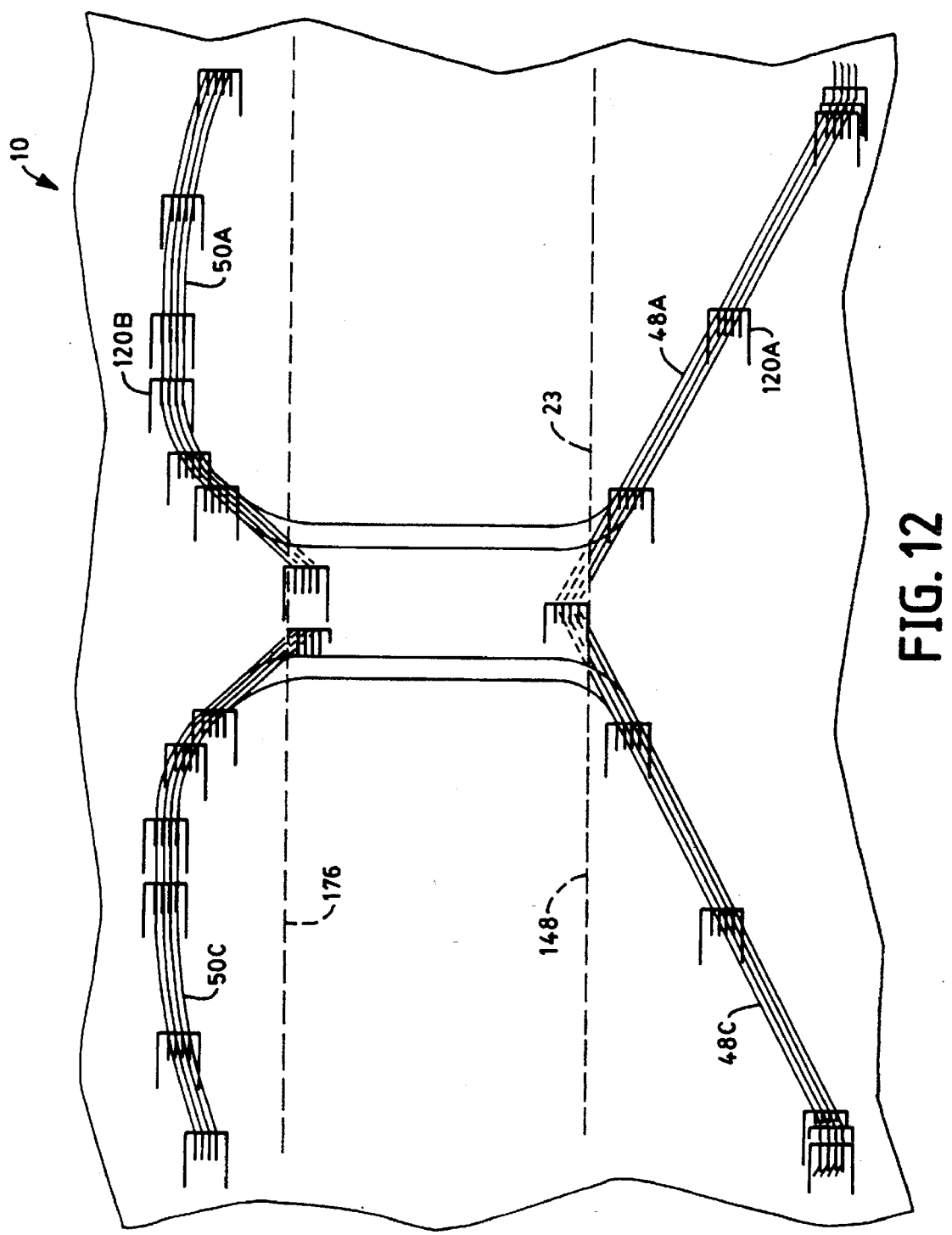
FIG. 12 is a plan view as in FIG. 11, showing an alternate pattern for the elastic elements.

A second embodiment of the blank 10 is illustrated in FIG. 12. In the second embodiment, the inner edge 148 of back layer element 21 is disposed rearwardly of that same edge 148 as depicted in the embodiment of FIG. 10, while the guide fingers 120A traverse the same path as in FIG. 10. Accordingly, as the threads of elastic 112 extend across the crotch 24, the threads 112 are guided forwardly of edge 148, into space 23, and are thus not held between the layers 12 and 14, and thus are not controlled by the adhesive 55 on layer 14. Rather, the tension is maintained on the threads of elastic 112 across the crotch 24, such that the threads retract along the edge 148 of the layer element 21 in a configuration that loosely resembles a rope under tension. The rope is subsequently severed whereby the severed ends of the threads retract to positions generally defined by the intersection of the edge 148 of the back layer element 21 with the path of the threads adhesively held between layer 12 and the back layer element 21. Thus, the threads 112 generally include loose intermediate ends 150 after being cut, as shown in FIG. 7.

Body elastics 64 and waist elastics 40 can be incorporated at nip 144 in the conventional manner of providing stationary feeds and guides at the nip, and accordingly, are not further described.

Wherever herein this teaching refers to "multiple" elements, e.g. multiple threads of elastic or multiple paths of traverse, any two or more such elements are included.

Figure 13:
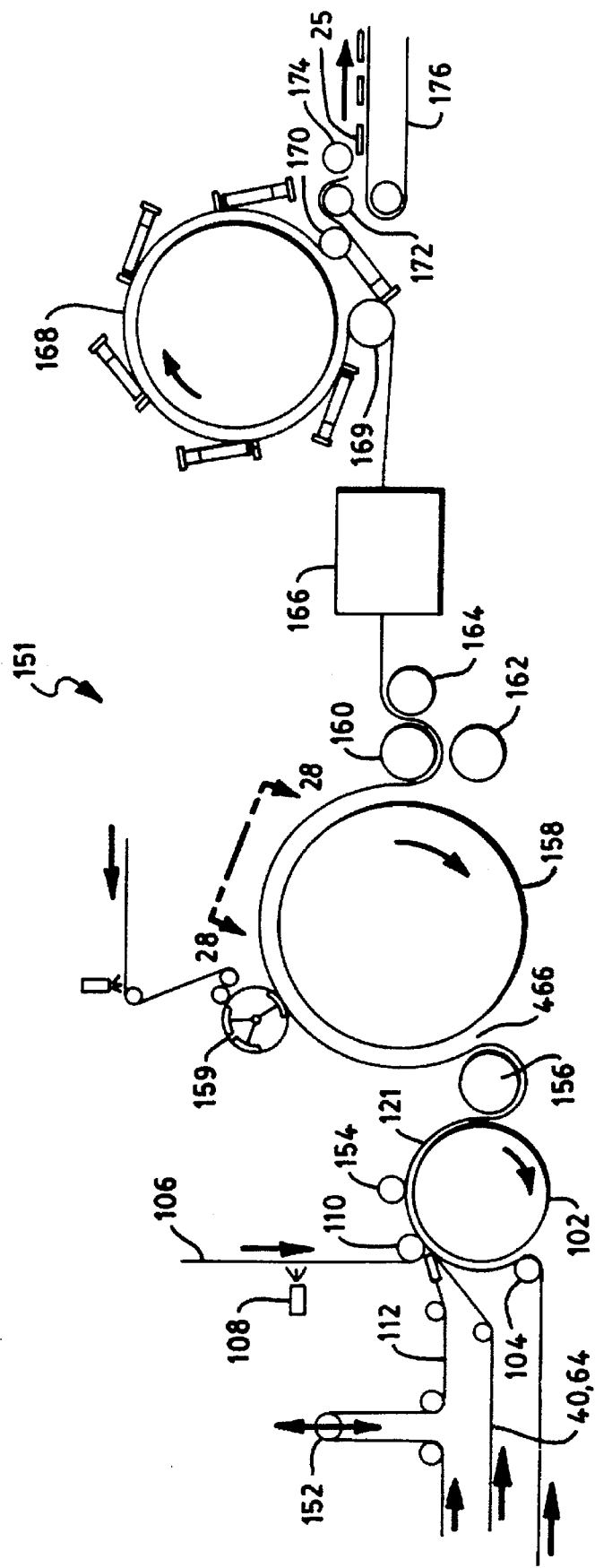
FIG. 13 is a side elevation showing several work stations used in fabricating garments made according to the invention.

The description to this point has focused on the garment, the blanks, and the methods of incorporating the leg elastics into the blanks. FIG. 13 shows a significant portion of a processing line incorporating the outer cover construction roll 102, in a process for fabricating the garment 25. As seen therein, the waist and body elastics 40, 64 are preferably incorporated into the combined web at the nip 144.

Still referring to FIG. 13, to the extent the front and back leg elastics 48 and 50 are incorporated into the webs and confined entirely between the layers 12 and 14, an active dancer roll subsystem, generally designated 152, to be described hereinafter, is used to relax the tension in the threads 112 of leg elastics as the threads are fed into the nip at loci representing the cross crotch portion of each respective blank, and to apply tension as the threads of elastic are placed along the respective front and back portions of the leg openings.

To the extent the front and back leg elastics 48 and 50 are incorporated into the webs, including a portion of the threads emerging from between the layers 12 and 14, the dancer roll subsystem 152 is not used; rather a cutter subsystem 154 is applied as shown at e.g. a later position on the outer cover construction roll 102.

From the outer cover construction roll, the combined web 121 passes over turning roll 156 and onto assembly roll 158. As will be described hereinafter, the crotch elastics 51, including a carrier web, are positioned in the blanks 10 on the assembly roll 158 by crotch elastics applicator subsystem 159. From assembly roll 158, the web passes around turning roll 160. Turning roll 160 acts as an anvil for one or more cutters on roll 162, which cut the leg openings 44, 46 in the combined web 121. The combined web then passes over turning roll 164, and goes to folder 166. In the folder 166, the combined web is folded lengthwise onto itself such that the front and back portions of the blank 10 are in facing relation with each other. The folded web then passes onto and over side-seam bonder 168, where the side seams 30 and 36 are formed. From the side seam bonder, the now-formed garments, still in the web, pass about turning rolls 170 and 172, to cutter roll 174. Turning roll 172 acts as an anvil for cutter roll 174, which cuts the individual, completely formed garments 25 from the web. The finished garments are deposited on conveyor 176, and carried away for packaging.

THE DANCER ROLL

The following description of the dancer roll subsystem is made in the context of the processing line 151 shown in FIG. 13. Given the disclosure herein, the novel dancer roll subsystem can, of course, be used with other methods and apparatus for fabricating products using flexible web processes.

Figure 14:
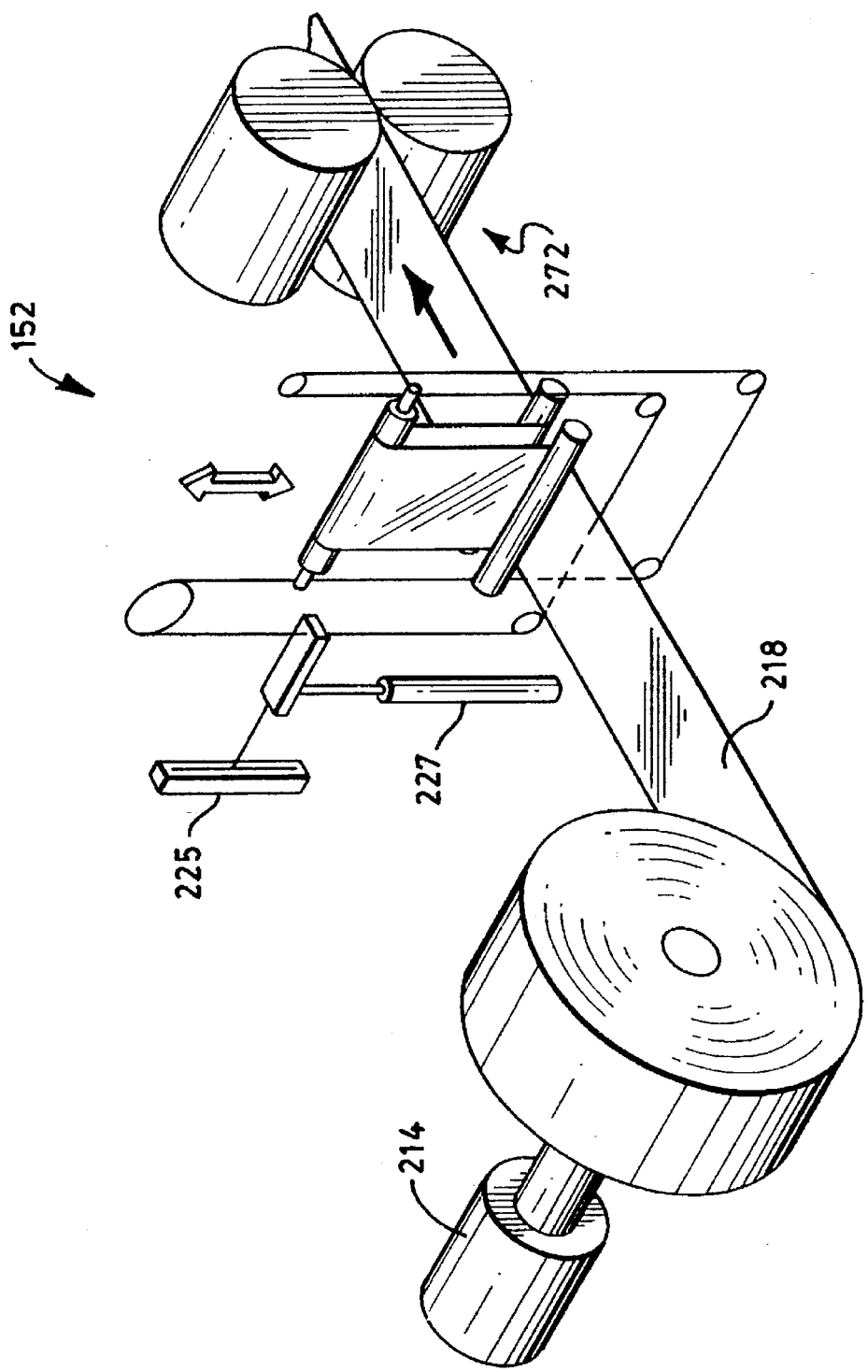
FIG. 14 is a pictorial view of part of a conventional processing operation, showing a dancer roll adjacent the unwind station.

FIG. 14 illustrates a typical conventional dancer roll control. Speed of advance of web material 218 is controlled by an unwind motor 214 in combination with the speed of the nip 272 downstream of the dancer roll. The dancer subsystem 152 employs lower turning rolls before and after the dancer roll, itself. The dancer roll moves vertically up and down within the operating window defined between the lower turning rolls and the upper turning pulleys in the endless cable system. The position of the dancer roll in the operating window, relative to (i) the top of the window adjacent the upper turning pulleys and (ii) the bottom of the window adjacent the turning rolls is sensed by the position transducer 225. A generally static force having a vertical component is provided to the dancer roll support system by the air cylinder 227.

In general, in the conventional dancer roll subsystem shown in FIG. 14, to the extent the process take-away speed exceeds the speed at which web material is supplied to the dancer roll, static forces on the dancer roll cause the dancer roll to move downwardly within its operating window. As the dancer roll moves downwardly, the change in position is sensed by the position transducer 225, which sends a corrective signal to the motor controlling the speed at which the web is fed to the dancer subsystem, to increase the speed of the feed/unwind. The speed of the feed increases enough to return the dancer roll to the mid-point in its operating window. By corollary, if the take-away speed lags the speed at which web material is supplied to the dancer roll, static forces on the dancer roll cause the dancer roll to move upwardly within its operating window. As the dancer roll moves upwardly, the change in position is sensed by the position transducer 225. As the dancer rises above the mid-point in the operating window, the position transducer 225 sends a corresponding corrective signal to the feed/unwind motor to decrease the speed of the feed, thereby returning the dancer roll to the mid-point in the operating window.

The above conventional dancer roll subsystem is limited in that its response time is controlled by the gravitational contribution to vertical acceleration of the dancer roll, and by the mass of equipment in e.g. the unwind apparatus that must change speed in order to effect a change in the unwind speed.

Figure 15:
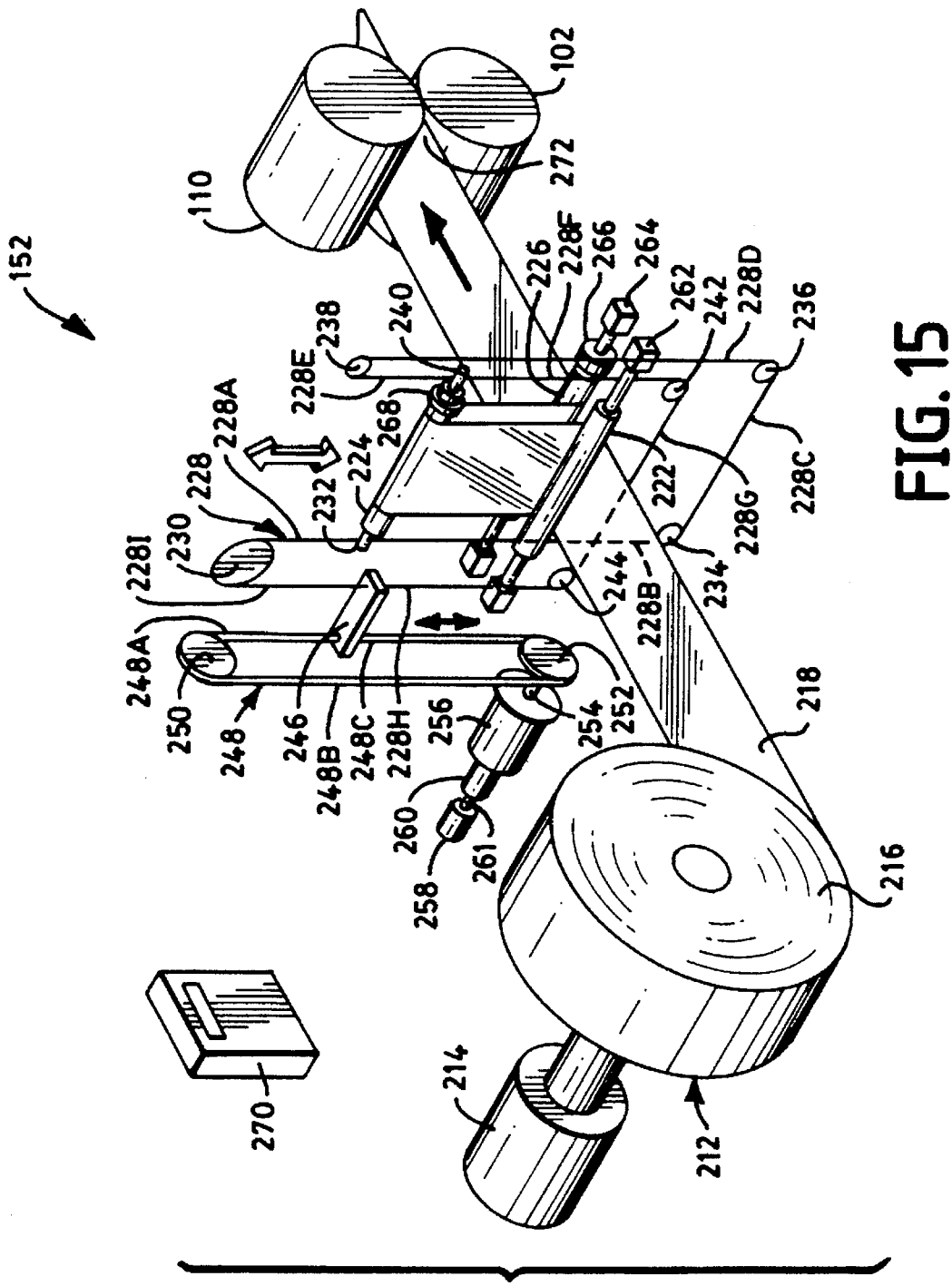
FIG. 15 is a pictorial view of one embodiment of the invention, again showing a dancer roll adjacent the unwind station.

Referring to FIG. 15, the dancer roll subsystem 152 of the invention incorporates an unwind 212, including unwind motor 214 and roll or spool 216 of raw material. A web 218 of the raw material is fed from the roll 216, through the dancer subsystem 152, to the further processing elements of the converting process downstream of the dancer subsystem 152.

In the dancer subsystem 152, the web of material 218 passes under turning roll 222 before passing over the dancer roll 224, and passes under turning roll 226 after passing over the dancer roll 224. As shown, the dancer roll 224 is carried by a first endless drive chain 228.

Starting with a first upper turning pulley 230, the first endless drive chain 228 passes downwardly as segment 228A to a first end 232 of the dancer roll, and is fixedly secured to the dancer roll at the first end 232. From the first end 232 of the dancer roll, the drive chain continues downwardly as segment 228B to a first lower turning pulley 234, thence horizontally under the web 218 as segment 228C to a second lower turning pulley 236. From second lower turning pulley 236, the drive chain passes upwardly as segment 228D to a second upper turning pulley 238. From second upper turning pulley 238, the drive chain extends downwardly as segment 228E to the second end 240 of the dancer roll, and is fixedly secured to the dancer roll at the second end 240. From the second end 240 of the dancer roll, the drive chain continues downwardly as segment 228F to a third lower turning pulley 242, thence back under the web 218 as segment 228G to the fourth lower turning pulley 244. From fourth lower turning pulley 244, the drive chain extends upwardly as segment 228H to, and is fixedly secured to, connecting block 246. From connecting block 246, the drive chain continues upwardly as segment 228I to the first upper turning pulley 230, thus completing the endless loop of drive chain 228.

Connecting block 246 connects the first endless drive chain 228 to a second endless drive chain 248. From the connecting block 246, the second endless drive chain 248 extends upwardly as segment 248A to a third upper turning pulley 250. From upper turning pulley 250, the endless drive chain extends downwardly as segment 248B to fifth lower turning pulley 252. From fifth lower turning pulley 252, the drive chain extends back upwardly as segment 248C to the connecting block 246, thus completing the endless loop of drive chain 248.

Shaft 254 connects the fifth lower turning pulley 252 to a first end of servo motor 256. Dancer roll position sensor 258 and dancer roll translational velocity sensor 260 extend from the second end of servo motor 256, on shaft 261.

Load sensors 262, 264 are disposed on the ends of turning rolls 222, 226 respectively for sensing stress loading on the turning rolls transverse to their axes, the stress loading on the respective turning rolls 222, 226 being interpreted as tension on the web.

Velocity sensor 266 is disposed adjacent the end of turning roll 226 to sense the turn speed of turning roll 226. Velocity sensor 268 is disposed adjacent the second end 240 of dancer roll 224 to sense the turn speed of the dancer roll, the turning speeds of the respective rolls being interpreted as corresponding to web velocities at the respective rolls. The dancer subsystem 152 is controlled by computer controller 270. Computer controller 270 is a conventional digital computer, which can be programmed in conventional languages such as "Basic" language, "Pascal" language, "C" language, or the like. Such computers are generically known as "personal computers," and are available from such manufacturers as Compaq® and IBM®.

Position sensor 258, velocity sensors 260, 266, 268, and load sensors 262, 264 all feed their inputs into the computer controller 270. Computer controller 270 processes the several inputs, computing a velocity set point $$V_p^* = \frac{EA_o}{EA_o - F_c} V_2\left(\frac{F_b}{1 - EA_o}\right) - V_3\left(\frac{F_c}{1 - EA_o}\right),$$

and a target servo motor torque command according to $$T^*_{dancer} = r[F_{d\ static} + b_a(V^*_p - V_p) + k_a(F^*_c - F_c)]$$

where $F^*_{d\ static} = Mg + 2F^*_c$
using the following variables:

$F_{d\ static}$=Static vertical force component on the dancer roll
$F_c$=Tension in the web after the dancer roll
$F^*_c$=Tension in the web, target set point, per process design parameters
$F_b$=Tension in the web ahead of the dancer roll
$b_a$=Control gain constant re dancer translational velocity, in newton seconds/meter
$k_a$=Control gain constant re web tension
Mg=Mass of the dancer roll times gravity.
$V_p$=Instantaneous vertical velocity of the dancer roll immediately prior to application of the second variable vertical force component
$V_2$=Velocity of the web at the dancer roll
$V_3$=Velocity of the web after the dancer roll
$V^*_p$=Vertical velocity of dancer roll, set point
r=Radius of pulley on the servo motor
E=Modulus of elasticity of the web
$A_o$=Cross-sectional area of the unstrained web
$T^*_{dancer}$=Servo motor torque command
$V^*_p$ =represents the target translational velocity of the dancer roll 224, to be reached if the set point $V^*_p$ is not subsequently adjusted or otherwise changed.

A primary objective of the invention is to use active control of the velocity of the dancer roll 224 to control tension in the web 218.

The response time is also affected by the value selected for the gain constant "$b_a$." The gain constant "$b_a$" is selected to impose a damping effect on especially the variable force component of the response, in order that the active variable component of the response not make the dancer roll so active as to become unstable, such as where the frequency of application of the responses approaches a natural resonant frequency of the dancer roll. Accordingly, the gain constant "$b_a$" acts somewhat like a viscous drag in the system. For example, in a system processing e.g. 0.7 ounce per square yard nonwoven fabric, wherein shocks are imposed at the rate of 200 per minute, and the mass of the dancer is one kg, a typical control gain constant "$b_a$" is 2000.

Similarly, the gain constant "$k_a$" compensates generally for web tension errors in the system. A typical gain constant "$k_a$" for the instantly above described processing system is 20,000.

It is contemplated that the operation and functions of the dancer subsystem have become fully apparent from the foregoing description of elements and their relationships with each other, but for completeness of disclosure, the usage of the dancer subsystem will be briefly described hereinafter.

In a first embodiment of the dancer subsystem, a primary objective of the dancer subsystem 152 is to attenuate short term tension disturbances in the web. Such short term tension disturbances might come, for example from unintended, but nonetheless normal, vibrations emanating from equipment downstream of the dancer roll 224, for example bearing vibration, motor vibration, and the like. In the alternative, such tension disturbances can also come from tension disturbances which are intentionally imposed on the web as the web is processed. An example of such intentional tension disturbances is shown in U.S. Pat. No. 4,227,952 Sabee herein incorporated by reference to show a tension disturbance being created with the formation of each tuck or pleat in the web of material being processed.

Whether the tension disturbances are imposed intentionally or unintentionally, the effect on the web is generally the same. As the web 218 traverses the dancer subsystem 152, the web is exposed to an average dynamic tension, representing a normal range of tensions as measured over a span of the web, for example between roll 216 of raw material and the next nip 272 downstream of the dancer roll 224, without considering short term tension disturbances that last for 10 seconds or less.

Figure 18:
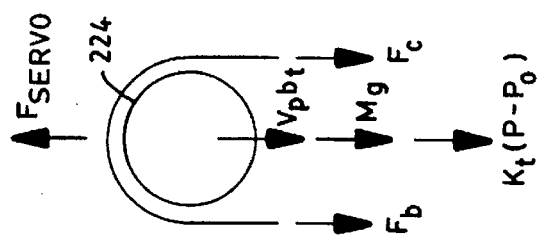
FIG. 18 is a free body force diagram showing the forces acting on the dancer roll.

In order for the dancer roll to operate as a "dancer" roll, the several forces acting on the dancer roll must still, in general, be balanced, as shown in FIG. 18. As shown there, the forces applied by the servo motor are balanced against the tension forces in the web, the weight of the dancer roll, any existing viscous drag effects times the existing translational velocity of the dancer roll, any existing spring effects times the change in positioning of the dancer roll, and the dancer mass time its vertical acceleration at any given time.

The servo motor force generally includes a first generally static force component $F_{d\ static}$, having a relatively fixed value, responsive to the relatively fixed static components of the loading on the dancer roll. The generally static force component $F_{d\ static}$ provides the general support that keeps the dancer roll more-or-less centered vertically in its operating window, between the turning rolls 222, 226 and the upper turning pulleys 230 and 238, responding based on the static force plus gravity. To the extent the dancer roll spends significant time outside a central area of the operating window, the computer 270 sends conventional commands to the line shaft drivers or the like to adjust the relative speeds between e.g. the unwind 212 and the rolls at nip 272 in the conventional way to thus bring the dancer roll generally back to the center of its operating window.

In addition to the static force component $F_{d\ static}$, the servo motor 256 exerts a dynamically active, variable force component, responsive to short-term tension disturbances in the web. The variable force component, when added to the static force component, comprehends the net vertical force command issued by the computer, to the servo motor. The servo motor 256 expresses the net vertical force command as torque $T^*_{dancer}$ delivered through the drive chains 228, 248, and connecting block 246, to the dancer roll.

Accordingly, in addition to the normal passive response of the dancer roll, based on such static forces as mass, gravity, and web tension, the dancer control system of the invention adds a dynamic control component, outputted at the servo motor. The result is a punctuation of the normal dancer system response characteristic with short-term vertical forces being applied to the dancer by the servo motor, with the result that the dancer roll is much more pro-active, making compensating changes in translational velocity much more frequently than a conventional dancer subsystem that responds only passively. Of course, net vertical velocity at any given point in time can be a positive upward movement, a negative downward movement, or no movement at all, corresponding in zero net vertical velocity, all depending on the output command from the computer controller. The computer controller 270, of course, computes both the value and direction of the variable vertical force, as well as the net vertical force.

Figure 16:
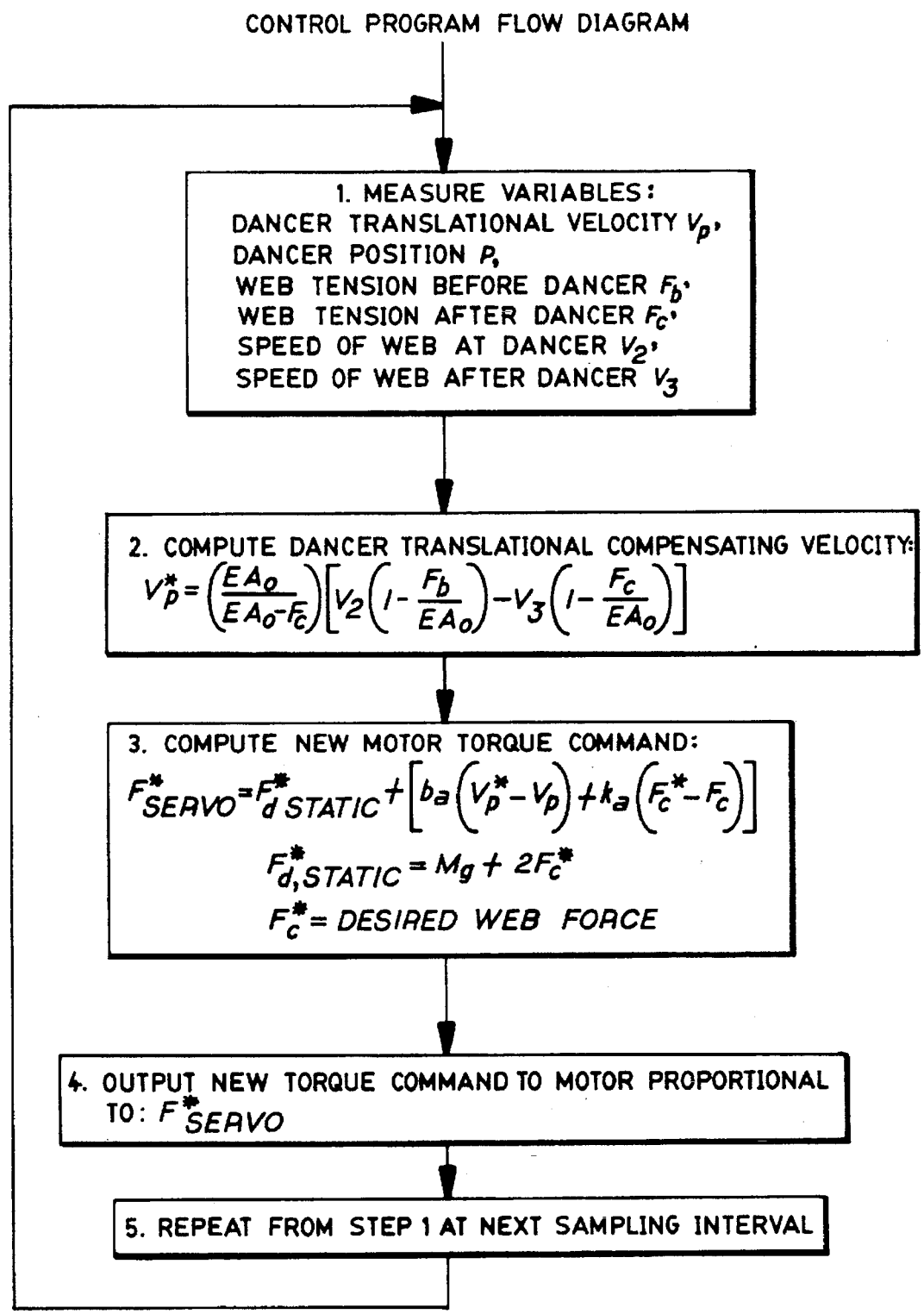
FIG. 16 is a flow diagram representing a control system of the invention.

The general flow of information and commands in a command sequence used in controlling the dancer subsystem 152 is shown in block diagram format in FIG. 16. As seen therein, in step 1 in the command sequence, the variable parameters $V_p$, P, $F_b$, $F_c$, $V_2$, and $V_3$ are measured.

In step 2, the variables are combined with the known constants in the computer, and the computer computes $V^*_p$.

In step 3, $V^*_p$ is combined with additional static values to compute the new motor torque command.

In step 4, the new motor torque command is combined with a servo constant "r" to arrive at the proportional torque command $T^*_{dancer}$ outputted from the servo motor to the dancer roll through the drive chains 228, 248.

In step 5, the sequence is repeated as often as necessary to obtain a response that controls the tension disturbances extant in the web under the dynamic conditions to which the web is exposed.

In general, the tension disturbances of interest in this invention are disturbances which can be attenuated within about 10 seconds, or less, by appropriate response through the novel combination of controls used in the dancer system. The inventors have found that the active variable force component should generally be computed, and any changes in the computed variable force component applied to the dancer roll, at a frequency that applies at least 3, preferably at least about 5 control response changes during the period of existence of the tension disturbance. Of course, any given control command continues to be applied by the servo motor until a new command is received from the computer 270. Thus, if a given tension disturbance exists for a period of 10 seconds, then control responses $T^*_{dancer}$ should be applied at least every 2 seconds during the period of time over which that tension disturbance is in existence.

Since, as discussed above, the first step in the control cycle is sensing/measuring the several variables used in computing the variable force component of the response, it is critical that the sensors measure the variables frequently enough, to detect any tension disturbance that should be controlled early enough, to respond to and suppress the tension disturbance.

In order to have proper control of the dancer subsystem 152, it is also important that the computed responses be applied to the dancer roll frequently enough to control the dancer system. At least 100 responses during the period of existence of any one tension disturbance are preferred. In order to provide sufficient frequency in the response application, especially where there is a variation in the frequency of occurrence of tension disturbances, it is preferred to measure the variables at a multiple of the anticipated desired frequency of applying a response.

Overall, the most critical frequency is the frequency of measuring the variables shown as step 1 in the Flow Diagram, FIG. 16. Similarly, each step in the process must be repeated with a frequency at least as great as the preferred frequency for applying the up-dated torque response commands.

The short-term tension disturbances addressed herein are typically less than 10 seconds in duration. Even shorter term tension disturbances, such as 0.67 second, 0.33 second, or even 0.2 second are readily controlled by the system disclosed herein. For example, a constantly repeated tension disturbance having a period of duration of 10 seconds has a frequency of 6 cycles per minute. A period of duration of 0.67 second suggests a frequency of 100 cycles per minute. A period of duration of 0.33 second suggests a frequency of 200 cycles per minute. A period of duration of 0.2 second suggests 300 cycles per minute. Whatever the frequency of the relevant tension disturbances to be controlled, one need only multiply the frequency of occurrence of the tension disturbances by a factor of 100 to arrive at a first estimation of an acceptable frequency of the response. A few trials with the operating system, using modest variations of the frequency factor will reveal a desirable frequency for the particular processing system, or part of a system, being controlled by the dancer roll 224.

Thus, tension disturbances occurring at a frequency of 100 disturbances per minute suggest a sensing frequency of at least 167 cycles per second. Correspondingly, tension disturbance frequency of 200 disturbances per minute suggests a sensing frequency, and corresponding response frequency of 333 cycles per second. Where a process is, for example, cutting 300 items from the web per minute, or otherwise imposing shocks on the web 300 times per minute, the sensors should be sensing the variables, and the servo motor 256 should be applying a re-computed variable response force component, at least 500 times per second.

The dancer subsystem 152 of this invention can advantageously be used with any dancer roll, at any location in the processing line. If there are no short term tension disturbances in the web, the dancer roll will operate like a conventional dancer roll. Then, when short term tension disturbances occur, the control system will automatically respond, to attenuate the short term tension disturbances.

Figure 19:
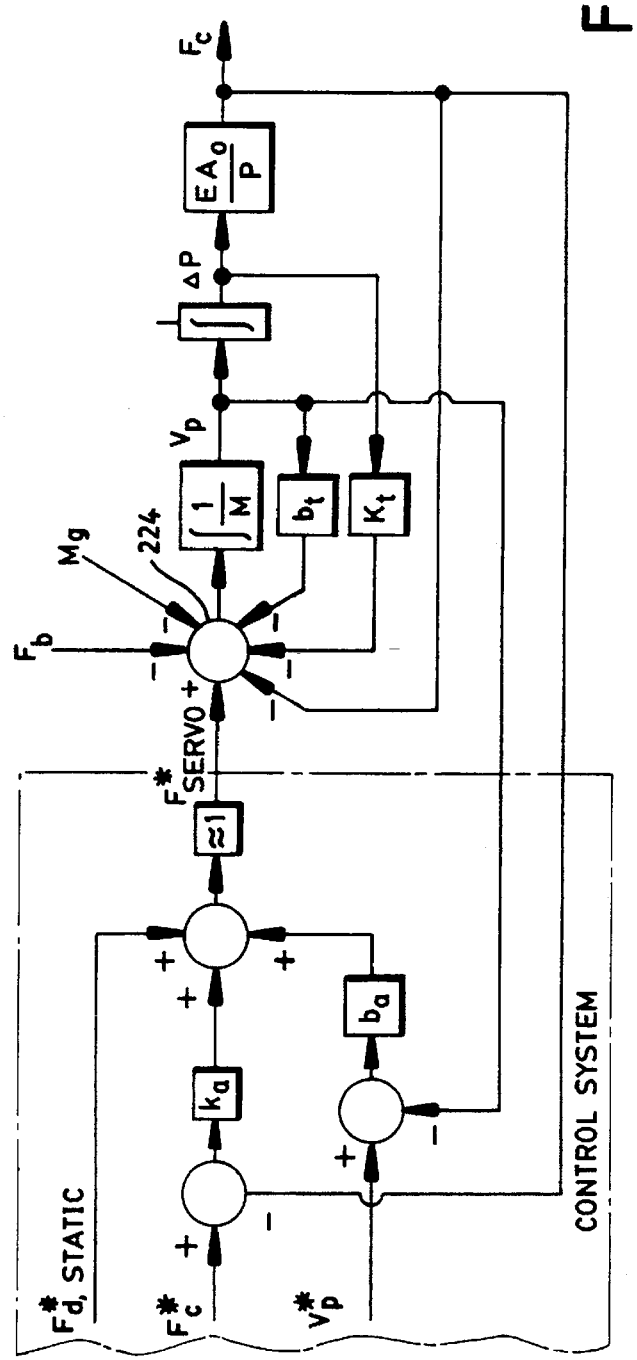
FIG. 19 is a block diagram of a control system for the dancer roll.

Referring to FIG. 19, the dashed outline, represents calculations that occur inside the computer 270, with the resultant output of $F^*_{servo}$ being the output to the servo motor. The circle to the right of the computer controller represents the dancer roll 224, along with the several forces which act on the dancer roll. "M" represents the mass of the dancer roll 224; "g" represents gravity; and "P" represents the position of dancer roll 224.

As used herein, the term "tension disturbance" means a sudden pull such as to form a tuck, or a sudden relaxation as to temporarily eliminate all, or almost all, of the tension in the web. It includes all tension disturbances that can be significantly and finally attenuated by active response of the dancer control system. Correspondingly, it excludes normal increases and decreases in overall drive-line speed, which will overwhelm the dancer system if not corrected at, for example, the unwind station drive shaft.

"Existence for no more than 10 seconds," referring to a tension disturbance includes disturbances that would last for more than 10 seconds if not treated with the active dancer subsystem, but excludes disturbances where the active dancer treatment as disclosed herein cannot attenuate the entire disturbance within 10 seconds. Thus, the disturbances controlled by the control system of the invention can include single-step web take-ups such as disclosed in Sabee, as well as two-step disturbances wherein the tension first is increased by a tension increase, and second is released over a similar period of time, such as when e.g. a turning roll vibrates at its resonance frequency.

"Sensed tension" can refer to more than one sensing cycle, and more than one location where the variable is sensed.

"Vertical velocity" means the translational velocity of the dancer roll 224 within its operating window.

Regarding a "first sensing and control system" for sensing and controlling the static forces; and a "second sensing and control system" for sensing and controlling the dynamic forces, it should be understood that the first and second sensing and control systems are not mutually exclusive. Rather, they use common sensors, and common controllers, thereby generating a combined single output control force, based on the combination of force components attributable to the respective sensing and control systems.

The above described embodiments of the dancer roll subsystem discuss the use of the dancer subsystem 152 with respect to attenuating tension disturbances in the web. In corollary use, the dancer subsystem 152 can also be used to create temporary tension disturbances. For example, in the process of incorporating the threads 112 of elastic into the web at a nip, e.g. at a nip 144 between an underlying web and an overlying web (see FIGS. 8–10 and 13), it can be advantageous to increase, or decrease, the tension of the elastic threads or elements at specific places as it is being incorporated into each garment. Thus, the dancer control subsystem 152 can effect such short-term variations in the tension in the threads. Specifically, the nip 272 in FIG. 15 corresponds to the nip 144 in FIG. 8. The web 218 in FIG. 15 corresponds with the threads 112 of thread elastic discussed with respect to FIGS. 8–10 and 13.

Accordingly, the dancer subsystem 152 can be used to decrease, and substantially eliminate, tension in the threads 112 of leg elastic being incorporated into the combined web 121 at nip 144, as the area on the webs corresponding to the crotch 24 to be made for each blank enters the nip 144.

Referring to FIG. 15, tension on the web is temporarily reduced or eliminated by inputting a force from servo motor 256 causing a sudden, temporary downward movement of the dancer roll, followed by a corresponding upward movement. Similarly, tension is temporarily increased by inputting a force from the servo motor 256 causing a sudden, temporary upward movement of the dancer roll, followed by a corresponding downward movement. Such a cycle of increasing and decreasing the tension can be repeated more than 200 times, e.g. up to 300 times per minute or more using the dancer roll subsystem 152.

For example, to reduce the tension quickly and temporarily to zero, the computer controller commands, and the servo acts, to impose a temporary downward vertical motion to the dancer roll during the short period over which the tension is to be reduced or eliminated. The distance of the sudden downward vertical movement corresponds with the amount of tension relaxation, and the duration of the relaxation. At the appropriate time, the dancer is again positively raised by the servo to correspondingly increase the web tension. By such cyclic activity, the dancer roll can routinely and intermittently impose alternating higher and lower (e.g. substantially zero) levels of tension on the web 218.

THE ELASTICS CUTTER

The following description of the elastics cutter subsystem 154, preferably including outer cover construction roll 102, is made in the context of the processing line 151 shown in FIG. 13, and the embodiment of the blank 10 illustrated in FIG. 12. Given the disclosure herein, the novel cutter subsystem 154 can be used with other methods and apparatus for cutting other discrete elements of other composite webs at discrete loci in the respective webs.

As seen in FIGS. 9–10, 12, and 20–23, and as discussed somewhat hereinabove, each thread of elastic 112 is generally fed into the nip 144 between the web 100 and one of the elements of the continuous web 106. However, as the leading edge 24A of the crotch 24 enters the nip 144, the transverse movement of lateral thread guides 122 causes the threads of leg elastic to be placed on the continuous substrate web 100 at the nip 144 at a locus disposed transverse to the respective cover web, namely between the inner edges 148, 176 of front element 19, and back element 21, of the body side layer 14, respectively, and thus not entrapped between the web 100 and the respective elements of the body side layer. After the web has progressed until the opposing, and trailing, edge 24B of the crotch is at the nip 144, movement of the thread guides 122 again causes the thread 112 to be placed on the web 100 in a locus disposed between the web 100 and the respective element of the web 106. The thread guides 122 can, and typically do, simultaneously place as many threads of elastic 112 as desired along what will become both the front and back edges 52 of the leg openings 44, 46.

Figure 20:
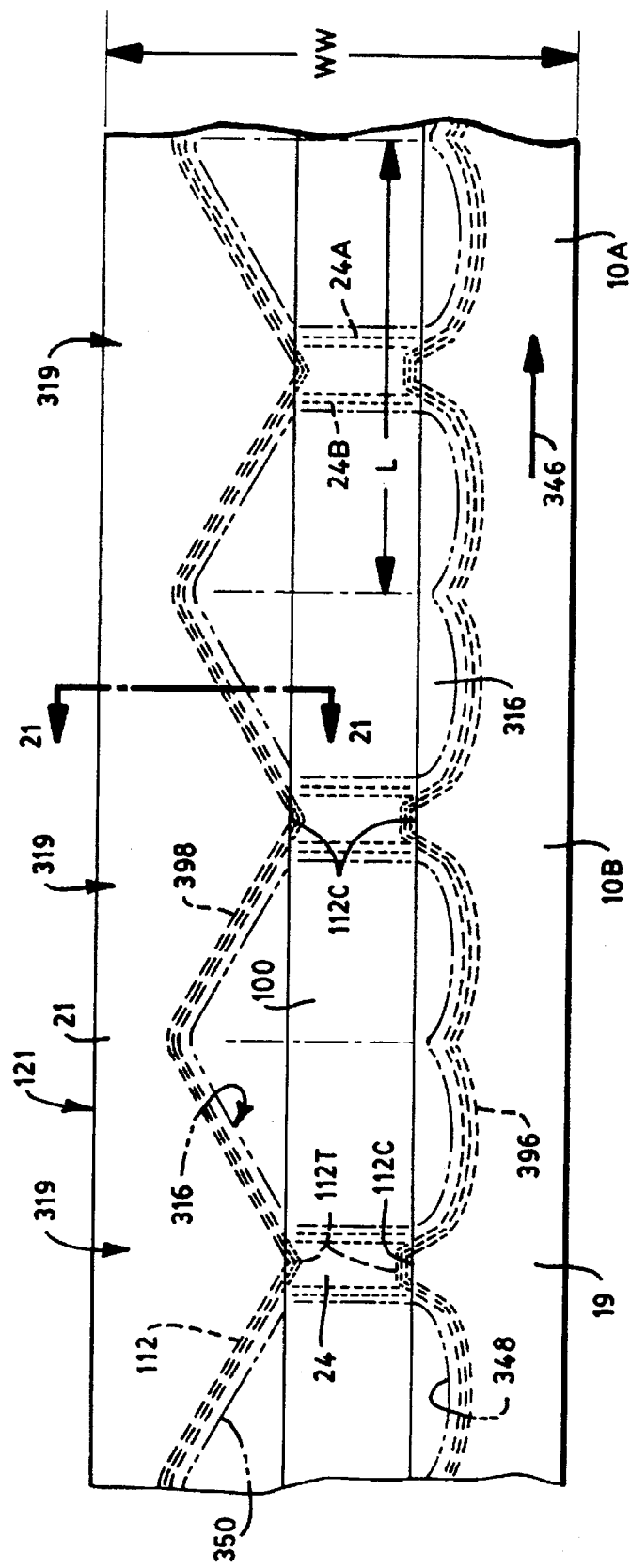
FIG. 20 is a top view of a fragment of the continuous web after the leg elastic has been incorporated into the web, showing three workpieces, comprising three garment blanks, and is taken at 20—20 of FIG. 8.

FIG. 20 shows the combined web 121, including substrate web, elements 19, and 21 of the web 106, and threads of elastic 112 in a desired pattern outlining front portion 348 and back portion 350 of the leg openings, as the combined web 121 progresses from the nip 144 of turning roll 110 and construction roll 102 toward the ultrasonic horn 342. Direction of movement of the web through the system is shown by the arrow 346. The leg openings extend from a first crotch 24 in a leading workpiece to a second crotch 24 in the next trailing workpiece, and from the front portion 348 to the back portion 350, and are generally designated 316. The leg openings 316 are cut in the blanks 10 in subsequent steps which are discussed later. Accordingly, the general outlines only of the leg openings 316 are shown in dashed representation in FIGS. 20 and 23.

As illustrated in FIG. 20, the common dashed lines labelled 112 represent the threads of elastic disposed between elements 19, 21 of the body side layer 14 and the substrate web. FIG. 21 illustrates the threads of elastic 112 as entrapped between the substrate web and the back element 21. The shorter dashed lines labelled 112T represent the paths of the threads of elastic 112 as positioned by the thread guides 112 at the nip 144. However, since the adhesive is placed on the webs 106 which become the body side layer 14, not the base web 100 prior to nip 144, and since the threads of elastic are not disposed under either element 19, 21 at the crotch, the threads of elastic are not bonded to any web across the crotch 24.

Accordingly, as soon as the threads emerge from being held under the pressure existing at the nip 144, they retract along the respective inner edges 148, 176 of the front and back elements of the body side layer 14, respectively. As a result, the threads of elastic crossing the crotch 24 between respective front portions 348, or respective back portions 350 of a leg opening, are generally bunched together along the inner edges 148, 176 of the respective elements 19, 21, as seen in FIG. 22. The threads of elastic 112 along each inner edge 148, 176 thus form a loose rope-like arrangement between the loci where the respective threads emerge from the edge of the adhesive layer 55 adjacent the leading edge 24A of the crotch and the loci where the threads re-enter the adhesive layer adjacent the trailing edge 24B of the crotch.

To the extent the side edge of the adhesive layer on an element 19 or 21 terminates short of the inner edge 148 or 176 of the respective element, the threads of elastic tend to collect under the edge of the respective web element 19 or 21, between the web element and the substrate web 100. Three of the four threads are thus shown between the substrate web and the back element 21 in FIG. 22. However, where the edge of the adhesive pattern closely approaches the inner edge of the web element 19, 21, the threads of elastic cannot all fit in the preferred orientation under the web element, whereupon they bunch up, which can include some random stacking of the threads on top of each other as shown in FIG. 22 at the inner edge 148 of the front web element 19.

FIG. 22 thus illustrates the position of the portions of the threads of elastic 112C traversing the crotch 24 of the blank just prior to being severed by ultrasonic horn 342. The portions 112C of the threads are also seen in FIG. 20. As the workpieces in the web are processed at the ultrasonic horn 342, and as discussed in more detail hereinafter, the cross-crotch elastics are severed by the ultrasonic energy applied by the ultrasonic horn to create the loose cut ends 150, illustrated in FIG. 23.

Figure 23:
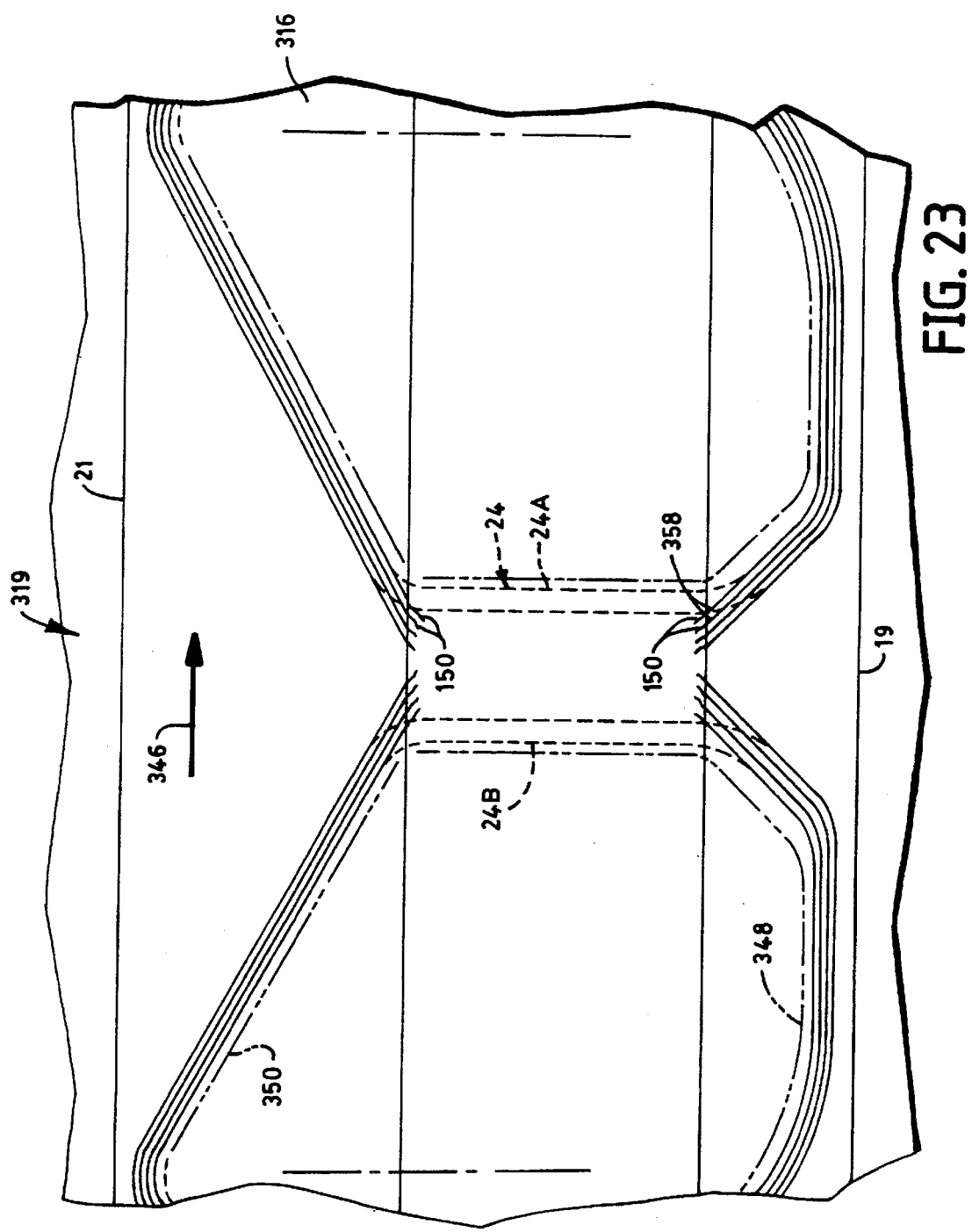
FIG. 23 is a top view of the portion of one workpiece incorporating elastic after the elastic elements have been severed at the crotch portion by ultrasonic cutting apparatus.

When the cross-crotch elastics are thus severed, each thread retracts to the locus 358 where the respective thread of elastic emerges from the edge of the adhesive layer 55, and thus the bonding action of the adhesive layer. The retracted threads, e.g. after severing, thus have free ends 150. Accordingly, as each workpiece 319 exits the severing step at ultrasonic horn 342 as illustrated in FIG. 23, the leg elastics extend, between substrate layer 100 and the corresponding web element 19 or 21, along the front and back portions 348, 350 respectively of each leg opening 316, and to each edge of the corresponding crotch 24. However, since the cross-crotch elastics have been cut at the crotch, the elastics do not extend across the crotch.

Key to success in fabricating the blank 10 is the inventors' discovery of novel apparatus and methods for controlling the amount of ultrasonic energy to be applied by the ultrasonic horn 342, and thus creating a control system for severing the at least one threads of elastic 112, the threads 112 in a sense constituting a separate layer intermediate the substrate web 100 and the respective web elements 19, 21, without cutting or otherwise significantly harming the ultimate functionality of the substrate web or the web element 19 or 21. While it is known to use ultrasonic energy to cut, or weld together, all layers/webs in a multiple layer structure, applicants teach herein apparatus and methods which enable severing the at least one threads of elastic and more preferably without severing or welding the substrate web or the respective web element 19 or 21. In an alternative method of the invention, the at least one threads of elastic are severed, and simultaneously the respective web element 19, 21 is welded to the substrate web. In a still another alternative method of this invention, the at least one thread of elastic, is severed while and simultaneously cutting the respective web element 19, 21 of the substrate without significantly harming the functionality of the substrate web.

Up to this point, the discussion of the elastics cutter has focused on the results achieved by using the apparatus and methods of the invention. Following is a more specific discussion of the preferred embodiments of specific apparatus and methods used to achieve the desired cutting results.

Figure 25:
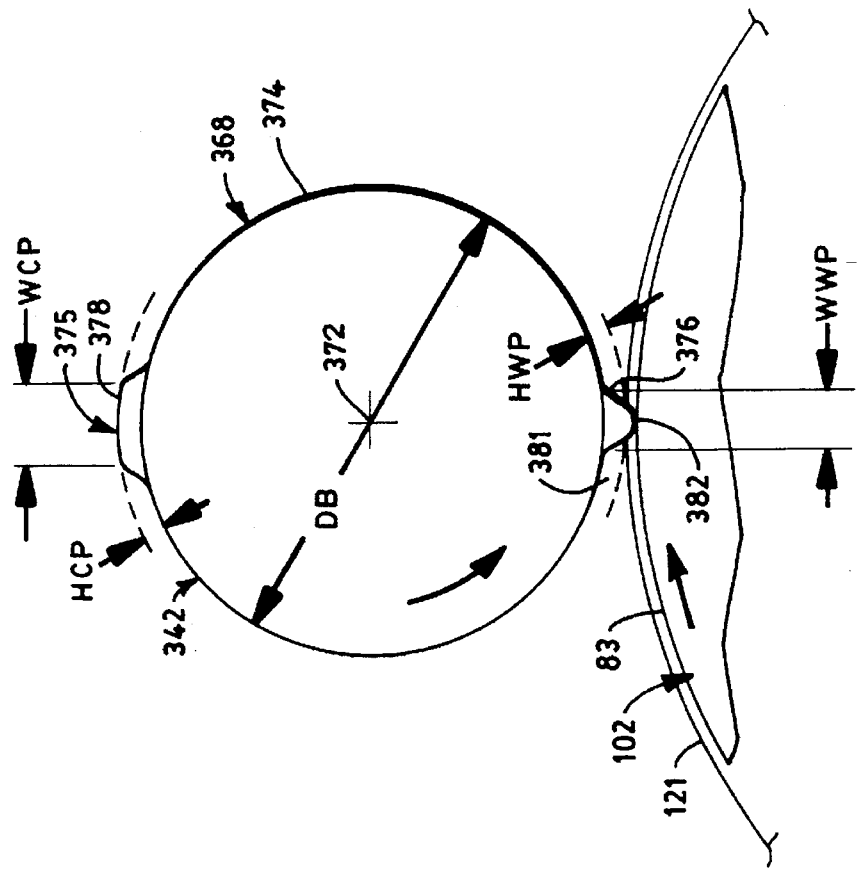
FIG. 25 is a cross-section of the ultrasonic horn taken at 25—25 of FIG. 24, with addition of representative section of the respective anvil roll.
Figure 24:
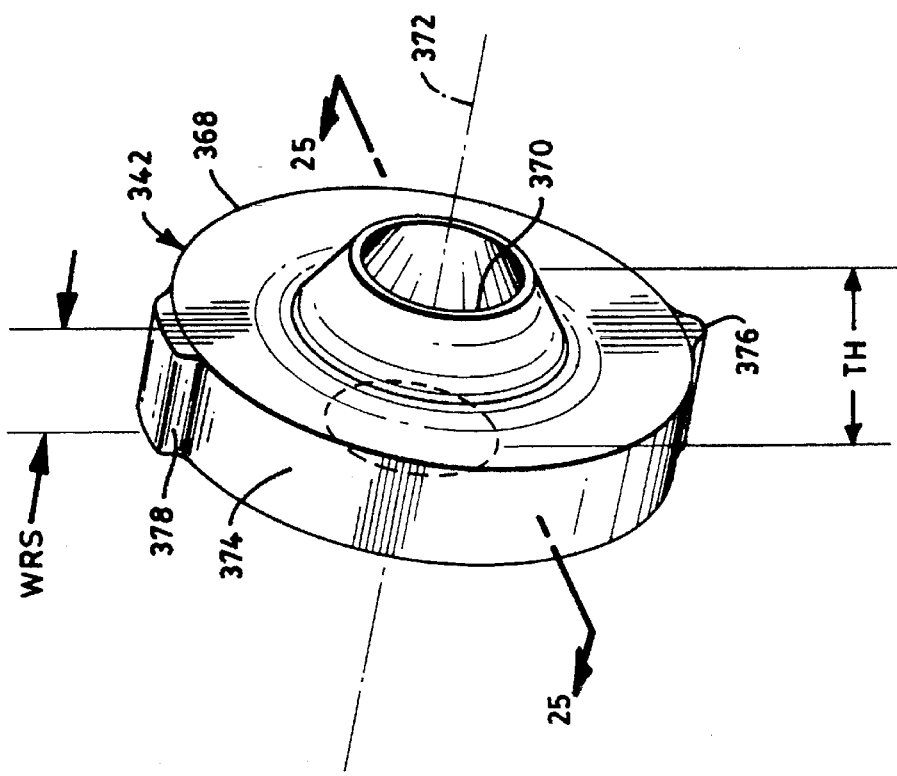
FIG. 24 is a perspective view of a novel ultrasonic horn.

Referring now to FIGS. 24 and 25, a suitable ultrasonic horn 342 is a rotary ultrasonic horn such as that taught in U.S. Pat. No. 5,110,403 to Ehlert, modified as discussed hereinafter. U.S. Pat. No. 5,110,403 is herein incorporated by reference for its teaching of the general structure and general use of such rotary ultrasonic horn.

The rotary ultrasonic horn 342 incorporates the rotary horn taught in U.S. Pat. No. 5,110,403 as an inner core member 368. The inner core member 368 thus includes a hub area 370, an axis of rotation 372 extending through the hub area, an overall thickness "TH," a base diameter "DB," and an outer radial surface 374. The center of gravity of inner core member 368 is disposed at, and generally corresponds with, the axis of rotation 372.

Rotary ultrasonic horn 342 further comprises an activating member 375, including a working protuberance 376 and a counterbalancing protuberance 378. Referring now especially to FIG. 25, the protuberances 376 and 378 are shown with stippled shading in order to highlight their presence. In addition, the outline of a phantom (non-existent in that location) working protuberance is shown in dashed outline superposed on the counterbalancing protuberance 378 in order to show the comparative differences in the structures of the two protuberances, and the comparative cooperations between the protuberances and the underlying anvil roll construction roll 102, which operates as an anvil roll with respect to the ultrasonic horn 342.

The purpose of the working protuberance 376 is to perform the work of selectively severing the elastic threads at the crotch portions, while, only as desired, at the same time forming welds or cuts in the web element 19 or 21 and/or the substrate web 100.

By comparison, the purpose of the counterbalancing protuberance is to provide a mass that counterbalances the mass of the working protuberance. Preferably, the counterbalancing protuberance is effective to project the center of gravity of the combination of working protuberance and counterbalancing protuberance (e.g. activating member 375) onto the axis of rotation 372, preferably superposed on the center of gravity of the inner core member 368, thus maintaining the center of gravity of the horn at the axis of rotation.

As shown in FIG. 24, the counterbalancing protuberance 378 generally extends along the entire width "WRS" of the radial surface. Similarly, the working protuberance also typically extends along the entire width "WRS" of the radial surface.

Working protuberance 376 has a first height "HWP" and a first width "WWP." Counterbalancing protuberance 378 has a second height "HCP" and a second width "WCP." As a general principle, the height "HCP" of the counterbalancing protuberance 378 is less than the height "HWP" of the working protuberance 376.

The specific height and width of the working protuberance, and its corresponding counterbalancing protuberance, vary according to the working environment in which the activating member will be used. Applicants have experimented with the invention using substrate web 100 and web elements 19, 21 at 0.7 ounce per square yard each, spunbonded polypropylene. The elastic was Lycra® elastic threads at 940 decitex. The inner core member 368 of the rotary ultrasonic horn used was about 6 inches in diameter. Given those working conditions, the working protuberance has preferred height "HWP" of 3/16 inch, and had a preferred width "WWP" of 3/16 inch. A preferred range of heights "HWP" for this working environment is about 0.13 inch to about 0.25 inch. A preferred range of widths "WWP" for this working environment is also about 0.13 inch to about 0.25 inch.

The preferred height "HCP" of the counterbalancing protuberance 378 depends on the height "HWP" of the corresponding working protuberance, with the height "HCP" preferably being about half the height of the working protuberance. Accordingly, in the above working environment, and given a height of 3/16 (0.188 inch) for "HWP," the preferred height "HCP" for the counterbalancing protuberance is about 3/32 (0.094) inch.

Once the height of the counterbalancing protuberance has been determined, the width "WCP" of the counterbalancing protuberance is preferably determined by calculating the width necessary to provide the mass required to counterbalance the mass of the working protuberance, and thereby position the center of gravity of the combination of the spaced working protuberance and counterbalancing protuberance (e.g. the activating member 375) on the axis of rotation 372. Where, for example, the height "HCP" of the counterbalancing protuberance is about half the height of the working protuberance, the width "WCP" is about twice the width "WWP" of the working protuberance.

The working protuberance and the counterbalancing protuberance each preferably have a length, and substantially uniform cross-section, extending the full width "WRS" of the outer radial surface 374, which length is, as shown in FIG. 22, substantially less than the overall length of the construction roll 102 between its opposing ends. The working protuberance can be shorter than the width "WRS." However, it generally is not longer than the width of the outer radial surface. Similarly, the counterbalancing protuberance can be shorter than the width of the radial surface, as desired, so long as the mass balance is achieved, the center of gravity is disposed on the axis of rotation, and the height objectives are met.

The significance of the center of gravity being on the axis of rotation is generally two-fold. First, such properly positioned center of gravity assists in maintaining the mechanical rotational stability of the horn as it rotates about its axis 372. Second, maintaining the center of gravity at the same locus as that of the inner core member 368 generally contributes to the ultrasonic efficiency of the horn wherein the inner core member 368 alone was designed for efficient transfer of ultrasonic energy.

Referring now to FIG. 25, in the example illustrated herein, the outer radial surface 374 of horn 342 has a width "WRS" of about 2 inches. In the embodiments illustrated, the outer radial surface is biased against the construction roll 102 with a force of e.g. 10–100 pounds across the 2-inch width "WRS," and against an absolute stop 380 (see FIG. 26) set to provide zero clearance, and thus to provide a nip 382 between the horn 342 and the construction roll 102, when the working protuberance 376 is rotated against the construction roll 102 as shown in FIG. 25. The biasing force is somewhat dependent on the working environment, including the structure of the workpieces 319. Accordingly, the above-recited force is not limiting, and is intended to be illustrative only.

Figure 26:
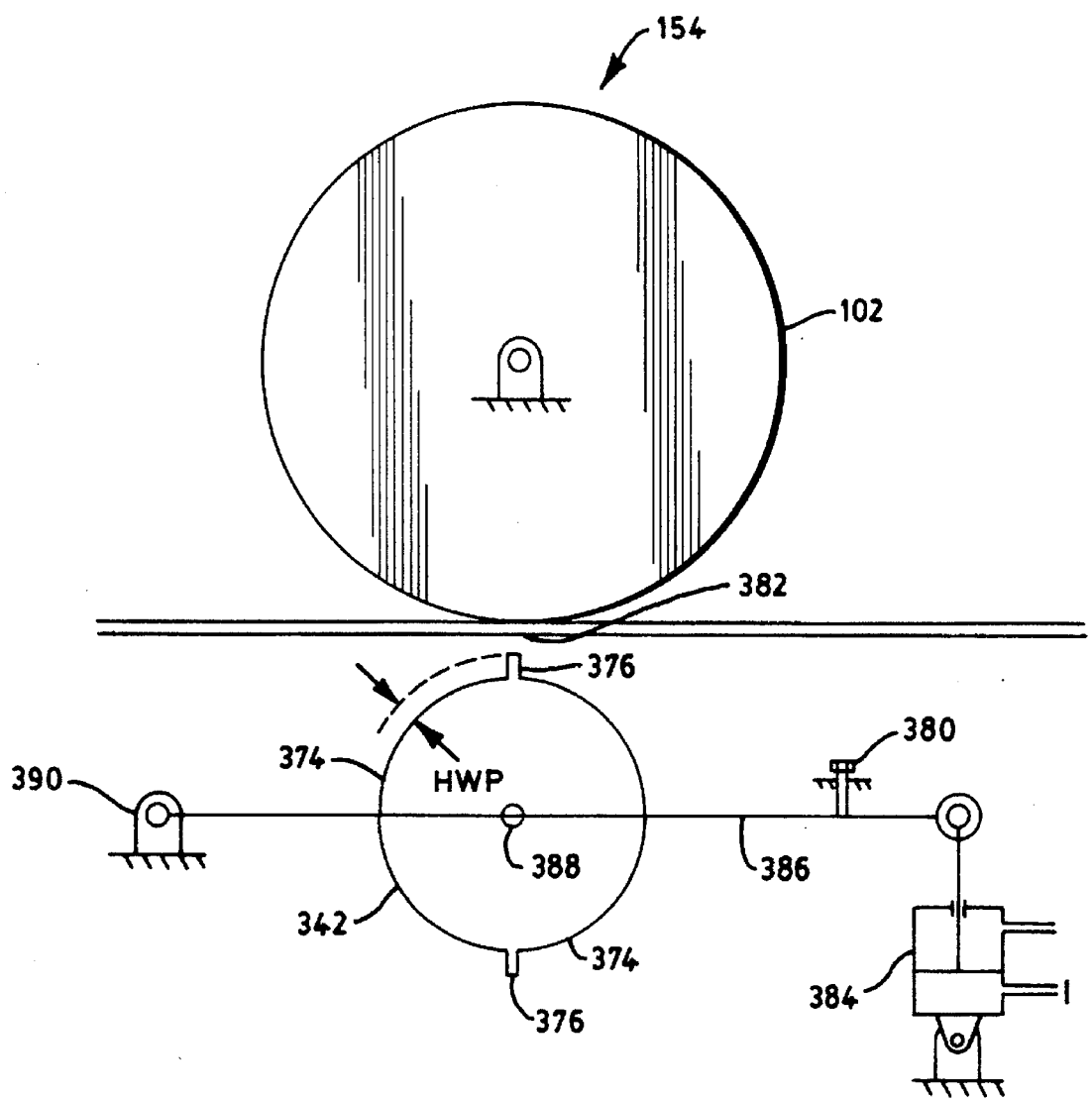
FIG. 26 is a side elevation of another embodiment of suitable ultrasonic apparatus, showing apparatus for controlling nip engagement and nip pressures.

As illustrated by the combined showings of FIGS. 25 and 26, the absolute stop 380 spaces the outer radial surface of the construction roll or horn carrying the working protuberance from the other element of activating member 375, whereby a gap 381 is maintained between the radial outer surface of the horn and the corresponding outer surface 383 of the construction, or anvil, roll, whereby the outer radial surface 374 never comes into contact with the construction roll 102; nor does the outer radial surface 374 exert any force against the combined web 121.

Similarly, the counterbalancing protuberance 378, when it approaches the area of nip 382, is spaced from the construction roll by a distance corresponding to "HWP" minus "HCP," whereby the counterbalancing protuberance never comes into contact with, or exerts force on, the construction roll 102.

So long as the thickness of the combined web 121 is less than the clearance between the counterbalancing protuberance and the corresponding construction/anvil roll 102, the counterbalancing protuberance does not exert any force on the combined web 121. Where web thickness is greater than the clearance between the counterbalancing protuberance and the anvil roll, a substitute horn may be used, wherein the clearance between the anvil roll and the counterbalancing protuberance is greater than the thickness of the combined web 121.

In general, then, the working protuberance 376 rotates with the rotation of the rotary construction roll 102, thus temporarily closing the nip 382 once during each rotation of the horn 342, for a period corresponding to the time required for the working protuberance to traverse the nip 382. The time "x" in seconds required for the working protuberance to transverse the nip is given by the equation $$x=(WWP/L)*T$$

where

L=Length of each workpiece, measured in the with machine direction

T=Time in seconds for each workpiece to pass a given point in the process line.

For example, assuming a length "L" of 30 inches for each workpiece 319, a line speed of 10 products per minute (thus 6 seconds for each workpiece to pass any given point in the process line), and a width "WWP" of the working protuberance of 3/16 inch, the working protuberance traverses the nip 382, and is in working contact with each workpiece for 0.0375 seconds. Using the same equation, one can calculate the following relationships:

| Contact Time Seconds | Workpieces Per Min. | Workpiece Length, Inches |
| --- | --- | --- |
| .0375 | 10 | 30 |
| .0038 | 100 | 30 |
| .0012 | 300 | 30 |
| .0006 | 600 | 30 |
| .0469 | 10 | 24 |
| .0047 | 100 | 24 |
| .0016 | 300 | 24 |
| .0008 | 600 | 24 |

In general, preferred dwell time corresponding to the time required for the working protuberance to traverse the nip 382 is between about 0.0005 second to about 0.2 second.

When the working protuberance 376 comes into contact with the combined web 121, and given the zero clearance setting of absolute stop 380, the thickness of the combined web 121 pushes the horn 342 and the construction roll 102 apart against pressure being applied on the horn or construction roll at nip 382. Referring to FIG. 26, a two way cylinder 384, pneumatic or hydraulic, applies an upward force on the corresponding anvil roll 328, through a rigid lever arm bar 386 secured to the shaft 388 on anvil roll 328, which corresponds with the axis of rotation of the anvil roll 328. Rigid bar is secured to ground at fulcrum 390. In the inventors' working examples, using e.g. 0.7 osy spunbonded polypropylene webs and 940 decitex lycra, a nip pressure ranging from about 500 newtons per meter of linear contact, to about 9000 newtons per meter, is preferred.

Further to the operation of the ultrasonic horn, the amplitude of the horn vibrations is related to the structure and materials of each specific horn. Given a horn having an inner core member 368 structurally constructed as disclosed in U.S. Pat. No. 5,110,403 Ehlert, about six inches diameter, 2 inches width "WRS," of the outer radial surface, using a tungsten alloy composition, a horn amplitude of about 0.025 millimeter to about 0.075 millimeter is typical. By increasing power input to the horn, amplitude can be increased somewhat to about 0.055 millimeter. But again, the amplitude range is generally limited by the structure of the horn used.

To control the amount of ultrasonic energy applied by the horn, one controls the combined factors of nip pressure, e.g. at nip 382, amplitude of the horn vibration, and the time for which the horn is in contact with the combined web 121. An increase in any one of the parameters, nip pressure, amplitude of horn vibration, and time of contact, increases the amount of energy applied.

As the amount of energy applied increases, so does the response of the materials in combined web 121. As minimal energy is applied, the ultrasonic apparatus may have no effect on the web. As the amount of energy input into the web at horn 342 is increased incrementally, the energy will eventually become large enough to sever the threads of elastic 112 while leaving only modest mark, if any, on a respective web 100, 19, or 21. As the energy input is increased further, the ultrasonic energy cuts the threads of elastic 112, and in the same operation forms a weld (not shown) between the substrate web 100 and the respective web element 19, 21. If the amount of energy is further increased to a range above that preferred in this invention, the threads 112 are severed, along with cutting of substrate web 100 and the respective web element 19, 21. Those skilled in the art will recognize that the specific parameters for achieving the above described levels of work depend on the apparatus used, the power inputted to the apparatus, and the characteristics of the combined web 121 being processed. Suitable ultrasonic generators are, of course, available from, for example, Branson Sonic Power Company, Danbury, Conn.

While FIGS. 24 and 25 show one working protuberance and one counterbalancing protuberance, one can use more of each, as desired, with preference that the mass balance essentially maintains the center of gravity at the axis of rotation 374. Accordingly, two working protuberances can be used wherein the second working protuberance replaces, and obviates the need for, counterbalancing protuberance 378. The speed of rotation of the horn 342 is adjusted accordingly so that two workpieces 319 pass the horn for each rotation of horn 342.

The surface speed of the working protuberance 376 when in contact with the combined web 121 should match, preferably within about 10%, the surface speed of the combined web 121. However, in order that the working protuberance not operate on other areas of the web, the horn must advance rotationally only one, and exactly one, working protuberance while the combined web 121 advances by the length of one workpiece. Since the circumference of the 6 inch diameter horn used as an example has a circumference of about 18 inches, since sizing of the horn is critical to its ultrasonic resonance capability, and since the garment blank in this particular design is typically 24–30 inches long at garment length "L," the surface speed of the horn is preferably reduced to below the constant surface speed of the combined web 121 while the horn is out of contact with the web. Accordingly, the speed of rotation of the horn is increased as the crotch 24 of a blank approaches the horn 342, matches the surface speed of web 121 as the working protuberance applies ultrasonic energy to the web 121 at crotch 24, and then is decreased after the crotch has passed the horn.

One conventional method of controlling the rotational speed of the horn 342 is a servo motor (not shown). A preferred method of controlling the speed of rotation of the horn is to use a set of noncircular drive gears 392, 394, shown illustratively in FIG. 8. A full disclosure of the structure and operation of such noncircular drive gears, to vary the speed of the driven device is given in copending application Ser. No. 08/186,352, filed Jan. 25, 1994, herein incorporated by reference for its teaching of structure and use of noncircular gears.

It should be noted for completeness that a separate horn 342 is used at each inner edge 148, 176 of the respective web elements 19 and 21, as shown in FIG. 22.

Figure 27:
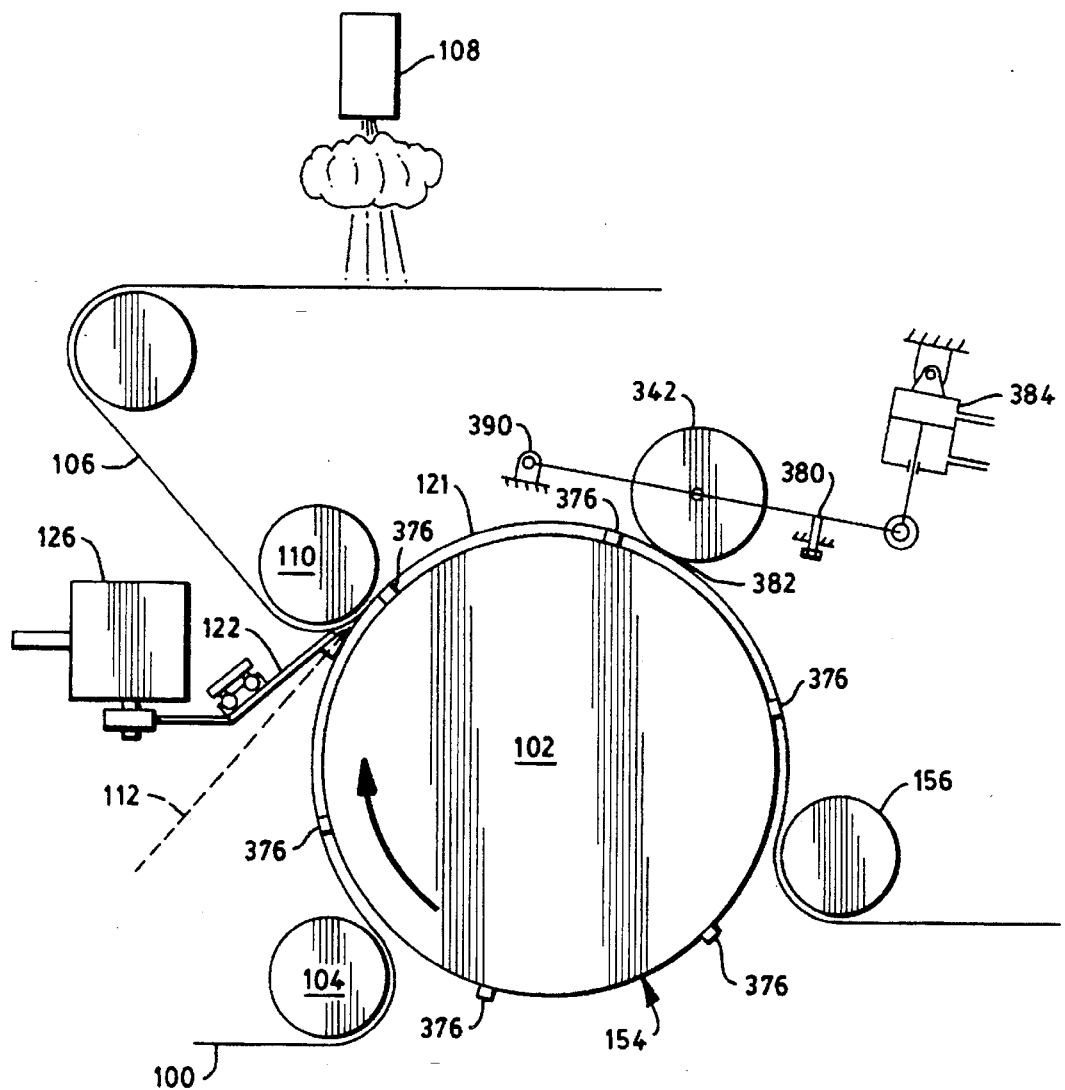
FIG. 27 is a side elevation showing still another embodiment of the ultrasonics subsystem.

The disclosure so far with respect to cutting the crotch elastic, has focused on one or more working protuberances, disposed on the ultrasonic horn 342. FIGS. 26 and 27 illustrate that the working protuberances can, in the alternative, be disposed on the functional anvil, whereupon a conventional ultrasonic horn e.g. as taught in U.S. Pat. No. 5,110,403 Ehlert can be used without modification. Referring to FIG. 27, a plurality of working protuberances 376 are disposed on outer surface 383 about the circumference of the otherwise conventional anvil roll 328, one working protuberance per repeat length of the product blanks being processed. A conventional rotating ultrasonic horn 342 is used to transfer ultrasonic energy to the web against the protuberances. Again, the absolute stop 380 is set for zero clearance between the horn and the anvil roll at each working protuberance 376. Accordingly, when the horn is not working against a protuberance 376, no pressure is exerted on the web 121, whereby minimal if any energy is transmitted from the horn 342 to the web between working protuberances.

FIG. 26 is relied on first to show the pneumatic or hydraulic cylinder applying pressure to the nip 382, against absolute stop 380, using the lever bar 386, for all embodiments illustrated. FIG. 26 shows the pressure being applied to an anvil roll carrying the working protuberances. The pressure could, in the alternative, be applied at the rotary ultrasonic horn 342.

FIG. 26 further illustrates an anvil roll 328, smaller than the ultrasonic horn 342, and carrying the working protuberances 376, whereby relative size of the horn and anvil, as well as the selection of which of the horn and anvil is to carry the working protuberance, is now a design choice.

As seen in FIGS. 26 and 27, where two or more working protuberances 376 are uniformly spaced about the circumference of the horn 342, or the anvil roll 328, no counterbalancing protuberance 378 is needed.

It is contemplated that the operation and functions of the cutter 154 have become fully apparent from the foregoing description of elements, but for completeness of disclosure, the usage of the cutter will be briefly described with respect to the embodiment illustrated in FIGS. 8, 24, and 25.

Substrate web 100 is drawn into the processing elements shown, by the driving force on turning roll 104 against rotating construction roll 102, and advances on the construction roll 102 to the nip 144. At the same time, the webs 106 are drawn into the processing elements shown, by the driving force of turning roll 110 at nip 144, passing first under adhesive spray 108. The adhesive spray is directed to cover the entire surfaces of webs 106, with exception of the edges in order to avoid adhesive overspray.

Threads of elastic are drawn into the nip 144 through thread guides 122. Guides 122 move transversely with respect to the machine direction of the advance of the webs 100 and 106 along the processing operation, in order to create the patterned paths 396 and 398 of the threads of elastic along the front and back portions 348, 350 of the leg openings 316 (shown in FIG. 20).

The webs 106 are bonded to the substrate web 100 through the pressure at nip 144 in combination with the action of the adhesive layer 55, thus trapping the threads of elastic 112 between the substrate layer 100 and the respective web elements 19, 21, except at the crotch 24 of each blank 10.

At each crotch 24, the threads of elastic 112 emerge from the edges of the adhesive layer 55, and cross the crotch portion along the inner edges 148 and 176 of the respective front and back elements of the body side layer 14. The portions of the threads of elastic 112C which cross the crotch 24 of the respective blanks 10 are severed by ultrasonic energy at sonic horn 342, without cutting the substrate web 100 or the respective web element 19 or 21. However, the substrate web and web elements could be severed by increasing the effective amount of power delivered to the combined web 121 e.g. by increasing horn amplitude, contact time, and/or pressure at nip 382. The web, thus containing the so processed workpieces, leaves the construction roll 102 at turning roll 156.

While choosing not to be bound by any particular theory, the inventors believe that the discrete nature of the elastic threads, and perhaps the fact that their diameters differ from the general thickness of the webs 100 and 106, may cause the threads 112 to concentrate the ultrasonic energy such that the threads respond to the ultrasonic energy before the base web or the cover webs respond. Thus, by limiting the amount of energy transmitted to the combined web 121, the effect is limited to that portion of the web (the threads of elastic) which responds first or, as desired, to a combination of severing the threads of elastic and forming a weld between substrate web 100 and the corresponding web element 19 or 21.

CONTROLLING SHRINKAGE OF WEB WIDTH

In the blanks 10 shown, front leg elastic elements 50, crotch elastic elements 51, and back elastic elements 48 are disposed, in a stretched condition in the combined web 121, adjacent the edges of the respective leg openings 316 (the composite of leg openings 44, 46), with the respective stretched elastic elements oriented in directions generally following the contours of the edges of the leg openings 316. Each of such elastic elements 48, 50, and 51 includes one or more segments which extends in a direction transversely across the width dimension "WW" of the web (FIG. 20) which corresponds with the length dimension "L1" (FIG. 1) of the combined web 121 (cross machine direction, or CMD). Such stretched elements, by nature, exert retracting forces active in the cross machine direction and urge effective reduction in the width "WW" of the web 121.

FIGS. 13, and 28–30 illustrate one embodiment of the apparatus and methods of the invention. Referring now to FIG. 13, the substrate web 100 enters the processing line at the turning roll 104, passing under the turning roll 104 and thence into a nip between a second roll 110 and construction roll 102. Second web elements 106 are joined with the substrate web 100, and elastic threads 112 are incorporated into the combined web 121 in stretched condition, in the positions they ultimately occupy in blank 10 and garment 25. Typically, the elastic elements are stretched about 100% to about 300% at the time they are incorporated into the web 121 as it is being formed from substrate web 100 and webs 106.

From the elastic construction roll 102, the web 121 passes under a turning roll 156 and onto the surface of assembly roll 158. As indicated herein, work is done on web 121 at one or more work stations on the assembly roll 158 in serial fashion along the generally endless length of web 121, such that a series of blanks 10, or blank pre-forms, are fabricated in the web 121, one following the other, generally as shown at 10A and 10B in FIGS. 1 and 20.

From assembly roll 158, the web 121 passes under turning roll 160, and between turning roll 160 and cutter roll 162, such that roll 160 acts as an anvil roll with respect to cutter roll 162. From roll 160, web 121 passes over turning roll 162 and on to the folding station 166.

Still referring to FIG. 13, the elastic elements 48, 50, 51 exert retractive forces in the web 121, in the cross machine direction, beginning at the outer cover construction roll 102, and all along the web for the remainder of the length of the portion of the processing system illustrated in FIG. 13, including through the several work stations. Work performed at various work stations, and at e.g. anvil roll 160, requires registration of each blank pre-form with the working elements at the respective work station. Accordingly, it is important that the web dimensions be stable, both the length dimension of the web and the width dimension of the web, from nip 144 where the transversely oriented elastics are incorporated into the web, through the remainder of the downstream processing operations illustrated in FIG. 13, through cutter roll 174.

Referring to FIGS. 28–30, the outer circumference of the assembly roll 158 generally includes a substrate 444 which extends entirely about the circumference of the assembly roll, and along the entire length "L8" of the roll, which corresponds generally with the width "WW" of the web 121.

A first coating 446 comprising rubber or like resilient material extends entirely about the circumference of the assembly roll 158 and along only a central portion "LC" of the length of the roll.

A second coating 448 has a composition incorporating primarily metallic elements. Coating 448 extends entirely about the circumference of the construction roll, and along first and second portions "LE1" and "LE2" of the length "L8" of the assembly roll, adjacent the first and second ends 450 and 452 of the roll.

Referring to FIGS. 28 and 29, a series of suction ports 454 communicate suction from inside the assembly roll 158, urging the web 121 firmly against the composite of the outer working surface 456 of the roll 158, the composite of the outer working surface including the coatings 446 and 448, as well as uncoated portions 449 of the outer surface of the substrate 444.

Referring to FIG. 30, the second coating 448 is preferably applied as a generally metallic composition, by plasma or other high temperature application process. For example, coating 448 may be applied as a plasma spray, or using an electric arc medium. Such coatings are available from Plasma Coatings Inc., Waterbury, Conn. A preferred such coating for the at least circumferential portions of the working surfaces of such rolls as rolls 102, 156, 158, and 160 is available from Plasma Coatings Inc. under the designation of product number 936.

Using the application processes above mentioned, the resulting coating 448 is characterized by an irregular surface texture, including protuberances 458 spaced about the coating surface at random, though closely spaced, locations. Depending on the method of application used, and the exact composition used, the surface of coating 448 may resemble the working surface of conventional sandpaper. In some applications, as in the instant application to holding a continuous web dimensionally stable during transfer from one roll to another, the surface of the coating 448 need not be so aggressive, and so appears more like the working surface of dull, or used, sandpaper.

In combination with the protuberances 458, the surface of coating 448 correspondingly includes valleys 460 about the respective protuberances.

The exact nature of any particular metal-based coating 448 depends somewhat on the composition used, and the method of applying it. Accordingly, the protuberances of the applied coating may be characterized as quite aggressive, like fresh sandpaper, or may be more muted, like used sandpaper. The coating 448 may incorporate therein one or more release agents, such as polytetrafluoroethylene, commonly sold under the trade name Teflon®.

In the application at hand, the web 100, as it enters the process depicted at turning roll 104, can be generally represented as a conventional porous spunbonded polypropylene nonwoven, 0.7 ounces per square yard, having a generally entangled matt of polypropylene fibers. Additional layers of like material may be added to the web 100, as webs 106 added at nip 144.

FIG. 30 illustrates that, as the combined web 121 is urged against coating 448, e.g. by normal tension in the web or by suction drawn by the respective rolls 102, 156, 158, or 160, the protuberances 458 project into the web at existing openings in the spunbonded web between the fibers. As the protuberances enter the web under the urging of suction or the longitudinal tension in the web, they expand existing spaces between the fibers, to create a first set of expanded openings 462 having edges, with fiber elements of the web being disposed at those edges, in engagement with the protuberances.

While protuberances 458 may extend entirely through the web, such is generally not the case and is not necessary. By extending substantially into the thickness "T" of the web as shown in FIG. 30, the protuberances engage the fibers of the web about generally the entire portion of the area of the web which overlies the area coated with coating 448, with sufficient engagement that the web is held dimensionally stable, against especially the retractive forces of the elastic as applied in the cross machine direction. As seen in FIG. 28, the coating 448 extends to the ends 450 and 452 of the assembly roll 158, such that the edges 464 of the web 121 are underlain with coating 448. Correspondingly, the respective protuberances 458 underlying the web at or closely adjacent edges 464 engage the web at even the outer extremities of edges 464, thereby to hold the web dimensionally stable against the width dimension retractive forces being exerted by the elastic elements 48, 50, 51, even at edges 464.

Figure 31:
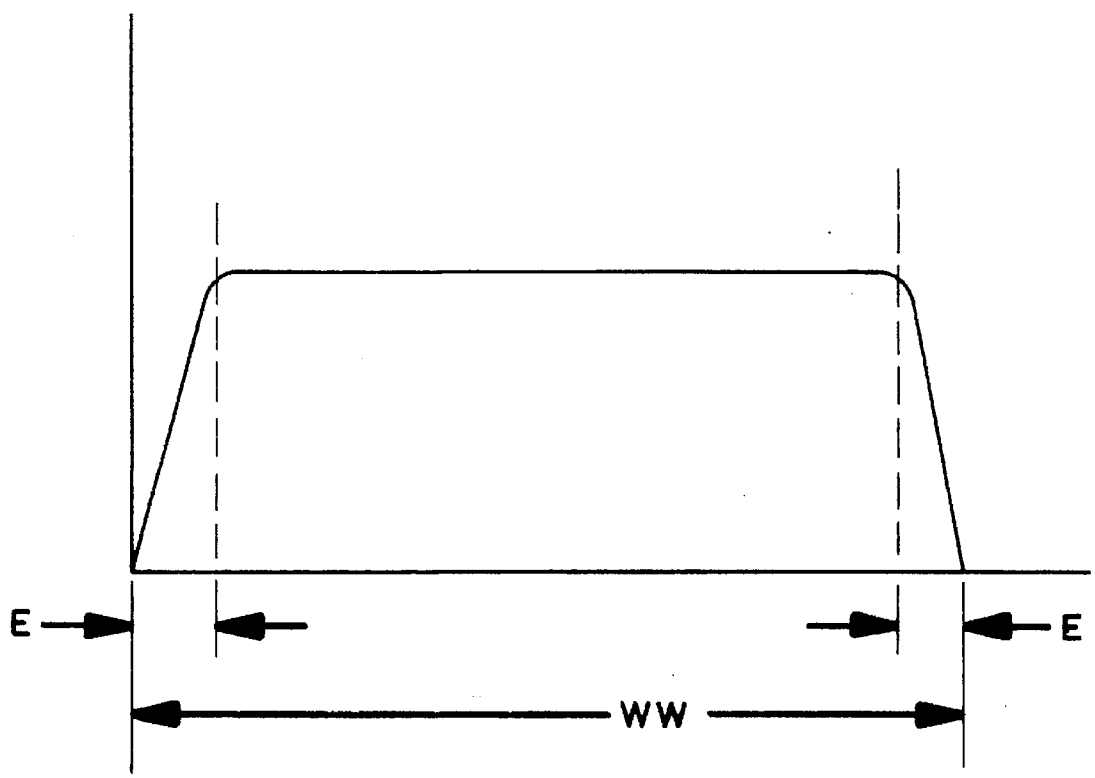
FIG. 31 is a graphical representation of the effective downward force on the web across the width of the web.

FIG. 31 represents the effective downward pressure on a web across its width "WW," and therefore the effective ability of that downward pressure to hold the web dimensionally stable against lateral forces in the web tending to destabilize the web in the width dimension.

At each edge 464 of the web, the net downward pressure on the web goes from a general maximum pressure, represented by the flat portion of the curve across the middle of the width "WW," to zero at the outer extremities of the web. The transition from the general maximum pressure to zero pressure is represented as the transition zone labelled "E."

The width of the transition zone "E" depends on the ability of the coating 448, in combination with the suction if any, to immobilize the edges 464 of the web in the width, or CMD, dimension of the web. Using the specific coating 448 described above, with the web described above, in combination with suction of 0 to about 80 inches of water, preferably about 5 to about 15 inches, more preferably about 10 inches of water, the reduction in width associated with the transition zone is limited to about 5%. If a less aggressive coating 448 is used, or if the suction is reduced, the reduction in width associated with the transition zones increases, to the point where, without use of coating 448, the reduction in width is generally substantially greater than 5%.

In the portion of the processing line shown, all rolls which transport the web after the elastics 48, 50, 51 have been incorporated in the web preferably have a coating 448 effective to maintain the CMD dimensional stability in the web while the web is being transported on the respective roll. All rolls also preferably include suction to assist the coating 448 in holding the web. Thus at least rolls 102, 156, 158, 160, and 164 preferably have a coating 448.

The web can be effectively held without any use of suction. However, a modest increase in reduction in width is experienced where suction is not used, whereby use of suction on each of the rolls is preferred.

In addition, the inventors have found that the web can traverse a gap such as at 466 between rolls while still maintaining the dimensional stability of the web, so long as both rolls incorporate a coating 448 suitable to engage especially the edges 464 of the web. By contrast, the rolls can also be satisfactorily engaged at a conventional nip (as opposed to a gap), with corresponding conventional amounts of pressure for e.g. transferring the web 121 from one roll to another.

Since the protuberances 458 are randomly spaced in the coating 448, the coating on each roll engages its own unique set of existing openings in the web 121 to thereby create its own set of expanded openings 462 while engaged with the fibers of the web.

While not absolutely necessary, the effectiveness of maintaining dimensional stability in the web is somewhat enhanced where the outer working surfaces 456 of respective rolls transferring and receiving the web are aligned with each other across the entire width of the web.

The inventors have found that by using a coating 448 including polytetrafluoroethylene in its composition, adhesive and the like normally aggressively adhering materials can be easily cleaned from the surface of coating 448 without sacrificing the ability of the coating 448 to hold the web 121 and thereby to maintain the dimensional stability of the web.

It is contemplated that the operation and functions of the coated transport roll system have become fully apparent from the foregoing description of elements, but for completeness of disclosure, the usage of the assemblage of coated rolls will be briefly described.

A web 100 enters the processing operation illustrated in FIG. 13 at turning roll 104, and is pressed against the construction roll 102 by roll 110 at nip 144. As the web is transported on roll 102, threads of elastic 112 are incorporated into the web at locations properly positioned to provide the elastic properties desired in the finished product, namely the garment article 25. Additional webs 106 are also incorporated into the assemblage at nip 144, to make the combined web 121.

Once the elastics have been incorporated in the web on roll 102, the web includes elements having retracting forces active in the cross machine direction and urging effective reduction in the width of the web.

From the outer cover construction roll 102, the web 121 is transferred to turning roll 156, and from turning roll 156 to assembly roll 158. On assembly roll 158, further work is done on the web at one or more work stations. From assembly roll 158, the web is transferred to turning roll 160. Leg openings 316 are cut by cutter roll 162, against roll 160 which serves as the anvil for the cutting operation. The web 121 then passes over turning roll 164, and passes on to the folder 166.

PLACING THE CROTCH ELASTIC

This portion of the invention describes the crotch elastics application subsystem 159. This subsystem provides methods and apparatus for receiving crotch elastics material travelling at a first speed, stretching the elastics material or maintaining existing stretch in the material, as appropriate (such as already stretched materials and latent elastic materials), and transferring the material to the substrate web 100 in stretched condition, the substrate web travelling at a second speed.

The methods and apparatus disclosed here can also be particularly useful for receiving parts of elastic material, such as leg or waist elastic, and transferring the parts to other products such as, for example, a disposable diaper or other incontinence product. In light of the disclosure herein, it is readily apparent that the methods and apparatus would be suitable for applying any part to any suitable receiver.

Referring to the drawings relating to the specifics of placing the crotch elastics, FIGS. 32–38 describe background concepts related to placing the crotch elastics 51; while FIGS. 39–47 disclose a specific representative example of apparatus and methods which can be used for placing the crotch elastics 51 as illustrated in the blank 10 of FIG. 1.

Figure 32:
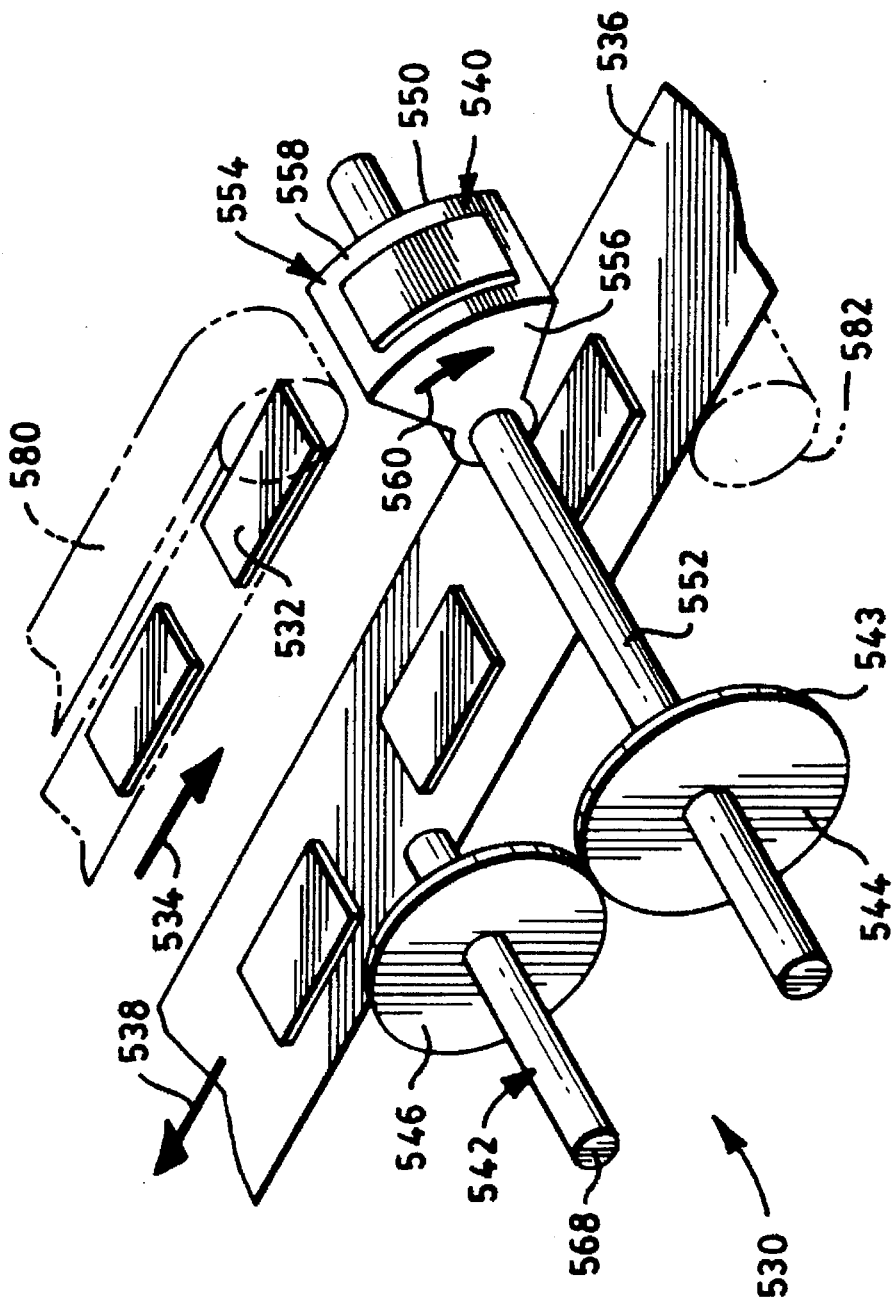
FIG. 32 representatively shows a pictorial view of one example of apparatus of the type used to place the crotch elastic.
Figure 33:
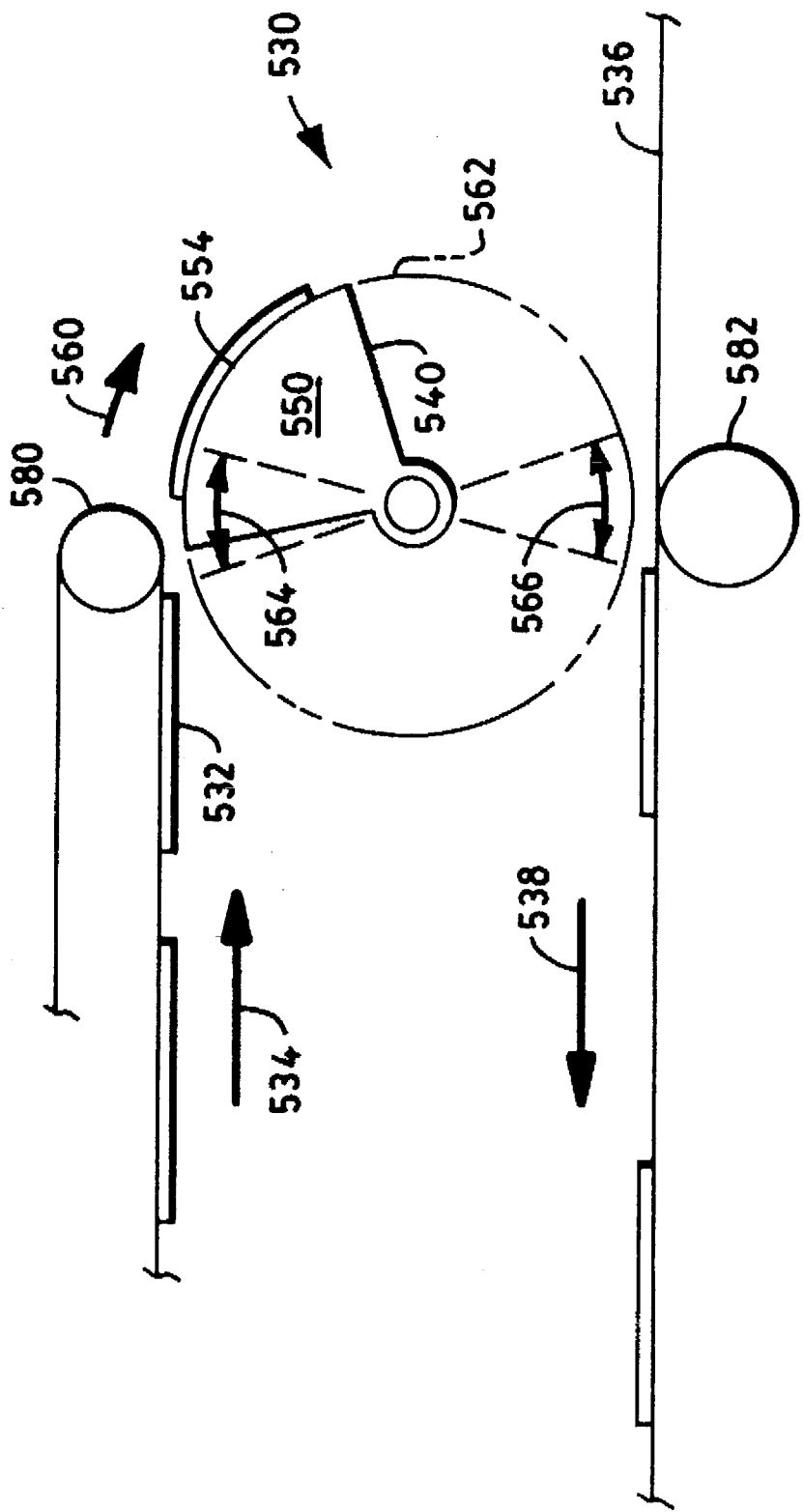
FIG. 33 representatively shows a schematic side view in elevation of the apparatus of FIG. 32.

Referring now to FIGS. 32 and 33, there is representatively shown an aspect of the invention wherein apparatus generally indicated at 530 receives discrete parts 532 travelling at a first speed in the direction indicated by the arrow 534 associated therewith and applies the parts 532 to a receiving web 536 travelling at a second speed in the direction indicated by the arrow 538 associated with the receiving web. The illustrated example of the apparatus 530 comprises a rotatable transfer assembly 540 for receiving and applying the parts 532. The apparatus 530, as representatively shown in FIGS. 32 and 33, further comprises a driving apparatus 542 for transmitting rotational energy to a driven apparatus 544. The driving apparatus 542 includes at least one rotatable noncircular drive gear 546 and the driven apparatus 544 includes at least one rotatable noncircular driven gear 548. In use, the noncircular drive gear 546 engages and rotates the noncircular driven gear 548 which, in turn, rotates the transfer assembly 540.

The illustrated example of the transfer assembly 540 comprises at least one shell segment 550 connected to an output shaft 552. The shell segment 550 of the transfer assembly 540 may be connected to the output shaft 552 by any technique known to those skilled in the art such as, for example, bolts, screws, key and matching keyways, welding and the like or combinations thereof. For example, the shell segment 550 may be connected to the output shaft 552 by a key inserted into mating keyways in the shell segment 550 and output shaft 552. Similarly, the other components of the apparatus 530 of the present invention can be connected together employing the above described assembly techniques.

The shell segment 550, as representatively illustrated in FIGS. 32 and 33, can include a transport head 554 and a wall 556 connected to and extending perpendicularly from the transport head. The web member is also connected to the output shaft 552. The dimensions of the shell segment 550 will vary depending upon the desired output of the transfer assembly 540 and the size and shape of the discrete parts 532 being transferred. For example, the transport head 554 of the shell segment 550 may have an outer arcuate surface 558 spanning from about 20 degrees to about 340 degrees, a length of the outer arcuate surface of from about 1 inch to about 12 inches (about 25 mm to about 305 mm), and a width of from about 0.5 inch to about 20 inches (about 13 mm to about 512 mm). As the output shaft 552 rotates, the transfer assembly 540 travels in the direction indicated by the arrow 560 associated therewith. The outer arcuate surface 558 of the transport head, which is the circumferential, outer peripheral surface of the transfer assembly 540, travels along and defines an orbital path 562 that passes through a taking zone 564 and a transfer zone 566. The taking zone 564 and the transfer zone 566 are defined by the respective segments of the orbital path travelled by the outer arcuate surface 558 of the transfer assembly 540.

The illustrated example of the driving apparatus 542 includes a rotatable noncircular drive gear 546 connected to an input shaft 568. The illustrated example of the driven apparatus 544 includes a rotatable noncircular driven gear 548 connected to output shaft 552. The output shaft 552 is parallel to, but offset from the input shaft 568, such that the noncircular drive gear 546 is configured to engage and rotate the noncircular driven gear 548. The driving apparatus 542 may include a motor operatively connected through suitable gearing to the input shaft 568. Thus, in use, the motor rotates the input shaft 568 which rotates the noncircular drive gear 546 which, in turn, rotates the driven gear 548, output shaft 552 and transfer assembly 540.

Alternatively, the illustrated driven apparatus 544 may include a noncircular driven gear 548 which is connected to a jackshaft instead of being connected to the output shaft 552. The term "jackshaft" connotes a rotatable shaft supported in two locations that is capable of receiving the rotational energy from the driving apparatus 542 and transferring the energy to the output shaft 552. The jackshaft is parallel to but offset from the input shaft 568 such that the noncircular drive gear 546 is configured to engage and rotate the noncircular driven gear 548. The driven apparatus 544 may further include a transmitting apparatus, such as a pair of complementary gears connected to the jackshaft and output shaft 552 respectively, for conducting the rotational energy from the jackshaft to the output shaft 552 to rotate the output shaft 552 and the transfer assembly 540. Alternatively, the transmitting apparatus may include any mechanism known to those skilled in the art by which rotational energy can be conducted from one shaft to another such as, for example, circular gears, v-belts, timing belts, continuous chains and the like or combinations thereof. Further, the transmitting apparatus may include a second pair of complementary noncircular gears to provide additional speed variations.

It will be further appreciated that the method and apparatus 530 can utilize one or, in the alternative, two, three or more combinations of transfer assembly 540 and driven apparatus 544 in series to achieve the desired application of the discrete parts to the substrate web. The different combinations may allow the use of a continuously moving web to supply the discrete parts. In addition, greater speed ratio differentials may be achieved by using combinations of transfer assembly and driven apparatus in series. For example, referring now to FIGS. 34A, 34B, 35 and 36, there is representatively shown another apparatus generally indicated at 530 which receives discrete parts 532 of a web of an elastic material 570 travelling at a first speed in the direction indicated by the arrow 534 associated with the web 570, and transfers the parts 532 to a receiving web 536 travelling at a second speed in the direction indicated by the arrow 574 associated with web 536. The illustrated example of the apparatus 530 comprises three shell segments 550, represented by 550A, 550B and 550C (FIGS. 35 and 36), for receiving and applying the parts 532. The apparatus 530 further comprises a gearbox 576, as representatively shown in FIGS. 34A and 35, having a driving apparatus 542 which includes a rotatable noncircular drive gear 546 for transmitting rotational energy to the three driven apparatus 544, represented by 544A, 544B and 544C. The driven apparatus 544, which includes a rotatable noncircular driven gear 548, represented by 548A, 548B and 548C, is configured to rotate each of the shell segments 550.

Figure 35:
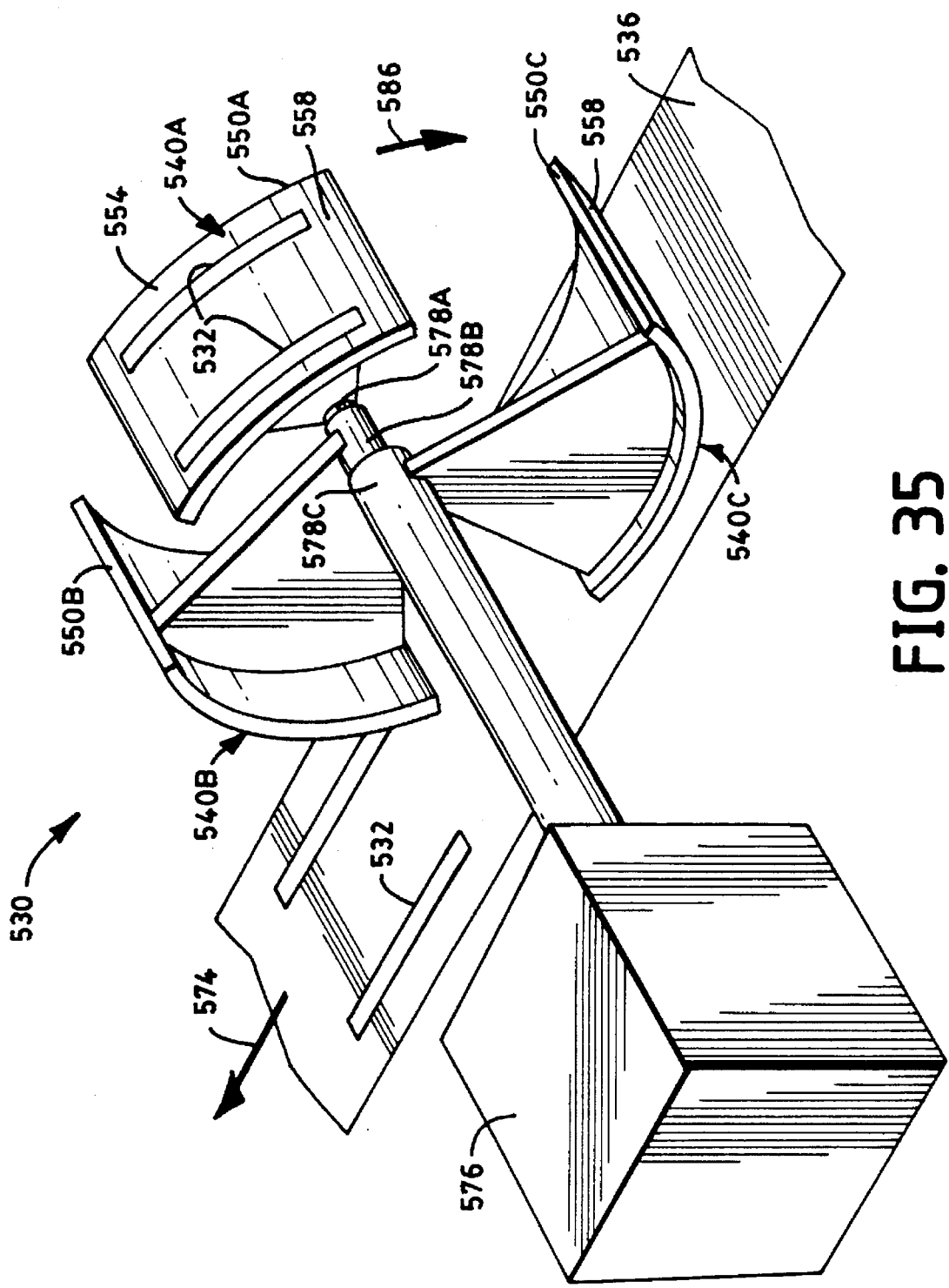
FIG. 35 representatively shows another pictorial view of the apparatus of FIG. 34A.
Figure 36:
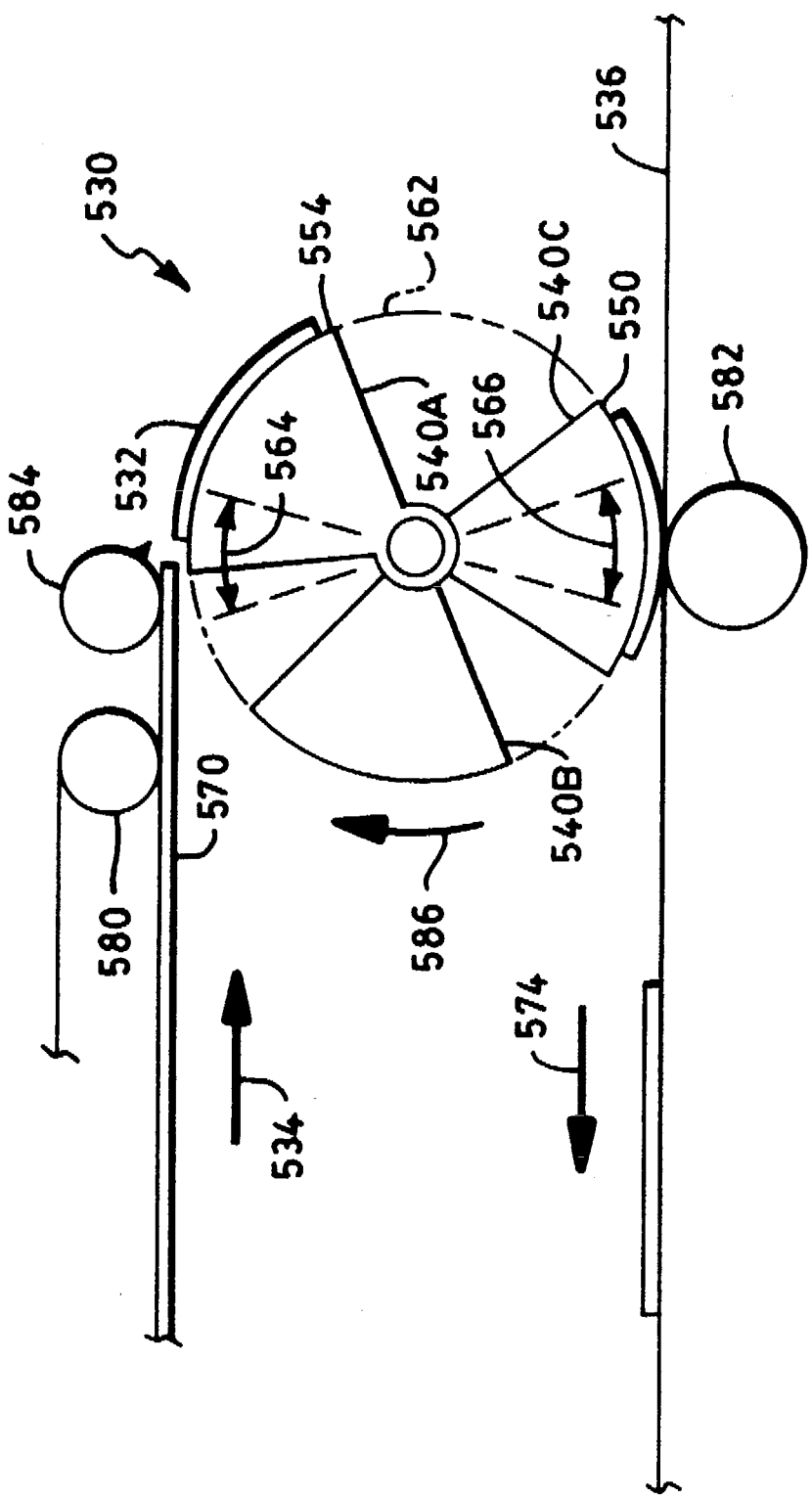
FIG. 36 representatively shows another schematic side view in elevation of the apparatus of FIG. 34A.

As illustrated in FIGS. 35 and 36, each of the shell segments 550 is connected to a concentric shaft 578, represented by 578A, 578B and 578C. As each concentric shaft 578 rotates, the respective transfer assembly 540 travels in the direction indicated by the arrow 586 associated with the transfer assembly. In use, the circumferential, arcuate outer surfaces 558 of the respective shell segments 550A, 550B, and 550C travel along and define the orbital path 562 that passes through taking zone 564 and transfer zone 566. The taking zone 564 and the transfer zone 566 are defined by the respective segments of the orbital path travelled by the arcuate outer surfaces of the transfer assembly 540.

The size and shape of each shell segment 550 may vary as the number of shell segments per transfer assembly 540 changes. For example, if the apparatus includes three shell segments as representatively illustrated in FIGS. 35 and 36, each shell segment 550 may have an outer arcuate surface which spans from about 30 to about 120 degrees of the orbital path 562 of the transfer assembly 540.

As illustrated in FIGS. 34A, 34B, 35 and 36, the example of the driving apparatus 542 includes the rotatable noncircular drive gear 546 connected to an input shaft 568. The illustrated example of each drive apparatus 544 includes the corresponding rotatable noncircular driven gear 548 connected to a corresponding jackshaft 588, represented by 588A, 588B and 588C. Each jackshaft 588 is parallel to but offset from the input shaft 568 such that the noncircular drive gear 546 is configured to engage and rotate the respective noncircular driven gears 548 thereby rotating the respective jack shafts 588. Thus, as illustrated, the single noncircular drive gear 546 is configured to engage and rotate the three noncircular driven gears represented by 548A, 548B and 548C which are respectively connected to the three jack shafts represented by 588A, 588B and 588C.

Figure 34A:
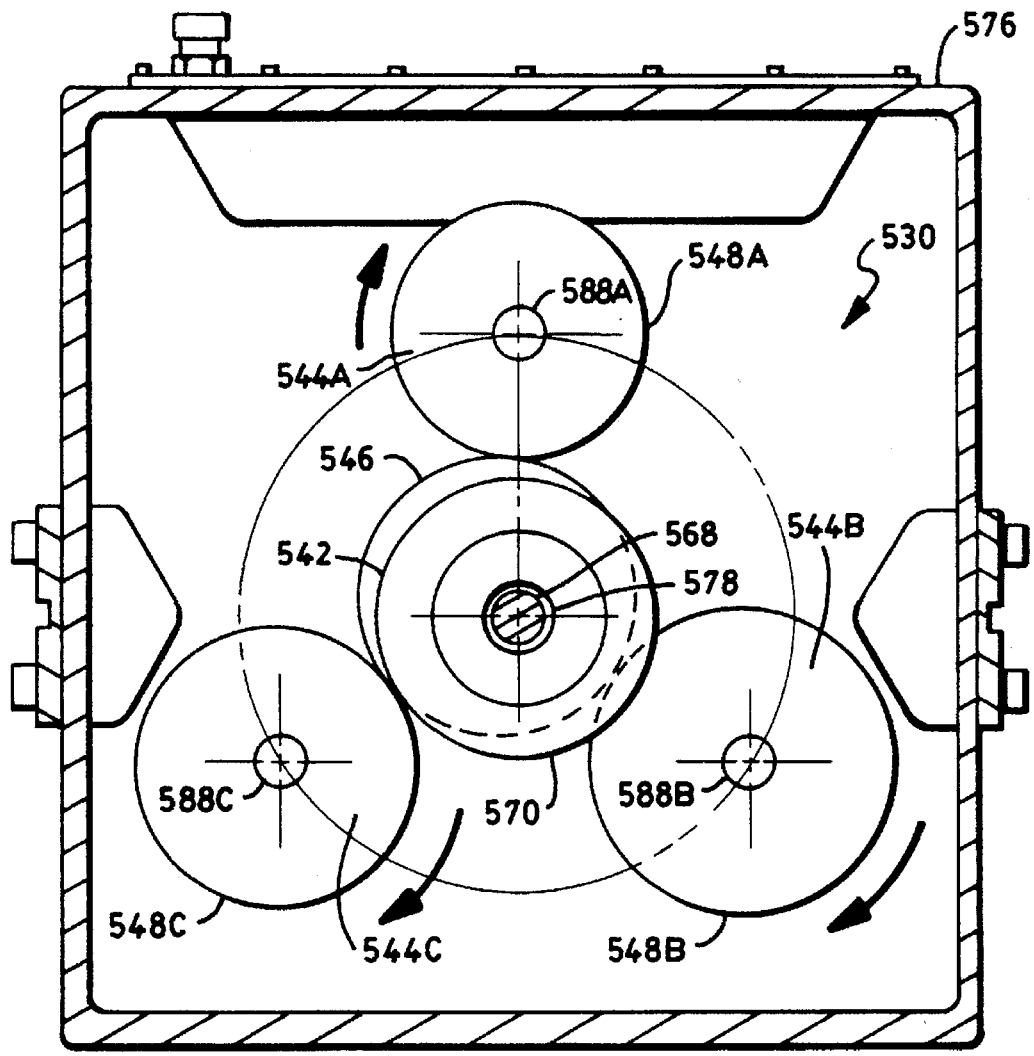
FIG. 34A representatively shows a schematic side view in elevation of another example of apparatus of the type useful to place the crotch elastic.
Figure 34B:
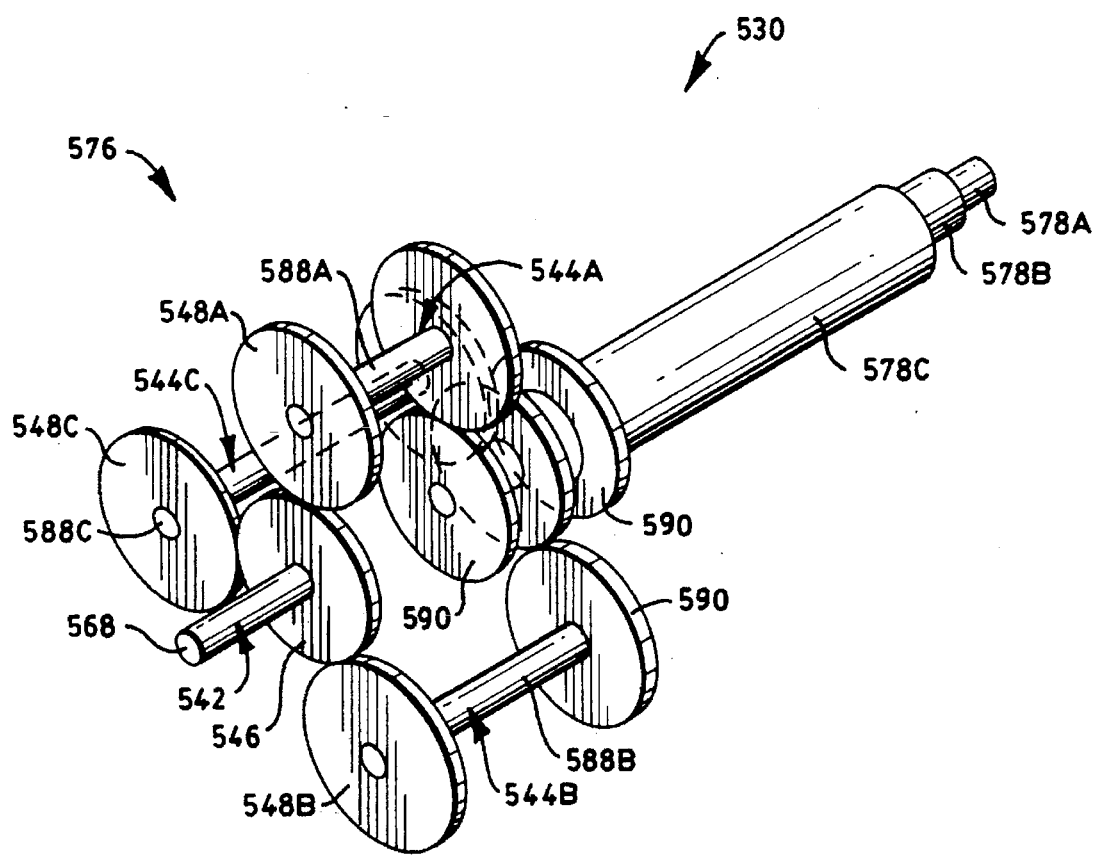
FIG. 34B representatively shows a pictorial view of the apparatus of FIG. 34A.

Each driven apparatus 544 may further include a transmitting apparatus 590, as representatively illustrated in FIG. 34B, such as a pair of complementary gears connected to each jackshaft 588 and each concentric shaft 578 respectively, for conducting the rotational energy from each jackshaft 588A, 588B and 588C to the respective concentric shaft 578A, 578B and 578C thereby rotating the respective concentric shaft 578 and transfer assembly 540. Alternatively, the transmitting means 590 may include any mechanism known to those skilled in the art by which rotational energy can be conducted from one shaft to another such as, for example, circular gears, v-belts, timing belts, continuous chains and the like or combinations thereof.

Further, each transmitting means 590 may include a second pair of complementary noncircular gears to provide additional speed variations. Each transmitting apparatus 590 may be connected to the respective jackshaft 588 and concentric shaft 578 by any technique known to those skilled in the art, such as those described above. For example, each transmitting apparatus may include a pair of complementary gears connected to the respective jackshaft and concentric shaft by a key inserted into mating keyways in the jackshaft and concentric shaft.

In operation, the driving apparatus 542 may include a motor operatively connected through suitable gearing to the input shaft 568. Thus, the motor rotates the input shaft 568 which rotates the noncircular drive gear 546 which, in turn, rotates the respective driven gears 548A, 548B and 548C and jack shafts 588A, 588B and 588C, which, in turn, rotate the respective concentric shafts 578A, 578B and 578C and shell segments 550A, 550B, and 550C.

The apparatus 530, as representatively illustrated in FIG. 36, may further comprise a heated knife cutter 584 to sever the continuously moving web of elastic material 570 into discrete parts 532 that are fed onto each shell segment 550. The pinch or heated knife cutter 584 may be any mechanism known to those skilled in the art that can sever a web of material into discrete segments such as, for example, a rotary cutter. It will be apparent that the continuously moving web of elastic material 570 may be omitted and the discrete parts 532 may be placed directly upon the transfer assembly 540. In addition, it will be apparent that the parts 532 may be adhered to the receiving web 536 by means of an adhesive applied in a selected pattern to the surface of the parts 532, or by any other suitable means for adhering the parts to the receiving web 536. Further in addition it will be apparent that the part 532 may be transferred to the receiving web 536 without adhesive, an adhesive being later applied or alternative methods of attachment used such as ultrasonic bonding.

The use of a noncircular drive gear 546 and a noncircular driven gear 548 in the apparatus 530, as representatively illustrated in the various aspects described above, provides an inexpensive and adaptable method for receiving discrete parts 532 travelling at a first speed and transferring the parts to a receiving web 536 travelling at a second different speed. To provide the variable angular velocity, the radius of the noncircular drive gear, or input gear, varies. Moreover, since the center to center distance between the noncircular gears remains constant, the radius of the noncircular driven gear, or output gear, changes to correspond to the variations in the radius of the input gear such that the gears remain engaged or meshed during the entire angular path of their rotation. The respective design of the noncircular gears can be controlled analytically to obtain the desired output function. For example, the speed profile of a typical set of complementary noncircular gears is representatively illustrated in FIG. 37. Thus, the combination of the complementary noncircular gears 546 and 548, as used to drive a transfer assembly 540, can provide variable angular velocity having periods where the velocity remains constant for a fixed duration. The fixed speed dwell can be advantageous when taking the discrete parts 532 onto the transport head 554 and when transferring them to the receiving web 536, particularly when the transfer occurs over a substantial arc length of contact.

Noncircular gears, such as those used in the present invention, can be purchased from Cunningham Industries, Inc. located in Stamford, Conn. Alternatively, one of ordinary skill in the art can manufacture the set of complementary noncircular gears if provided with the analytical representation of the desired output function as representatively illustrated in FIG. 37. For example, the design of a set of noncircular gears, as representatively shown in FIG. 38, can be developed as follows. First, the output function including the required process speeds and dwells must be laid out as in FIG. 37 to determine the proper radius of the orbital path that the transfer assembly follows and the proper gear ratios and gear angles for the noncircular gears. Second, the coefficients which establish the transition or acceleration deceleration portions of the noncircular gears, as representatively illustrated in FIG. 38, must be computed. Once the angles, ratios and coefficients are known, the gear center to center distance is chosen from which follows the required radii for the noncircular gears.

Figure 37:
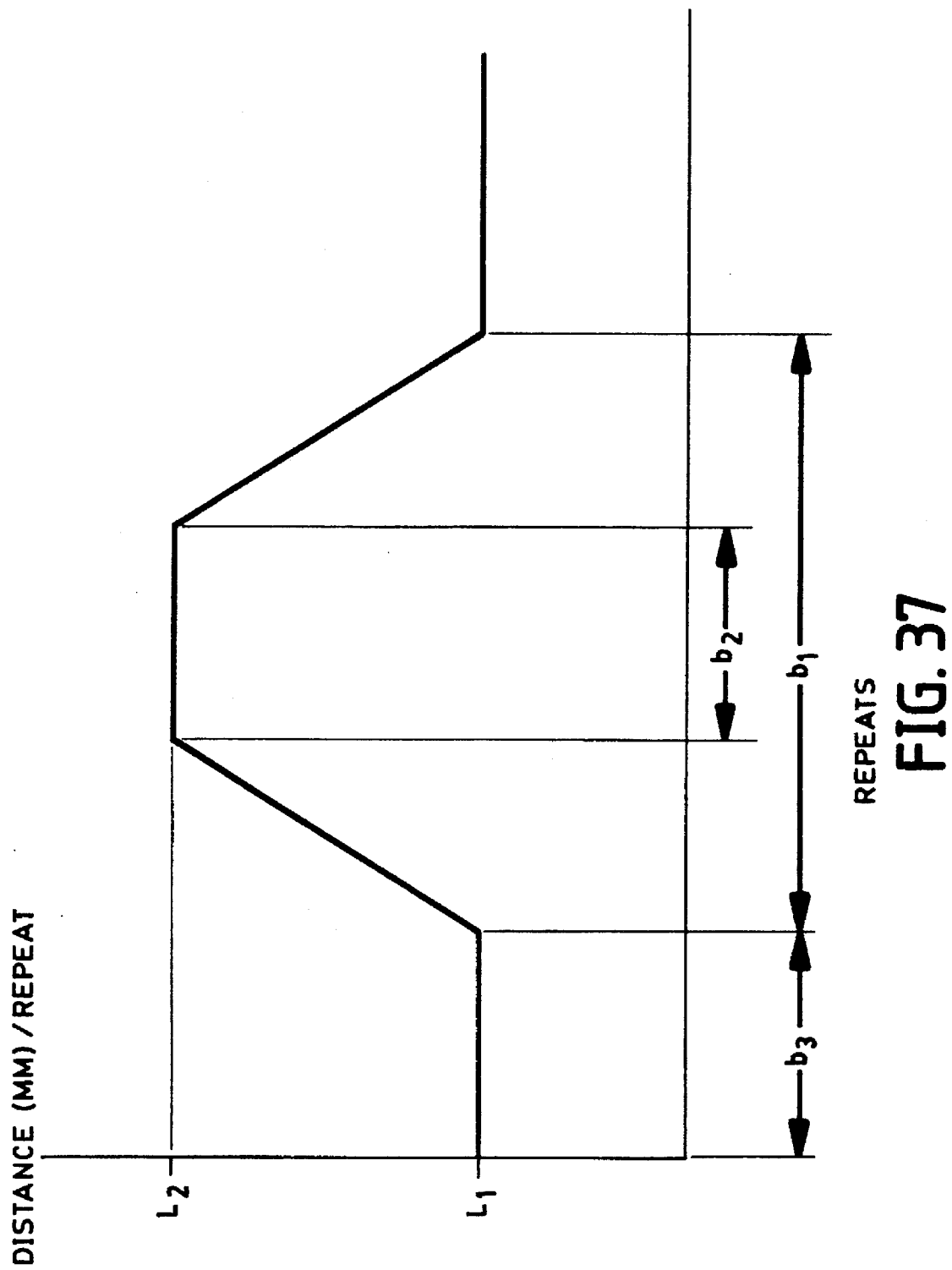
FIG. 37 representatively shows a speed profile for a typical set of complementary noncircular gears for the embodiment illustrated in FIGS. 34A, 34B, 35, and 36.

The radius of the orbital path is determined by calculating the total area under the output function curve as illustrated in FIG. 37. The equations for doing this are:

$$\text{Area}=L_1+0.5(b_1+b_2)(L_2-L_1) \tag{1}$$

$$R=\text{Area}/2\pi$$

where:

$R$=radius of the orbital path (mm)

Area=area under the output function curve (mm)

$L_1$=low speed of the transfer assembly (mm/repeat)

$L_2$=high speed of the transfer assembly (mm/repeat)

$b_1$=total time during the trapezoidal portion of the curve (repeats)

$b_2$=total time to dwell at high speed (repeats)

$b_3$=total time to dwell at low speed (repeats)

Figure 38:
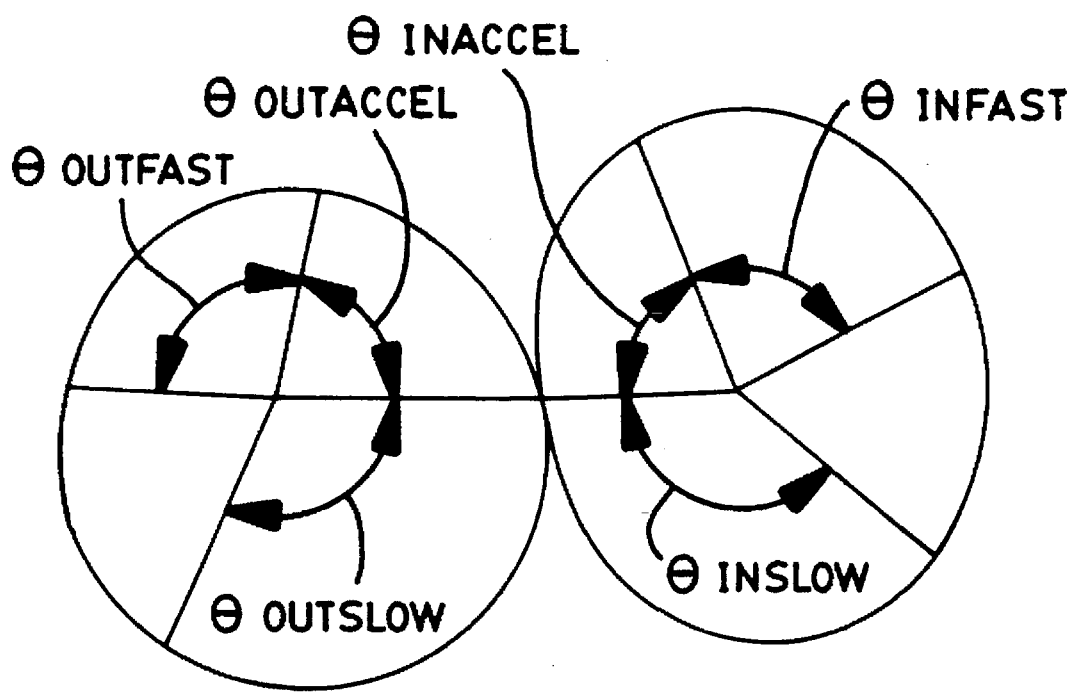
FIG. 38 representatively shows a schematic side view in elevation of a single noncircular gear set having designated angles of rotation.

Once the radius of the orbital path is determined, the ratios for the noncircular gears, as illustrated in FIG. 38, are determined as follows:

$$\theta\text{inslow}=2\pi b_3 \tag{3}$$

$$\theta\text{infast}=2\pi b_2 \tag{4}$$

$$\theta\text{inaccel}=2\pi(b_1-b_2) \tag{5}$$

$$\theta\text{outslow}=(L_1 b_3)/R \tag{6}$$

$$\theta\text{outfast}=(L_2 b_2)/R \tag{7}$$

$$\theta\text{outaccel}=[2(b_1-b_2)(l_1/2+(L_2-L_1)/4))]/R \tag{8}$$

Slow speed ratio=$Y_1$=$\theta$outslow/$\theta$inslow=$L_1/(2\pi(R))$ (9)

High speed ratio=$Y_2$=$\theta$outfast/$\theta$infast=$L_2/(2\pi(R))$ (10)

Once the proper ratios and angles have been chosen, the coefficients which define the shape of the noncircular gears can be computed. Gears designed with a sinusoidal function for the transition have been found to give good results in practice. The equation which defines the shape of the transitional part of the gears is given by:

$$\eta_{accel}=A-B\cos(C\theta) \tag{11}$$

where $\eta_{accel}$=ratio as a function of angular position during transition and $$A=(Y_1+Y_2)/2 \tag{12}$$

$$B=(Y_2-Y_1)/2 \tag{13}$$

$$C=2\pi/\theta\text{inaccel} \tag{14}$$

The actual pitch line radius of the noncircular gears can be determined once a choice has been made for the center to center distance between the noncircular gears. The gear radius is then given by:

$$R_{driven\ gear}=D_{center}/(1+\eta_{accel}) \tag{15}$$

$$R_{drive\ gear}=D_{center}-R_{driven\ gear} \tag{16}$$

where:

$R_{driven\ gear}$=The radius of the noncircular driven gear $R_{drive\ gear}$=The radius of the noncircular drive gear $D_{center}$=The desired gear center to center distance By computing the ratios at any desired interval along the transition using equation (11) above, a smooth curve of the pitch line can be derived using equations (15) and (16). This smooth curve of the pitch line is used to construct a gear blank which is used to manufacture the noncircular gears.

Thus, the design of the profile of the complementary noncircular gears can be analytically determined to obtain the desired output function which can include variable angular velocities with fixed speed dwells. When two sets of complementary noncircular gears are used the output angles of the first set become the input angles of the second set. In addition, all of the angles on the gears must add up to $2\pi$ radians or 360 degrees.

As compared to conventional methods, such as the slip gap method, for changing the speed of a discrete part such that it can be applied to a continuously moving web, the use of noncircular gears provides the ability to obtain greater changes in speed and to maintain constant speeds for a fixed duration. The fixed speed dwell achieved by using noncircular gears can be accurately and inexpensively designed to precisely control the length and placement of the discrete parts 532.

For example, in the various aspects of the noncircular gears disclosed herein, the profile of the noncircular gears 546 and 548 is analytically designed such that the rotatable transfer assembly 540 receives discrete the parts 532 in the taking zone 564 (shown in FIG. 33) while maintaining a constant surface speed substantially equal to the incoming speed of the parts 532. Moreover, the profile of the noncircular gears 546 and 548 is designed such that the surface speed of the rotatable transfer assembly 540 changes to a second constant surface speed as the rotatable transfer assembly 540 moves from the taking zone 564 to the transfer zone 566. The term "surface speed," as used herein, refers to the speed of the circumferential, outer peripheral surface of the transfer assembly 540 as defined by arcuate outer surfaces 558 of the respective transport heads 554. The profile of the noncircular gears can be designed such that the speed of a discrete part 532 being transferred is substantially equal to the speed of the receiving web 536 as the discrete part is applied to the receiving web in the transfer zone 566. The surface speed of the transfer assembly 540 is maintained substantially constant in the taking zone 564 and the transfer zone 566 for from at least about 0 to about 300 degrees of rotation, desirably from about 10 to about 300 degrees of rotation, and more desirably from about 120 to about 240 degrees of rotation of the transfer assembly 540. In addition, the surface speed increase or decrease of the transfer assembly 540 as it moves from the taking zone 564 to the transfer zone 566 defines a speed ratio of from at least about 0.9:1 to about 20:1, desirably from about 0.9:1 to about 10:1, and more desirably from about 0.9:1 to about 4:1. The term "speed ratio", as used herein, defines the ratio of the surface speed of the transfer assembly 540 as the parts 532 are applied to the receiving web 536 to the surface speed of the transfer assembly 540 as the parts 532 are taken.

The transfer assembly 540, as representatively illustrated in the various configurations of the invention, includes the transport head 554, as representatively illustrated in e.g.

FIGS. 32 and 35, to grip the discrete parts 532 in the taking zone 564 and to transport the parts to the transfer zone 566. In a particular aspect of the invention, the transport head 554 may include a suction apparatus for providing a region of relatively low pressure. The suction apparatus may include ports through which a suction may be selectively imposed. Thus, the suction may be activated in the taking zone 564 and deactivated in the transfer zone 566 as the part 532 is applied to the receiving web 536. In this manner, positive control is maintained over the parts 532 at all times during the transfer process since, in these embodiments, there is no time at which the parts are free of the holding action provided by the transport head 554. Alternatively, the transport head may include any conventional technique known to those skilled in the art for holding and releasing parts such as, for example, mechanical clamps, electrical clamps, magnetic clamps and the like or combinations thereof.

The various aspects of the apparatus 530 may further comprise an infeed conveyor 580 and an outbound article conveyor 582 as representatively illustrated in FIG. 32. The infeed conveyor 580 may supply the discrete parts 532 to the transfer assembly 540. The outbound article conveyor 582 may carry the receiving web 536.

The method and apparatus described here may be used in the manufacture of articles such as diapers, training pants, and adult incontinence products, among other uses, in addition to having application to fabricating the blank 10 of the garment 25. The method and apparatus may be used to apply discrete parts or components, such as, for example, elastic elements, tapes, snaps and hook and loop materials to the respective product. Articles such as diapers and incontinence products are described, for example, in U.S. Pat. Nos. 4,704,116 issued Nov. 3, 1987, to Enloe; U.S. Pat. No. 4,798,603 issued Jan. 17, 1989, to Meyer et al.; U.S. Pat. No. 4,710,187 issued Dec. 1, 1987, to Boland et al.; U.S. Pat. No. 4,770,656 issued Sep. 13, 1988, to Proxmire et al.; and U.S. Pat. No. 4,762,521 issued Aug. 9, 1988 to Roessler et al.; the disclosures of which are incorporated herein by reference.

In a particular aspect, apparatus such as at 530 may be used to apply parts of leg elastic to a disposable diaper, or the garment. For example, a continuously moving web of elastic material 570 may be fed into the pinch or heated knife cutter 584. The pinch or heated knife cutter 584 severs the web of elastic material 570 into discrete parts 532 which are fed onto the transfer assembly 540 in the taking zone 564. As transfer assembly 540 rotates, the parts of leg elastic 532 are held onto the transfer assembly 540 by transport head 554 which includes suction. The suction is activated in the taking zone 564 and deactivated in the transfer zone 566 as the parts 532 are transferred to the receiving web 536. The driving apparatus 542 and driven apparatus 544 which, in combination, rotate the transfer assembly 540 include a pair of complementary noncircular gears 546 and 548. The profile of the noncircular gears 546 and 548 is designed as described above such that, as the noncircular gears 546 and 548 and transfer assembly 540 rotate, the transfer assembly 540 maintains a substantially constant surface speed as the parts of leg elastic 532 are taken and transferred. For example, the transfer assembly 540 receives the parts of leg elastic 532 in the taking zone 542 while maintaining a constant surface speed substantially equal to the speed of the web of elastic material 570. The surface speed of the transfer assembly 540 then changes to a second constant surface speed such that the speed of the parts of leg elastic 532 being transferred is substantially equal to the speed of the receiving web 536 as the parts of leg elastic 532 are applied to the web 536 in the transfer zone 566. The surface speed of the transfer assembly 540 is then changed back to substantially equal the speed of the web of elastic material 570.

The parts of leg elastic 532 applied to the receiving web 536 may be made of any suitable material having elastic or stretchable properties. Examples of such materials include porous and nonporous films or layers of natural rubber, synthetic rubber, or thermoplastic elastomeric polymers, and can be panels, or single, or multiple threads or filaments or ribbons thereof. These materials may also be heat-shrinkable or heat-elasticizable. Furthermore, these stretchable materials may be formed with gatherable layers, such as spunbonded polymer materials, as a stretch-bonded laminate. For example, a suitable stretch-bonded laminate comprises two gatherable layers of 0.4 ounce per square yard of spunbond polypropylene having therebetween a layer of meltblown elastic material such as a Kraton elastic in either layer form or separate threads of material having a basis weight of about 0.5 ounce per square yard. The layer of the elastomeric material is stretched, the two layers of polypropylene then joined to the elastomeric layer, and upon relaxing the layers, the polypropylene layers gather. The materials may be breathable or nonbreathable.

Figure 39:
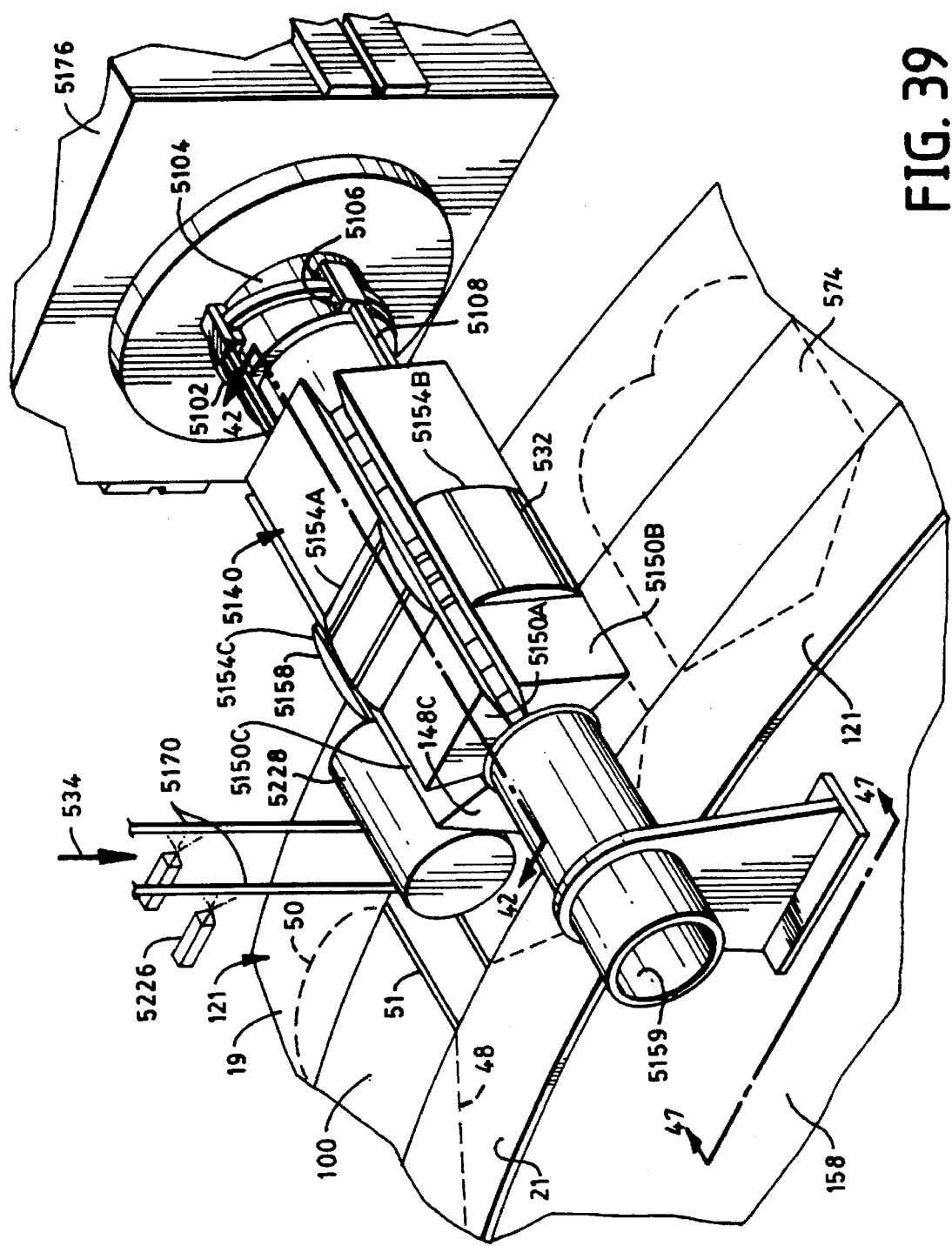
FIG. 39 shows a pictorial view of an embodiment of apparatus specifically useful for placing the crotch elastics elements.

Referring now to FIG. 39, there is representatively shown the crotch elastics subsystem 159 as applied in the processing system illustrated in FIG. 13. As shown therein the crotch elastics subsystem 159 generally receives discrete parts 532 as part of webs 570 travelling at a first speed in the direction indicated by the arrow 534 associated therewith and transfers the parts 532 to the workpieces 319 as shown in FIG. 20 which are being fabricated into blanks 10 on the combined web 121, travelling at a second speed in the direction indicated by the arrow 574 associated therewith.

Figure 41:
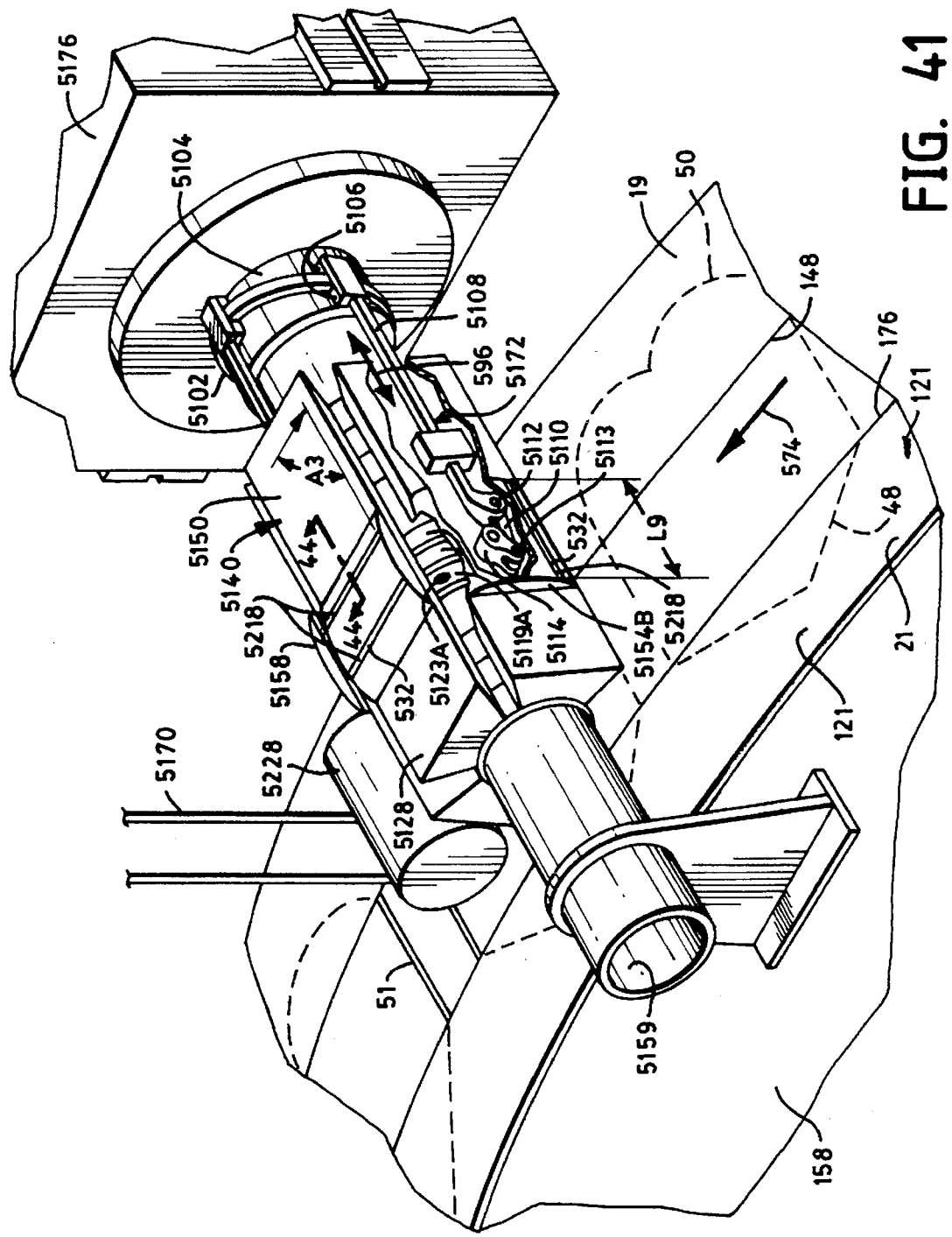
FIG. 41 shows an enlarged pictorial view of the embodiment of FIG. 39, with parts cut away to show the cam system and exemplary suction ports in a slip ring.
Figure 40:
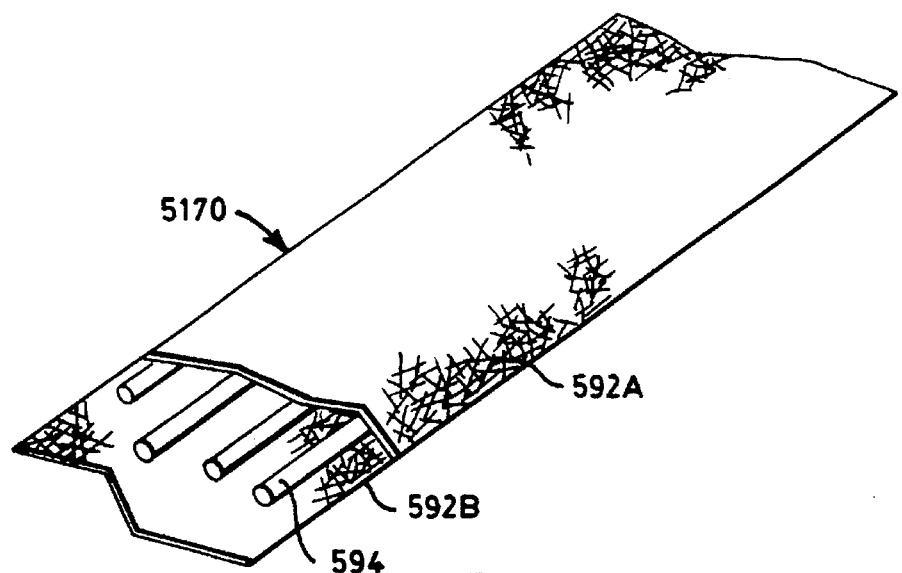
FIG. 40 shows a pictorial view, with parts cut away, of a portion of an incoming web of crotch elastics to be transferred by apparatus of the invention.

Referring to FIGS. 39–41, incoming webs of material 5170 comprise first and second layers 592A and 592B of spunbonded polypropylene (0.7 ounces per square yard), and a plurality of threads 594 of elastic adhesively secured between the layers 592A and 592B. The elastic can be any of a variety of elastics suitable for providing the elastic property in the web 5170. In a web 0.625 inch wide, suitable elasticity is provided by four threads of 940 decitex lycra generally uniformly spaced across the width of the web 5170.

Figure 42:
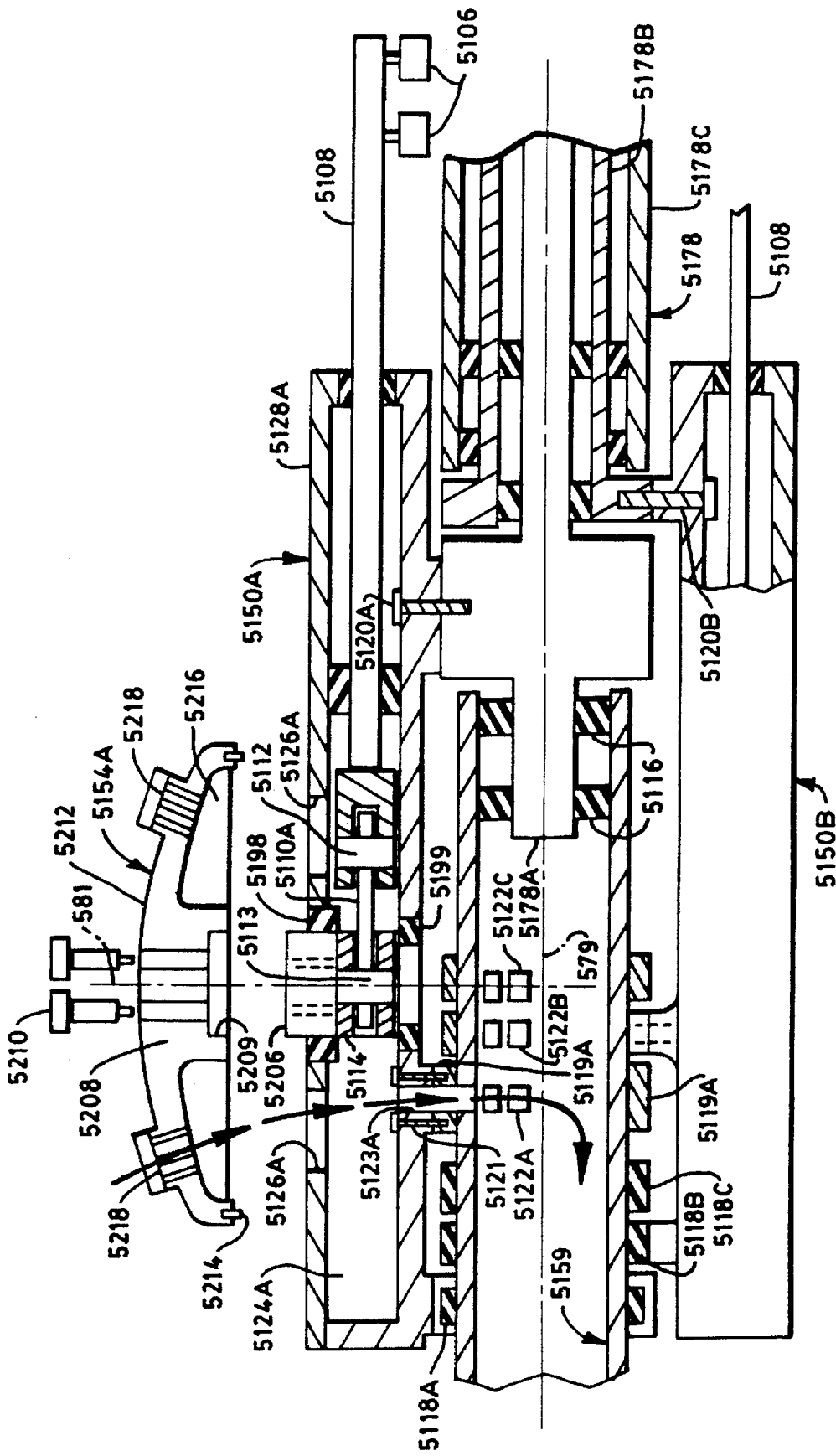
FIG. 42 is a sectional view taken at 42—42 of FIG. 39.
Figure 43:
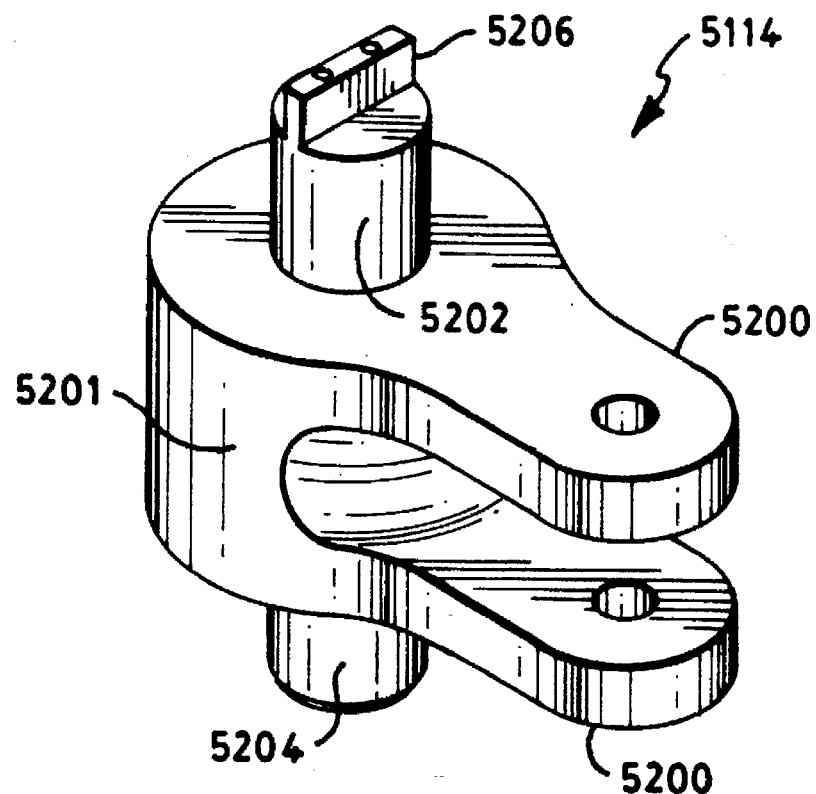
FIG. 43 is a pictorial view of the crank clevis which is actuated by the cam system.

In the example illustrated in FIG. 39, the rotatable transfer assembly 5140 includes three shell segments 5150A, 5150B, and 5150C, supported by concentric shaft 5178 as shown in FIG. 42 and tubular suction conduit 5159.

Referring now to FIGS. 39–42 in combination, the drive system in gearbox 5176, operating through concentric shaft 5178, causes the shell segments 5150A, 5150B, and 5150C to rotate about the concentric shaft 5178 and tubular suction conduit 5159. As the shell segments 5150 rotate about a first generally horizontal axis 579 of the transfer assembly 5140, a cam mechanism generally designated 5172 rotates the transport head 5154 about a radial axis 581 which intersects the generally horizontal axis 579 of the transfer assembly.

Figure 47:
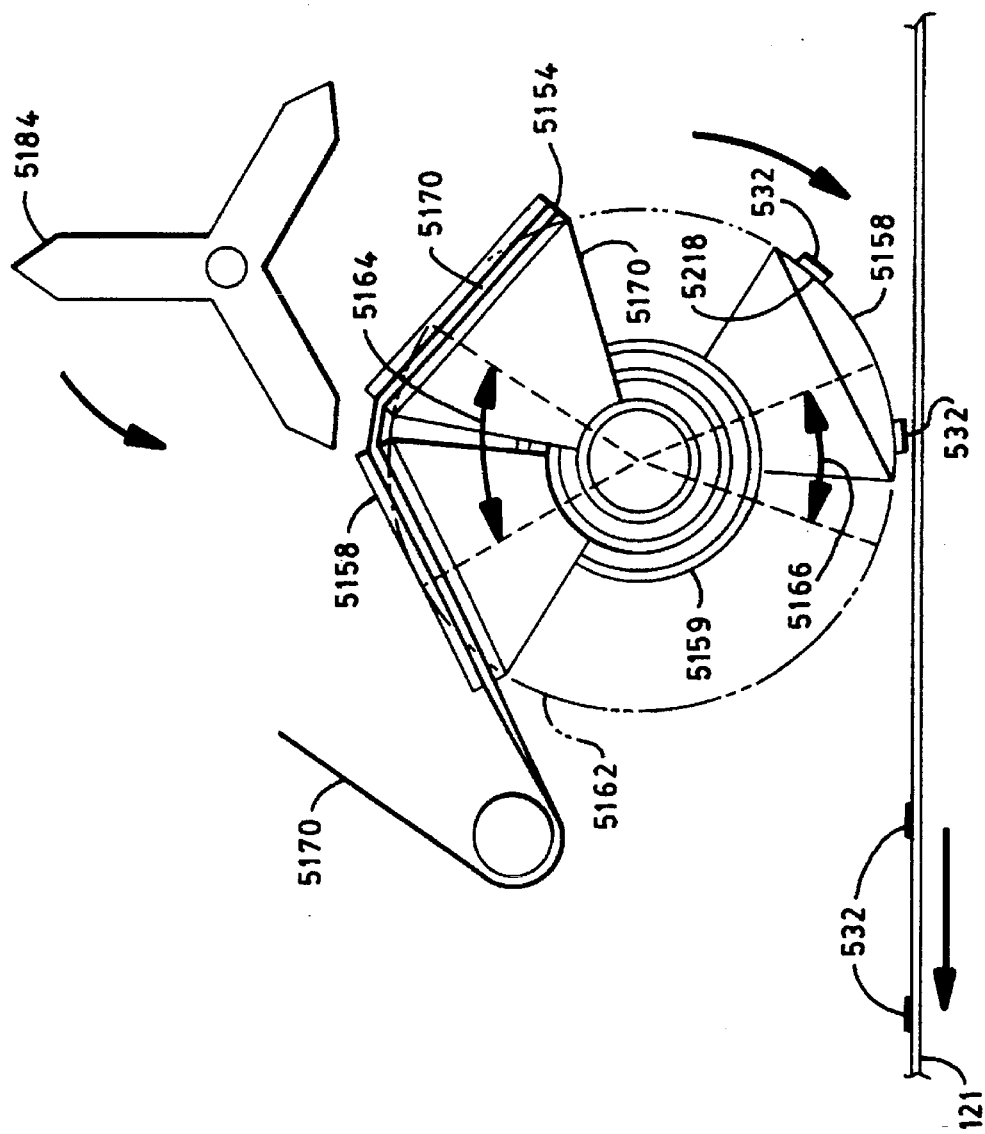
FIG. 47 is an elevation view generally taken at 47—47 of FIG. 39.

Accordingly, starting from the taking zone 5164 in FIG. 47, the arcuate top wall 5158 of the transport head is disposed transverse to the direction of travel of the incoming web 5170 of elastic material as the respective transport head picks up the incoming elastic material. The cam mechanism 5172 then rotates the transport head 90 degrees about radial axis 581 by the time it reaches the transfer zone 5166, and rotates it back the same 90 degrees by the time it returns to the taking zone.

Referring to FIG. 41, cam mechanism 5172 includes an external cam 5102 extending outwardly from, and circumferentially about, drum 5104 which is fixedly mounted to the gearbox 5176. A pair of cam followers 5106 connected to each shell segment follows the cam 5102 about the perimeter of the drum 5104. Push rod 5108 extends from cam followers 5106 toward the respective transport head 5154 (FIG. 39), and connects to actuating arm 5110 through pin 5112. Actuating arm 5110 connects to the respective transport head 5154 through pin 5113 and crank clevis 5114, as is discussed hereinafter. Accordingly, the reciprocating motion of push rod 5108, as suggested by the double headed arrow 596, causes corresponding rotation of the respective transport head 5154 as the respective shell segment 5150 traverses the orbital path 5162 (FIG. 47).

Referring especially to FIG. 42, the stationary tubular suction conduit 5159 is mounted to the rotating concentric shaft 5178 through shaft segment 5178A and bearings 5116. Shell segment 5150A is mounted to tubular conduit 5159 through bearing 5118A. Similarly shell segments 5150B and 5150C are mounted to tubular conduit 5159 through bearings 5118B and 5118C respectively.

Shell segment 5150A is mounted to concentric shaft member 5178A by bolt 5120A. Similarly shell segments 5150B and 5150C are mounted to concentric shaft members 5178B and 5178C by bolts 5120B, and 5120C. Bolt 5120C is not shown.

Slip ring 5119A is bolted to shell segment 5150A by bolts 5121, and extends about, and is mounted for rotation about tubular suction conduit 5159 at a fixed longitudinal location along the length of the conduit. A first array of suction ports 5122A is disposed circumferentially about the outer wall of the conduit 5159 along a portion of the path of rotation of slip ring 5119A. Referring to FIGS. 41 and 42, a second array of suction ports 5123A is disposed about a portion of the circumference of slip ring 5119A adjacent shell segment 5150A, and in alignment with the first array of suction ports in the conduit 5159. Conventional suction seals (not shown) are used between the slip ring and the outer circumferential wall of the conduit 5159. Accordingly, as the slip ring 5119A rotates about conduit 5159 with shell segment 5150A, the second array of suction ports on the slip ring comes into alignment with the first array of suction ports on the conduit. Upon such alignment, suction is effected between conduit 5159 and the interior chamber 5124A of the shell segment 5150A, as shown in FIG. 42. Correspondingly, the suction in the interior chamber 5124A is transferred to transport head 5154A through a third array of suction ports 5126A in the top cover 5128A of shell segment 5150A.

Crank clevis 5114 (FIG. 43) is mounted to shell segment 5150A by upper and lower bearings 5198, 5199. A pair of arms 5200 extend outwardly from the main body 5201 of the crank clevis, for receiving the actuating arm 5110A. A pair of upper and lower generally circular bearing posts 5202, 5204 extend upwardly and downwardly, respectively, from the upper and lower surfaces of arms 5200 and engage the upper and lower bearings 5198, 5199. Male slot key 5206 extends upwardly from the upper bearing post 5202.

Transport head 5154A has a main body 5208. Female slot 5209 corresponds with, and receives, male slot key 5206 on the crank clevis 5114. Transport head 5154A is secured to crank clevis 5114, through the cooperation of male slot key 5206 and female slot 5209, using a pair of bolts 5210. Accordingly, when the female slot 5209 is engaged with male slot key 5206, rotational motion of the crank clevis 5114 causes corresponding rotational motion in the transport head 5154A.

The main body 5208 of the transport head extends to an outer arcuate top wall 5212, shown in FIG. 42. A suction seal 5214 extends in a circular path, on transport head 5154A, about the third array of suction ports 5126A, providing a suction seal between the interior chamber 5216 of the transport head and the top cover 5128A of shell segment 5150A. The third array of suction ports 5126A is disposed radially about crank clevis 5114, in a generally circular arrangement, such that suction in the interior chamber 5124A of the shell segment is readily transmitted into the interior chamber 5216 of the transport head.

The arcuate top wall 5212 of the transport head 5154 includes a taking section 5218. Referring to FIGS. 41 and 44–46, each taking section 5218 has a length "L9" and a width "W9", with the length being disposed in a direction transverse to the arc of the arcuate top wall 5212, whereby each taking section 5218 lies within generally a constant portion of the corresponding arcuate outer surface of top wall 5212 along its entire length.

Figure 44:
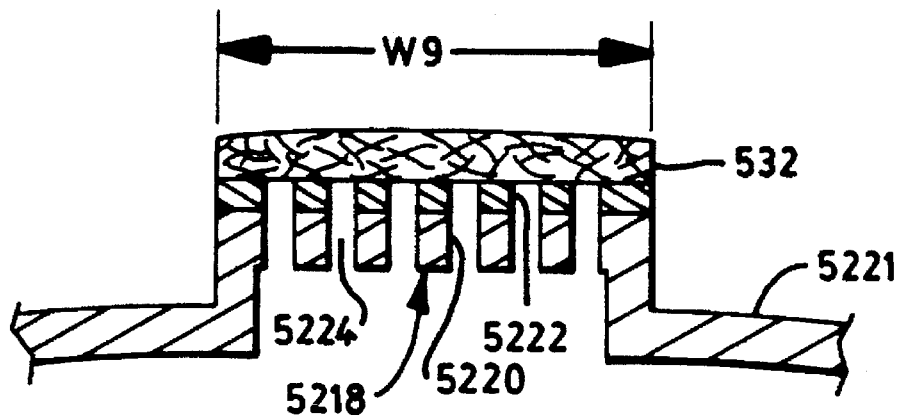
FIG. 44 is a cross section of the taking section of the outer wall of the transport head, with a discrete part thereon, taken at 44—44 in FIG. 41.
Figure 46:
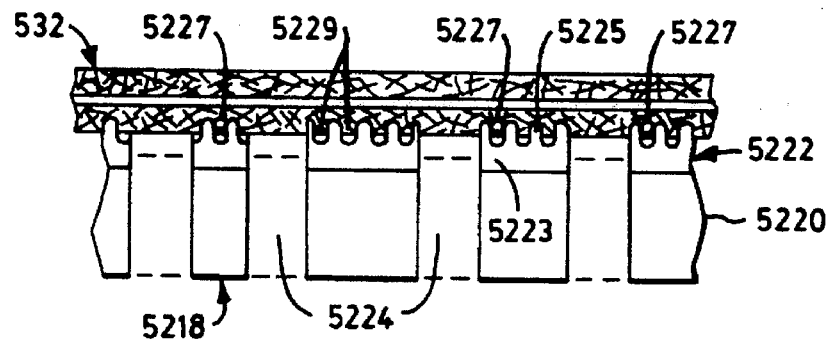
FIG. 46 is a cross-section as in FIG. 44, further enlarged to show the protrusions.

As seen in FIG. 44, each taking section 5218 includes a substrate portion 5220 extending above the main level 5221 of the arcuate outer surface of top wall 5212 of transport head 5154, and a roughened coating 5222. While not critical, and while no dimensions are considered controlling, the substrate portion 5220 is preferably raised e.g. about 0.005 inch to about 0.125 inch above the main level 5221 of the arcuate outer surface of the top wall 5212, to facilitate performance of the taking sections. The roughened coating 5222 can be characterized as any coating that provides a base surface component 5223 as shown in FIG. 46 overlying the substrate portion 5220, and an array of protrusions 5225 extending from the base surface component. The protrusions 5225 extend at least 0.006 millimeter from the base surface component, with a range of about 0.01 to about 0.03 millimeter being preferred. Any upper limit to the length of the protrusions depends on the characteristics of the discrete parts to be transferred by the transport head. However, typically the protrusions will not extend more than about 3 millimeters from the base surface component.

In preferred embodiments, the roughened coating 5222 has release characteristics generally corresponding to those of Teflon® polytetrafluoroethylene. However, a variety of release characteristics are acceptable, depending on the remainder of the process. A preferred coating is a plasma coating supplied as coating 902EA from Plasma Coatings, Inc., Waterbury, Conn. Since the discrete parts being transferred here, namely the crotch elastics 51, are generally small in nature, the coating 5222 used here is generally more aggressive than the coating 448 used on the transfer rolls, e.g. rolls 102, 156, 158.

The spacing between the protrusions 5225 in the array of protrusions preferably is selected in view of the texture of the surface of the respective discrete part 532 which faces the transport head. The protrusions 5225 should be spaced far enough apart to engage any surface texture of the discrete part, and close enough together to have sufficient engagement with elements of the parts 532 to provide a significant interaction between the elements of the parts and the protrusions on the coating. Thus, in applicants' contemplated application wherein the discrete parts are made with spunbonded and like material, the protrusions should be spaced far enough apart that the fibers 5227 can descend into the valleys 5229 between the protrusions 5225, and thereby engage the sidewalls of the valleys, to thereby fix the fibers, and correspondingly, the parts, in position on the taking sections 5218.

"Textured surface" and "texture" of the surface of the parts 532 refers to any irregularities in the respective surface of the part that gives effective third dimension to the surface. Thus, the fibers in spunbonded fabrics comprise irregularities. Similarly, an emboss pattern in an otherwise smooth surface layer would comprise a texture. Irregularities may be uniformly spaced as in a repeat emboss pattern, or spaced at random as with spunbonded fibers.

The widths across the valleys in the projection matrix are necessarily less than the cross-sections of the fibers in the outer layers 5230 of the webs 5170. As the webs 5170 are drawn onto the taking sections 5218 as shown in FIG. 44, the fibers 5227 as shown in FIG. 46 in the corresponding spunbonded outer layer 5230 interact with the roughened surface provided by the plasma coating 5222, wherein the individual fibers become drawn below the tops of the protrusions 5225 and into the intervening valleys 5229, thereby creating stresses in the matrix of the spunbonded material which interact with the protrusions on the corresponding taking section to hold the discrete parts securely in a fixed position on the taking section, and correspondingly, maintaining the existing elongation of the respective discrete parts.

Figure 45:
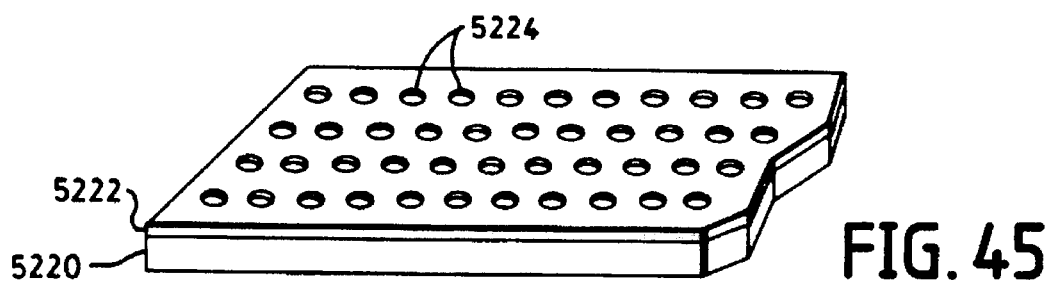
FIG. 45 is an enlarged fragmentary pictorial view of the surface of the taking section.

Referring to FIGS. 44, 45 and 46, an array of suction ports 5224 extend through the substrate 5220 and coating 5222 of the taking section, thus applying the suction to the discrete parts as they are disposed on the outer arcuate surface (e.g. the taking sections 5218) of the top wall 5212 of the corresponding transport head 5150.

As shown in the drawings, and especially referring to FIG. 42, shell segments 5150B and 5150C preferably correspond in general with the structure disclosed for shell segment 5150A, with corresponding provision for bearings 5118B and 5118C, slip rings 5120B and 5120C, and concentric shafts 5178B and 5178C. Similarly the cam mechanism is preferably the same for all shell segments.

The embodiment illustrated in FIGS. 39–46 will be briefly described hereinafter.

Adhesive is applied to the incoming elasticized webs of material 5170 by adhesive applicators 5226, and is cooled by turning roll 5228, which also turns the elastic webs into alignment with the corresponding transport head 5154C on the transfer assembly 5140. The surface driving speed of the transfer assembly is faster than the corresponding driving speed of the web unwind (not shown). Accordingly, in the embodiment shown, the elastic elements 594 of webs 5170 are advantageously elongated between about 100% to about 300% and preferably about 150% from their relaxed length. Thus, the webs are under tension exerted by the elastic threads 594 as the webs are taken onto the transport head 5154C.

As seen in FIGS. 39 and 41, the arcuate outer surface 5158 of the transport head is oriented transverse to the direction of travel of the incoming webs 5170 at the respective transport head. Suction is activated on the taking sections of the transport head 5154C as transport head 5154C rotates into position to take the incoming webs onto its taking sections. As the transfer assembly continues to rotate about its horizontal axis 579 as shown in FIG. 42, the taking sections of the transport head 5154C take and hold corresponding portions of the webs 5170, thus continuing the drawing of the webs 5170 into the transfer assembly. Accordingly, the leading edge of each part 532 is oriented at an angle "A3" transverse to the direction in which the part is travelling when the part is taken onto the transport head in taking zone 5164.

As the transfer assembly 5140 rotates under the driving force of the driving apparatus 542 and the gearbox 5176, the webs 5170 are severed into individual discrete parts 532 by a heated knife or other cutter 5184 as seen in FIG. 47.

The elongation of the individual discrete parts is maintained by the combined action of the protrusions 5225 of the plasma coating 5222 and the suction through the suction ports 5224. FIG. 45 illustrates a typical suction port pattern for a taking section approximately 0.5 inch wide.

Without plasma coating 5222, and using 45 inches of water, suction, the above web material 5170, including layers 592A, 592B of 0.7 ounce per square yard spunbonded polypropylene and four threads of 940 decitex lycra, after being severed by heated cutter 5184, exhibits greater than 10% snap-back, i.e. retracts to length shorter than 90% of the length, $L_1$, as shown in FIG. 37. Using the plasma coating 5222, and using only 10 inches water of suction, snap-back is less than 1%. Both the amount of suction, and the characteristics of the coating material 5222 can be adjusted to affect the amount of snap-back tolerated by the specifications of the material being processed and the product being made. The amount of snap-back increases as the amount of suction is decreased. Snap-back also increases as the character of the coating material 5222 changes to reduce the amount of entanglement between the fibers or other texturing of the surface of layers 592 and the protrusions 5225.

While the plasma coating 5222 is preferred, other types of coatings can be used to provide the protrusions 5225. For example, conventional emery paper or the like can be used; but the corresponding emery paper substrate does not exhibit the beneficial long term wear characteristics of the plasma coating. So the plasma coating is preferred.

As the transfer assembly 5140 continues to rotate, the transport head 5154C moves around to the positions shown in FIG. 41 for transport heads 5154A and 5154B. By the time the transport head reaches the position shown for transport head 5154B, the cam 5102, acting through connecting linkages of cam follower 5106, pushrod 5108, actuating arm 5110, pin 5112, pin 5113, and crank clevis 5114 rotates the transport head such that it forms an angle with the radial axis 581 greater than about 85 degrees, preferrably being about 90 degrees. The transport head 5154B is positioned as shown in FIGS. 39 and 41, wherein the leading edge of the part is parallel to the direction of travel on the transfer assembly, and by the time the discrete part 532 reaches combined web 121, parallel to the direction of travel of the combined web 121. At about the position shown for transport head 5154B in FIG. 39, the non-circular gears in gearbox 5176 cause an increase in the radial velocity of the corresponding transport head as described above with respect to FIGS. 37 and 38. By the time the transport head reaches the combined web 121 at the transfer zone 5166 as shown in FIG. 47, the surface speed of the discrete parts 532 generally corresponds with the surface speed of the web 121.

Adhesive applied at adhesive applicators 5226 is then activated. As the discrete parts 532 contact the web 121, the suction is released as the corresponding slip ring reaches the end of the corresponding array of suction ports 5122 in the conduit, and the adhesive attraction between the discrete parts 532 and the web 121 causes the discrete parts to transfer to the combined web 121.

The noncircular gears then cause a decrease in the radial velocity of the corresponding transport head such that, by the time the transport head returns to the taking zone 5164 and to receive another portion of the incoming web 5170, the surface speed of the transport head matches the surface speed of the incoming webs 5170. As the transport head again picks up a portion of the incoming web 5170, the corresponding slip ring 5118 reaches the beginning of the corresponding array of suction ports 5122 in the conduit, thereby activating suction on the corresponding transport head, to begin another cycle.

As used herein, "transverse" direction, when referring to rotation of the discrete parts means anything not aligned with the first direction of travel of the receiving web 536 as shown in FIG. 36 or the combined web 121, and not 180° from the first direction.

THE SIDE SEAM BONDER

The methods and apparatus contemplated with respect to the side seam bonder 168 as shown in FIG. 13 relates to forming the side seams 30, 36 in the garment 25, the side seams 30, 36 being shown in FIG. 5. Given that the workpiece 319 as shown in FIG. 20 is oriented in the web 121 transverse to the with machine direction of the web, to the extent the side seams are to be formed while the workpiece, or blank, remains part of the web, the side seams 30, 36 will necessarily be formed in an orientation transverse to the with machine direction of the web.

In forming such transverse seals, or welds, using known technology, it is difficult to obtain uniform application of ultrasonic energy across the entire width of the web, whereby the welds may exhibit less than the desired uniformity. The apparatus and methods disclosed hereinafter provide a novel approach to achieving predictably uniform such side welds in the garments being formed.

FIGS. 48–52 illustrate one embodiment of an ultrasonic system of the invention. As seen there, an ultrasonic bonder system 168 includes a work drum 626 mounted on an outer shaft 625, for rotation about an axis 628 passing through a fixed inner shaft generally designated as 630. The work drum 626 has an outer working surface 632 perforated and otherwise adapted in conventional manner (not shown) to provide suction through the outer working surface of the work drum 626, to hold the combined web 121 of material workpieces which, when all processing is finished at side seam bonder 168, are severed from the web, thus providing individual units of garments 25 as the finished product.

Referring, now to the drawings, a plurality of anvil bars 634 (six are shown) are mounted to the work drum, spaced uniformly about the outer circumference of the work drum, and extend transversely across the width dimension of the outer working surface of the work drum 626. The anvil bars are generally flush with the outer working surface 632, such that outer surfaces 636 of the anvil bars 634 generally comprise a continuation of the outer working surface 632 of the work drum 626. Minor offsets of the anvil bars 634 from the outer working surface 632 are acceptable so long as the web can be processed as disclosed herein with respect to the overlying rotary horn or wheel disclosed in more detail hereinafter.

Figure 48:
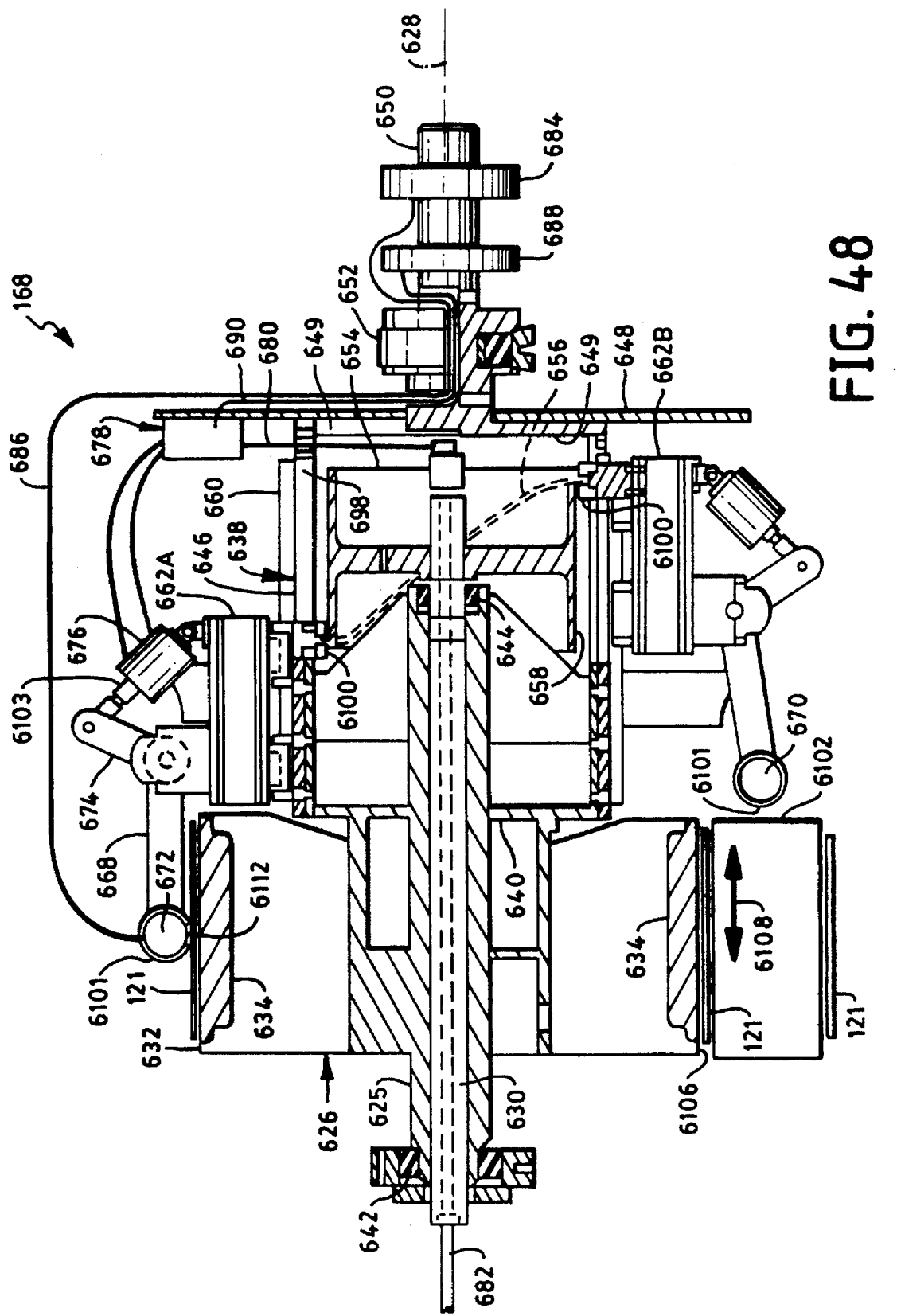
FIG. 48 is a cross-section of the side seam bonder of FIG. 17, taken at 49—49 of FIG. 17.

A support drum 638 is secured to the work drum 626, and mounted for rotation with the work drum. Referring to FIG. 48, support drum 638 is secured to work drum 626 at interface wall 640. The combination of the work drum 626 and the support drum 638 are mounted to the outer shaft 625. Outer shaft 625 is mounted to the fixed inner shaft 630 by bearings 642 and 644. An outer wall 646 of the support drum 638 is secured to end flange 648 through end wall 649. End flange 648 is secured to driven shaft 650 which is driven off the line shaft, not shown, of the processing line. Driven shaft 650 is mounted to ground through bearing 652. Accordingly, the work drum 626, the support drum 638, and the end flange 648 are all supported by the combination of bearings 642, 644, and 652, and all rotate in unison about fixed inner shaft 630 and the axis 628.

Figure 17:
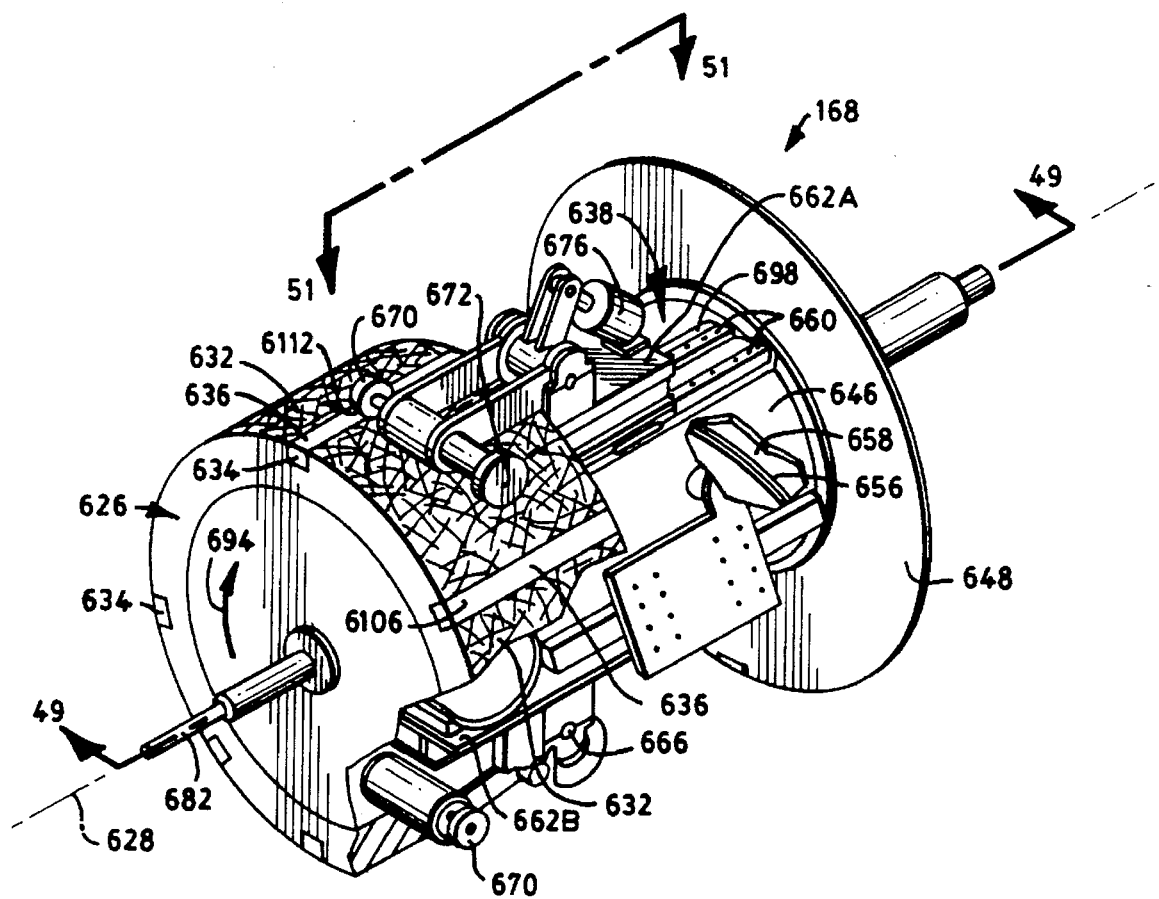
FIG. 17 is a pictorial view, with parts missing and parts cut away, showing a side seam bonder useful in the invention.

Cam drum 654 is fixedly secured to fixed inner shaft 630, such that it does not rotate with the combination of work drum 626, support drum 638, and end flange 648. Cam rib 656 is mounted on the outer wall 658 of the cam drum 654, and extends about the entire circumference of the outer wall 658 of the cam drum. Cam rib 656 is seen in dashed outline in FIGS. 49 and 53. A portion of the cam rib is seen through a cutaway portion of the outer wall 646 of the support drum in FIG. 17.

Figure 51:
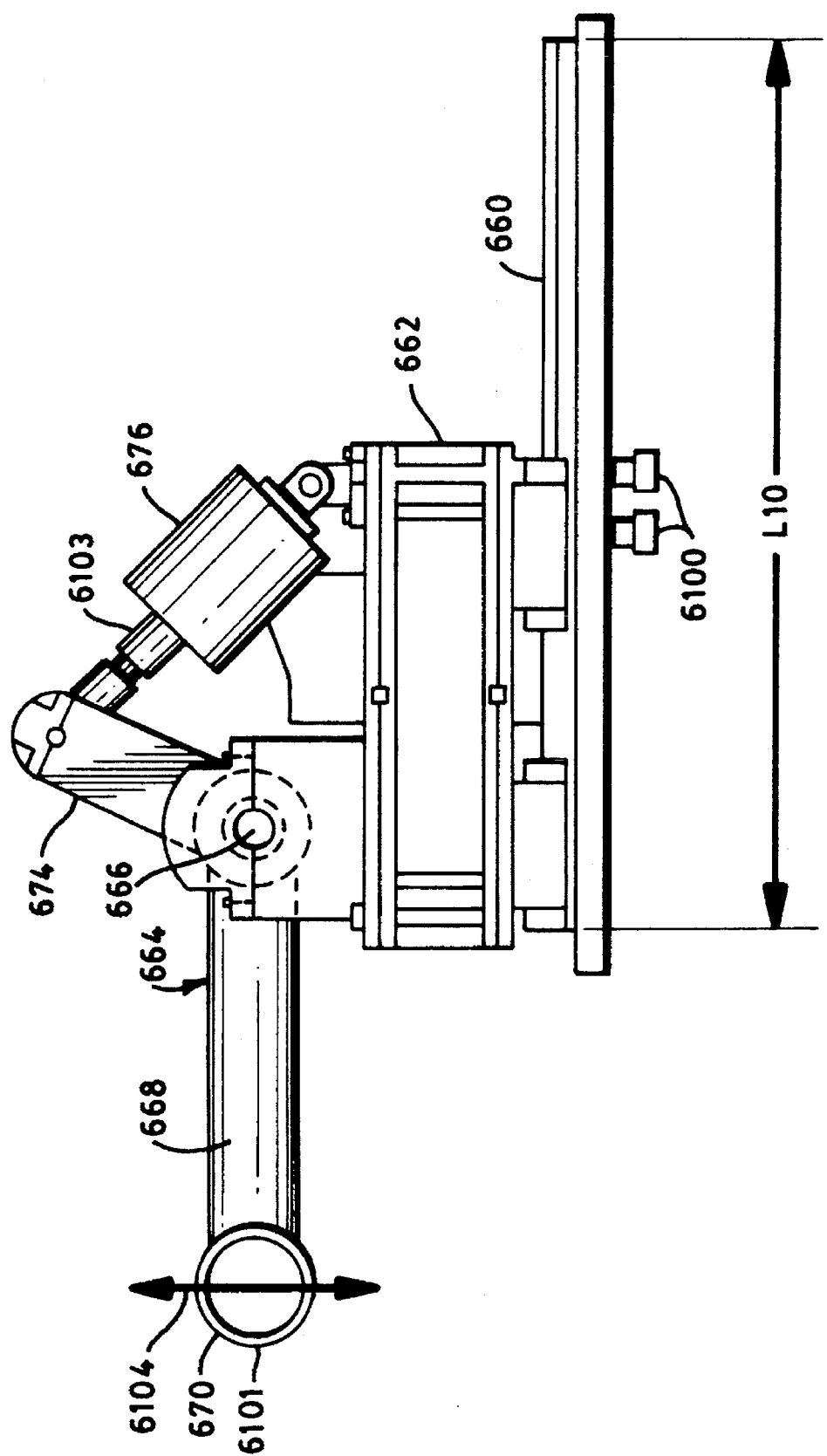
FIG. 51 is a side view of the first energy application device of FIG. 50.
Figure 52:
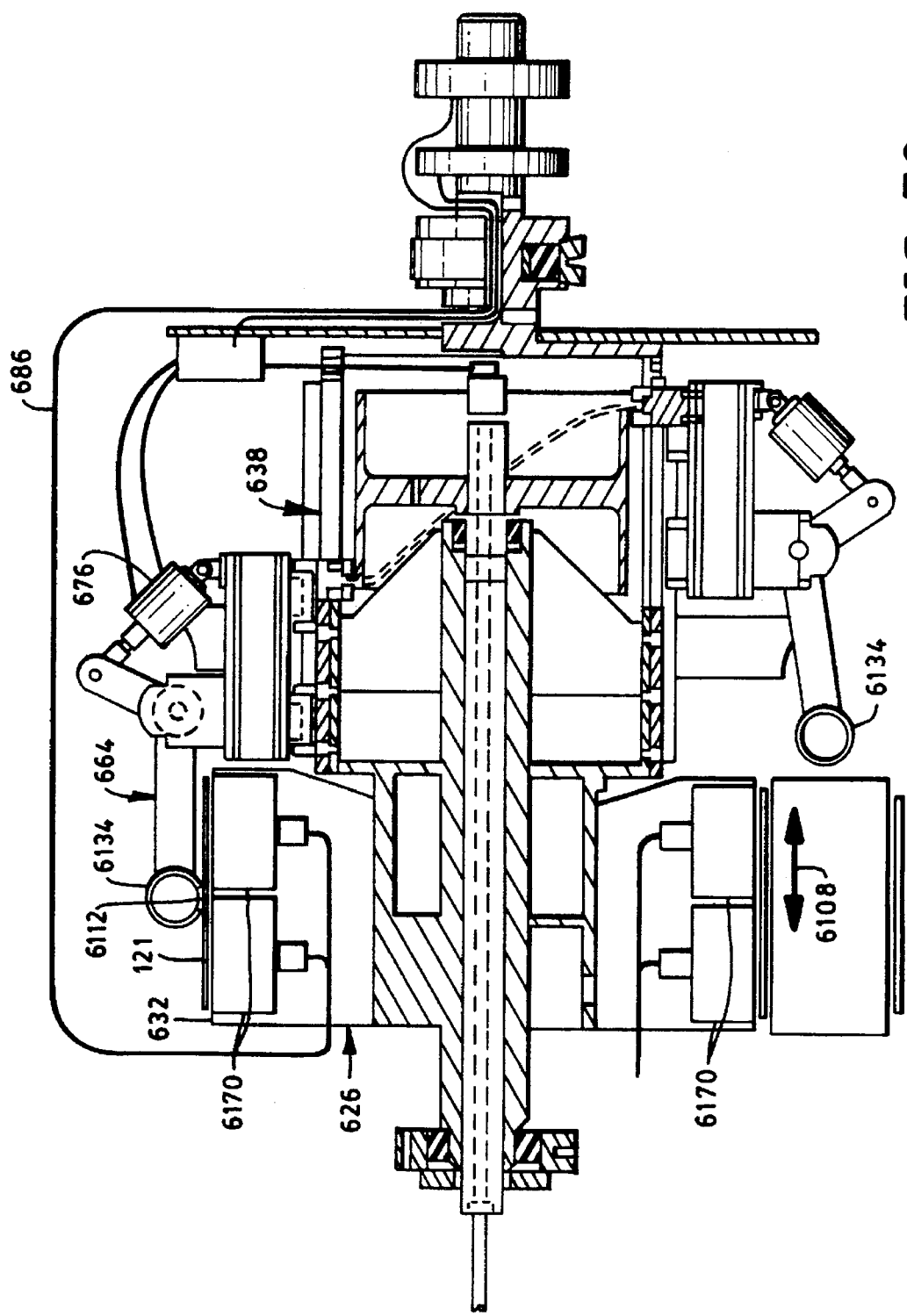
FIG. 52 is a cross-section as in FIG. 48, of a second embodiment of a side seam bonder useful in the invention.

Referring to FIGS. 51 and 52, six pairs of carriage support tracks 660 are secured to the outer wall 658 of cam drum 654, corresponding in number, and in general location, to respective anvil bars 634 on the outer working surface 632 of work drum 626. A carriage 662 is mounted to each pair of carriage support tracks 660, for sliding engagement with the carriage support tracks, along the lengths "L10" of the respective carriage support tracks, as will be illustrated further hereinafter.

Referring now to FIGS. 51 and 52, an ultrasonic support subassembly 664 is mounted to each carriage 662 at pivot pin 666. In the ultrasonic support subassembly 664, support arm 668 extends from pivot pin 666, toward outer working surface 632 of the work drum 626, and supports, at its remote end, a rotary ultrasonic horn 670 and ultrasonic generator 672. Support arm 668 is fixedly secured to control arm 674. Control arm 674 is operated by double acting air cylinder 676, acting through pivot pin 666 and control arm 674, to pivot the ultrasonic horn 670 about pivot pin 666 and thereby to raise and lower the ultrasonic horn 670 with respect to the outer working surface 632 of work drum 626. Thus, the ultrasonic support subassembly 664 comprises pivot pin 666, support arm 668, and control arm 674.

Compressed air is supplied to the air cylinder 676 from pneumatic control box 678 as shown in FIG. 48. Compressed air is supplied to the pneumatic control box 678 through air supply line 680, which is connected, through a conventional rotary pneumatic coupling to fixed shaft 630. Air is supplied through the center of fixed shaft 630 from a supply line 682.

Electric power is supplied to the ultrasonic bonder system 168 through slip rings 684, and is communicated to the ultrasonic generators through supply line 686.

Programmable limit switch 688 is also mounted to the driven shaft 650, for purpose to be discussed hereinafter. Output of the programmable limit switch 688 is fed to the control box 678 through electric line 690.

It is contemplated that the operation and functions of the side seam bonder system 168 have become fully apparent from the foregoing description of elements and their relationships with each other, but for completeness of disclosure, the usage of the side seam bonder will be briefly described.

Figure 49:
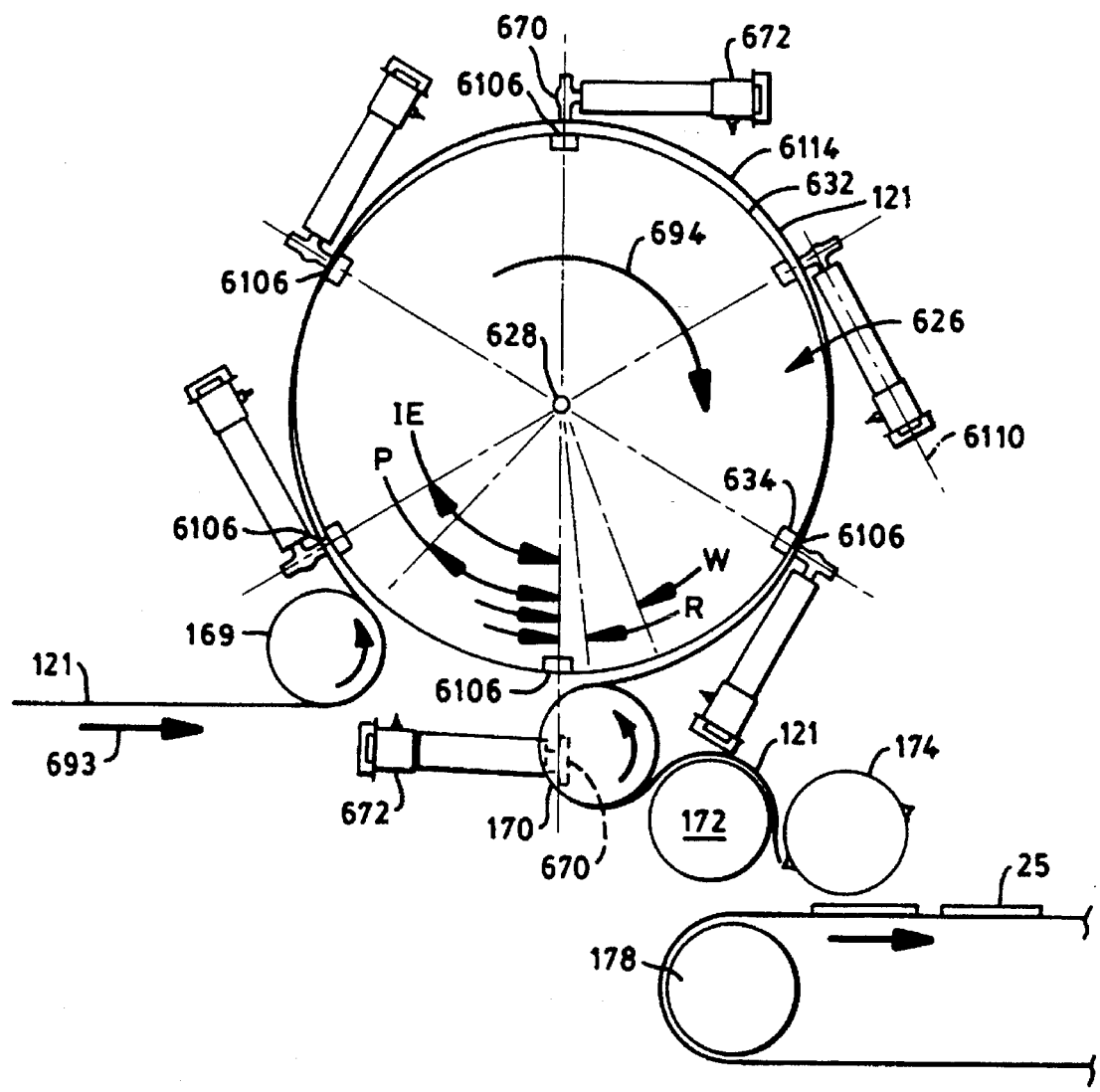
FIG. 49 is a schematic representation of an end elevation view of the side seam bonder of FIG. 17.

Turning now to FIG. 48, driven shaft 650 turns end flange 648, work drum 626, support drum 638 and its supported carriages 662, ultrasonic support subassemblies 664, ultrasonic horns 670, and generators 672, continuously at a steady speed of rotation. Referring to FIG. 49, an incoming turning roll 169 is disposed at a placing station, relative to a reference line through axis 628, at an angle "P" on the circumference of the work drum 626. Combined web 121 of workpieces 319 is fed, in the direction indicated by arrow 693 about incoming turning roll 169, and is thereby drawn into engagement with the working surface 632 of the work drum 626, at the nip formed between work drum 626 and turning roll 169, while the work drum is rotating in the direction indicated by the arrow 694. The web 121 is generally drawn about the circumference of work drum 626 at its outer working surface from incoming turning roll 169 until it reaches the outgoing turning roll 170, at the removing station disposed at an angle "R" on the circumference of the work drum. At outgoing turning roll 170, the web 121 turns about the turning roll 170 as indicated there by the web 121.

In general, as the invention is practiced, the ultrasonic horns are continuously activated, resonating at their designed frequencies.

Turning to the combination of FIGS. 48–52, a slot opening 698 extends through the outer wall 646 of support drum 638 adjacent each carriage support track 660. A pair of cam followers 6100 extends downwardly from each respective carriage, through slot opening 698, and engages the rib cam 656. Accordingly, as the working drum and support drum rotate on axis 628, about the stationary cam drum 654, the engagement of the cam followers 6100 with the rib cam 656 causes the carriages 662 to move alternately toward and away from the outer working surface 632 of the work drum 626. Each carriage thus makes one complete round trip motion, toward the work drum and away from the work drum, for each 360 degree rotation of the work drum. Accordingly, and now referring to FIGS. 48–50, the carriage 662A at the 12 o'clock position on support drum 638 is fully extended toward the work drum; and the carriage 662B at the 6 o'clock position on support drum 638 is fully withdrawn away from the work drum.

As the carriages extend toward the work drum 626, the respective ultrasonic horns extend over the outer working surface 632 of the work drum, and over the corresponding anvil bar 634. As the carriages withdraw from the work drum, the respective ultrasonic horns withdraw from over the outer working surface of the work drum.

An ultrasonic horn is considered fully withdrawn from over the outer working surface 632 when the remote outer edge 6101 as shown in FIG. 51 of the combination of the ultrasonic support assembly 664, horn 670, and generator 672, passes inwardly of the inner edges 6102 as shown in FIG. 48 of turning rolls 169 and 170. See FIG. 48, where the horn on carriage 662B is fully withdrawn, and has moved still further away from the work drum than the defined "fully withdrawn" position. Accordingly, "fully withdrawn" comprehends a range of positions of the outer edge 6101 disposed inwardly of the inner edges 6102 of the turning rolls 169 and 170, and is not limited to the innermost position where the carriage 662 is disposed in its most remote position with respect to the work drum.

As each carriage 662 extends toward the work drum, and the respective ultrasonic horn 670 is correspondingly disposed over the outer working surface 632, programmable limit switch 688 signals the pneumatic control box 678, thus activating and extending the ram 6103 on the respective air cylinder 676 to thus move the respective resonating ultrasonic horn 670 downwardly, as shown by the double headed arrow indicated as 6104 in FIG. 51, and into contact with the workpiece being carried in the web 121 at the respective work station 6106 defined at each respective anvil bar 634. The rotary ultrasonic horn 670 exerts a downward force on the workpiece against the supporting resistance of the anvil bar. The amount of downward force is controlled by the force exerted at air cylinder 676.

With the resonating rotary ultrasonic horn thus exerting a downward force on the workpiece, the circular rotary horn 670 rotates about an axis 6110 as it provides an effective application of ultrasonic energy to the workpiece at a limited area of contact 6112 between the ultrasonic horn and the web 121 as supported by anvil 634. The limited area of contact 6112 moves progressively across the workpiece as the ultrasonic horn traverses across the working surface in an energy application path 6108.

Figure 50:
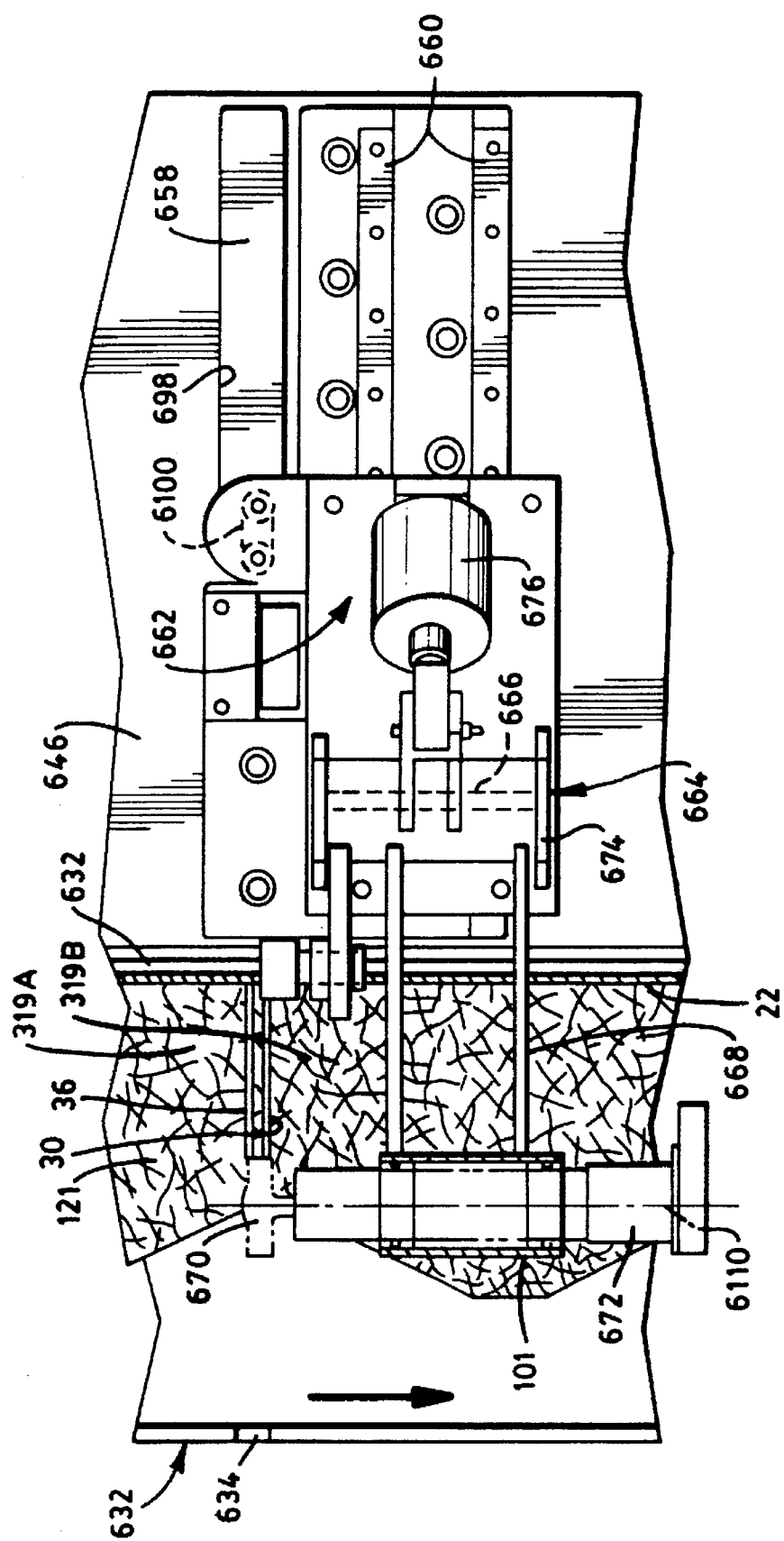
FIG. 50 is a top view of the first energy application device with a web of workpieces thereon, taken at 51—51 of FIG. 17.

As the horn moves progressively across the working surface, applying ultrasonic energy to the limited area of contact 6112, it simultaneously and progressively forms the side seam bonds 30, 36 on the trailing edge of a leading workpiece 319 and on the leading edge of the next trailing workpiece 319, as indicated in FIG. 50. The particular pattern, if any, in the bond formed is controlled by the surface pattern, if any, on the ultrasonic horn or the anvil, preferably on the anvil 634.

As indicated in FIG. 48, the energy application path can extend less than all the way across the working surface of the drum 626; or can extend less than all the way across the web, depending on what work is to be performed by the ultrasonic energy, and the lengths of carriage support tracks 660 and support arm 668.

Preferably, the ultrasonic horn 670 is forced downwardly into working contact with the workpiece while the horn is traversing the outgoing segment of the energy application path. When the respective ultrasonic horn reaches the outer extremity of the outgoing segment of the energy application path, limit switch 688 senses the respective associated angular position of the working station with respect to axis 628, and signals the pneumatic control box 678, lifting the horn from the workpiece as the horn is being withdrawn from over the workpiece on the (reverse direction) incoming segment of the energy application path. Referring to FIG. 49, the horn begins being extended over the drum, namely crossing the inner edge 6102 of the turning rolls 169, 170 at an angle "IE" on the outer circumference of the work drum, and is fully withdrawn from over the outer working surface at an angle "W" on the outer circumference of the work drum. Referring to FIG. 49, it is seen that the respective horn assembly is fully withdrawn before the respective workpiece 319 in web 121 arrives at the turning roll 170 where the web and corresponding workpiece are removed from the work drum 626. Similarly, the horn assembly, comprising horn 670, generator 672, and ultrasonic support subassembly 664, remains fully withdrawn, and does not begin being extended over the outer working surface 632 until the horn assembly has passed the incoming turning roll 169 and the outer working surface is again becoming engaged with the incoming web of workpieces.

The working drum 626 thus rotates continuously, accompanied by the ultrasonic horns 670. Workpieces enter the ultrasonic bonder system 168 as they are placed on the work drum 626 as part of web 121, and traverse the working path 6114 between the placing station at angle "P" and the removing station at an angle "R," while the ultrasonic application devices, as horns 670 and anvils 634, form the side seams 30, 36. Each horn thus extends across the outer working surface at the respective anvil to make a set of side seam bonds 30, 36 in a pair of respective workpieces 319A and 319B with each rotation of the work drum. The side seam bonds 30, 36 extend in the cross machine direction. At any given time, the combined apparatus can support performing welding, cutting, like operations or combinations of such operations on substantially as many workpieces as there are work stations 6106, and corresponding workpieces, on the drum between the turning rolls 169 and 170, allowing sufficient clearance for "full withdrawal" of the respective horns from the outer working surface so that the web with the finished workpieces can be removed at turning roll 170.

Suitable rotary ultrasonic horns 670 are, for example, those taught in U.S. Pat. No. 5,110,403 to Ehlert, herein incorporated by reference for its teaching with respect to suitable such rotary ultrasonic horns. Suitable ultrasonic generators, and other related ultrasonic equipment, is available from a variety of suppliers, for example, Branson Sonic Power Company, Danbury, Conn.

While the side seam bonder has been described as preferably using ultrasonic energy, other forms of energy can be applied as well, for example thermal energy, whereby the rotary horn 670 is replaced with a heated wheel, or the like.

Referring to FIG. 49, after the side seam bonds 30, 36 have been completed in the workpiece, the workpiece, still in the web 121, passes over turning roll 170, thence to turning roll 172, and then to cutter roll 174, where the workpieces are severed from the web at loci between the adjacent side seam bonds 30, 36 formed by a respective ultrasonic horn 670. The severed workpieces are the garments 25, and are taken away on conveyor 178.

FIG. 52 shows a second embodiment of the invention wherein the ultrasonic horn and the cooperating anvil are disposed in physically reversed locations from the embodiment of FIGS. 48–52. Thus, comparing the embodiment of FIG. 52 to the embodiment described in more detail with respect to FIGS. 48–52, in FIG. 52, a pair of conventional planar-type ultrasonic horns 6170 are mounted in the work drum 626 in place of the anvil bar 634. As many planar type horns can be used as necessary to span the full width of the energy application path. Correspondingly, a rotary anvil 6134 is mounted to the ultrasonic support assembly 664 in place of the rotary ultrasonic horn 670.

In use, the ultrasonic horns 6170 are preferably activated continuously during operation of the process. Work drum 626 and support drum 638 rotate continuously as described above. As the drums rotate, the rotary anvil is extended over the working surface, and forced into working contact with the workpieces by air cylinder 676 as the anvil traverses the outgoing segment of the energy application path 6108, and lifts the anvil from the workpiece as it traverses the incoming segment of the energy application path. The significant difference is that the locations of the ultrasonic horn and the anvil are reversed, while the physical movement role of extending over the outer working surface and subsequently withdrawing remains embodied in the elements mounted on carriage 662. Accordingly, the ultrasonic application device mounted in the outer working surface of the work drum is the device supplying the ultrasonic energy, rather than the ultrasonic application device mounted on the ultrasonic support subassembly 664.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. A method for use in constructing a garment including elastic, in a processing system, as one of a series of consecutive workpieces in a continuous web, each workpiece having front and back body portions, separated by a crotch portion, the workpiece being disposed in a transverse orientation in the web, with the front and back body portions on opposing sides of the web, the method including, with respect to respective workpieces, the steps of:

(a) stretching an elastic;
    (b) incorporating the stretched elastic into the continuous web in stretched condition;
    (c) subsequently relieving stretch in the elastic at the crotch portion of each respective workpiece in the web, while maintaining the stretch in the elastic at the front and back body portions of each respective workpiece;
    (d) folding the web such that the front and back body portions of each respective workpiece are in face-to-face relationship with each other;
    (e) forming side seam bonds, thereby joining the front body portion to the back body portion, in the web, and thereby effectively joining the respective first and second leg elastics at the side seam bonds; and
    (f) after forming the side seam bonds, severing the respective workpiece from the web and thereby obtaining the garment.

2. A method as in claim 1, the relieving of stretch comprising severing the elastic at the crotch portion without adversely affecting the continuous web.

3. A method as in claim 1, the relieving of stretch including applying ultrasonic energy to an outer surface of the workpiece at at least one selected locus at the crotch portion, sufficient to effect severing of the elastic without corresponding severing of the continuous web.

4. A method as in claim 1, the elastic comprising elastic elements, each elastic element including at least one thread of elastic disposed on the interior of the workpiece, the relieving of stretch including applying ultrasonic energy to the outer surface of the workpiece at at least one selected locus at the crotch portion, sufficient to effect severing of at least one of the threads of elastic on the interior of the workpiece without corresponding severing of the continuous web.

5. A method as in claim 1, including relieving substantially all the stretch in the elastic at the crotch portion while maintaining substantially all the stretch in the elastic at the front and back body portions.

6. A method as in claim 1, the method being adapted to process a garment having first and second leg openings on opposing sides of the crotch portion, the elastic comprising (i) a first leg elastic extending along a first front edge of the first leg opening, across the crotch portion, and along a second front edge of the second leg opening, and (ii) a second leg elastic extending along a first back edge of the second leg opening, across the crotch portion, and along a second back edge of the second leg opening.

7. A method as in claim 1, the method being adapted to process a garment having first and second leg openings on opposing sides of the crotch, the elastic comprising a second leg elastic extending along a first back edge of the second leg opening, across the crotch portion, and along a second back edge of the second leg opening.

8. A method as in claim 6, including stretching third leg elastic, orienting the third leg elastic in a direction essentially transverse to the longitudinal dimension of the web, and incorporating the transverse, stretched third leg elastic along opposing edges of the crotch portion, with opposing portions of the third leg elastic being disposed adjacent respective ones of the first and second leg elastics.

9. A method as in claim 6, the web having a width dimension, the method including incorporating the first and second leg elastics into the continuous web on a first rotary transport device having a first outer working surface including a first set of protuberances thereon, interacting with the web and thereby inhibiting shrinkage of the web in the width dimension on the first rotary transport device, transferring the web from the first rotary transport device to a second outer working surface of a second rotary transport device, the first and second outer working surfaces being aligned with each other at the locus of closest approach of the first and second outer working surfaces, the second outer working surface including a second set of protuberances thereon, the second set of protuberances being aligned with the first set of protuberances along the direction of advance of the web, and interacting with the web and thereby inhibiting shrinkage of the web in the width dimension on the second rotary transport device.

10. A method as in claim 9, including aligning the first and second outer working surfaces at the locus of closest approach of the first and second outer working surfaces, across the entire width of the web, and maintaining such alignment while transferring the web from the first rotary transport device to the second rotary transport device.

11. A method as in claim 9, including applying suction to the web at least one of the first and second outer working surfaces, to assist in inhibiting shrinkage of the web in the width dimension.

12. A method as in claim 9, the first rotary transport device comprising a substrate comprising a support for the first outer working surface, and a coating on the substrate, incorporating the first set of protuberances, and including a release agent in the composition of the coating.

13. A method as in claim 9, the method being effective to retain the width of the web dimensionally stable such that shrinkage in the width dimension, between first and second edges of the web, is no more than about 5%.

14. A method as in claim 1, the relieving of stretch comprising severing the elastic at the crotch portion and correspondingly cutting the continuous web.

15. A method as in claim 1, the forming of the side seam bonds including the steps of rotating a drum about a first axis in a given direction, the drum having a circumferential outer working surface, a first energy application device mounted on the drum adjacent the outer working surface and extending transverse to the direction of rotation of the drum; providing a second energy application device, mounted for rotation with the drum; moving the second energy application device in a direction transverse to the direction of rotation of the drum and thereby extending the second energy application device over the first energy application device and operating the first and second energy application devices in combination and thereby applying energy to the workpiece during rotation of the drum; and withdrawing the second energy application device from over the first energy application device during rotation of the drum.

16. A method as in claim 15, including traversing the second energy application device along an energy application path over the first energy application device, the first energy application device comprising an anvil, the second energy application device comprising a wheel mounted for rotation about a second axis, the method comprising applying energy to the workpiece at a locus moving progressively across the workpiece as the wheel traverses the energy application path.

17. A method as in claim 15, including using an ultrasonic horn as one of the first and second energy application devices, and using an anvil adapted to cooperate with the ultrasonic horn as the other of the energy application devices.

18. A method as in claim 15, including traversing the second energy application device along an energy application path over the first energy application device, the first energy application device comprising an anvil, the second energy application device comprising a rotary ultrasonic horn mounted for rotation about a second axis, the method comprising applying energy to the workpiece at a point moving progressively across the workpiece as the rotary ultrasonic horn traverses the energy application path.

19. A method for use in constructing a garment including elastic, in a processing system, as one of a series of consecutive workpieces in a continuous web, each respective workpiece having front and back body portions, separated by a crotch portion, the method including, with respect to respective workpieces, the steps of:

(a) stretching first and second leg elastics;

(b) incorporating the first and second stretched leg elastics into the continuous web in stretched condition; and (c) stretching third leg elastic, orienting the third leg elastic in a direction transverse to the longitudinal dimension of the web, and, while maintaining the stretched third leg elastic in the transverse orientation, incorporating the stretched third leg elastic along opposing edges of the crotch portion such that opposing portions of the third leg elastic are disposed on opposing sides of the crotch adjacent respective ones of the first and second leg elastics, to thereby provide effective continuity of stretching capacity at the respective leg openings between the third leg elastic and respective ones of the first and second leg elastics.

20. A method as in claim 19, including the steps of (d) folding the continuous web such that the front and back body portions of each respective workpiece are facing each other;

(e) forming side seam bonds and thereby joining the front body portion to the back body portion, in the web, and thereby effectively joining the respective first and second leg elastics at the side seam bonds; and (f) subsequent to forming the side seam bonds, severing the individual workpieces from the web.

21. A method as in claim 19, the method further comprising relieving stretch in the first and second leg elastics at a crotch portion of each respective workpiece in the web, while maintaining the stretch in the first and second leg elastics at the front and back body portions of the respective workpieces.

22. A method as in claim 21, including forming first and second leg openings by cutting away portions of the web, in registration such that the first leg elastic extends along a first front edge of the first leg opening, across the crotch portion, and along a second front edge of the second leg opening, the second leg elastic extending along a first back edge of the second leg opening, across the crotch portion, and along a second back edge of the second leg opening, the method including relieving the stretch in the crotch portion by severing the respective first and second leg elastics.

23. A method as in claim 21, the relieving of stretch comprising severing the first and second leg elastics at the crotch portion without adversely affecting the continuous web.

24. A method as in claim 21, the relieving of stretch including applying ultrasonic energy to the outer surface of the workpiece at at least one selected locus at the crotch portion, sufficient to effect severing of the first and second leg elastics without corresponding severing of the continuous web.

25. A method as in claim 21, each of the first and second leg elastics comprising elastic elements including at least one thread of elastic disposed on the interior of the workpiece, the method including applying ultrasonic energy to the outer surface of the workpiece at at least one selected locus at the crotch portion, to a layer of the workpiece interposed between the at least one thread of elastic and an ultrasonic energy application device, and thereby driving through the layer sufficient energy to effect severing of at least one of the threads of elastic on the interior of the workpiece, without corresponding severing of the continuous web.

26. A method as in claim 21, each of the first and second leg elastics comprising elastic elements including at least one thread of elastic disposed on the interior of the workpiece, the method including applying ultrasonic energy to the outer surface of the workpiece at at least one selected locus at the crotch portion, to a layer of the workpiece interposed between the at least one thread of elastic and an ultrasonic energy application device, and thereby driving through the layer sufficient energy to effect severing of at least one of the threads of elastic on the interior of the workpiece, without corresponding severing of the layer.

27. A method as in claim 21, the relieving of stretch in the first and second leg elastics at the crotch portion comprising applying an active force to a dancer roll, thereby effecting active movement of the dancer roll for each workpiece entering into the processing system, the active movement of the dancer roll being effective to relieve stretch in the first and second leg elastics.

28. A method as in claim 27, including applying the active force to the dancer roll in a first direction, and applying a second active force in a second opposite direction, in cycles, each cycle corresponding to advance of one of the workpieces in the continuous web into the processing system, each of the cycles thus causing movement of the dancer roll, including (i) corresponding relieving of tension in the first and second leg elastics as the first and second leg elastics are incorporated into the web at the crotch portion of the corresponding workpiece, and (ii) imposing of tension as the first and second leg elastics are incorporated into the web at the front and back body portions of the workpiece.

29. A method as in claim 27, including adjusting the value and direction of the active force at least 500 times per second.

30. A method as in claim 28, including adjusting the value and direction of the active force at least 500 times per second.

31. A method as in claim 27, velocity of the dancer roll being effected with a prime mover, the method including measuring a first velocity of the web after the dancer roll, measuring a second velocity of the web at the dancer roll, measuring translational velocity of the dancer roll, sensing the position of the dancer roll, measuring web tension before the dancer roll, measuring web tension after the dancer roll, and controlling the prime mover by using a computer controller providing control commands to the prime mover based at least in part on the sensed position and the above measured tensions and velocities, and thereby controlling the active force imparted to the dancer roll by the prime mover.

32. A method as in claim 19, the web having a width dimension, the method including incorporating the first and second leg elastics into the continuous web on a first rotary transport device having a first outer working surface including a first set of protuberances, interacting with the web and thereby inhibiting shrinkage of the web in the width dimension on the first rotary transport device, transferring the web from the first rotary transport device to a second outer working surface of a second rotary transport device, the second outer working surface including a second set of protuberances, the first and second outer working surfaces being aligned with each other at a locus of closest approach of the first and second outer working surfaces, the second set of protuberances being aligned with the first set of protuberances along the direction of advance of the web, and interacting with the web and thereby inhibiting shrinkage of the web in the width dimension on the second rotary transport device.

33. A method as in claim 32, the first set of protuberances being aligned with the second set of protuberances along the direction of advance of the web.

34. A method as in claim 32, including applying suction to the web at at least one of the first and second outer working surfaces, to assist in inhibiting shrinkage of the web in the width dimension.

35. A method as in claim 32, the first rotary transport device comprising a substrate comprising a support for the first outer working surface, and a coating on the substrate, incorporating the first set of protuberances, and including a release agent in the composition of the coating.

36. A method as in claim 32, the method being effective to retain the width of the web dimensionally stable such that shrinkage in the width dimension, between first and second edges of the web, is no more than about 5%.

37. A method as in claim 19, the relieving of stretch comprising severing the first and second leg elastics at the crotch portion and correspondingly cutting the continuous web.

38. A method as in claim 19, the relieving of stretch comprising severing the first and second leg elastics at the crotch portion without severing the continuous web.

39. A method as in claim 38, and including severing the first and second leg elastics at the crotch portion without effecting corresponding severing of the continuous web, by applying ultrasonic energy to the outer surface of the workpiece at at least one selected locus in the crotch portion, sufficient to effect the severing of the elastics without corresponding severing of the continuous web.

40. A method as in claim 38, the first and second leg elastics comprising threads of elastic disposed on the interior of the workpiece, the method including severing the first and second leg elastics at the crotch portion without effecting corresponding severing of the continuous web, by applying ultrasonic energy to the outer surface of the workpiece at at least one selected locus in the crotch portion over at least one of the first and second leg elastics, sufficient to effect severing of at least one of the threads of elastic without corresponding severing of the continuous web.

41. A method as in claim 19, including relieving substantially all the stretch in the first and second leg elastics across the crotch portion while maintaining substantially all the stretch in the first and second leg elastics along the respective front and back body portions.

42. A method as in claim 20, the forming of the side seam bonds including the steps of rotating a drum about a first axis in a given direction, the drum having a circumferential outer working surface, a first energy application device mounted on the drum adjacent the outer working surface and extending transverse to the direction of rotation of the drum; providing a second energy application device, mounted for rotation with the drum; moving the second energy application device in a direction transverse to the direction of rotation of the drum and thereby extending the second energy application device over the first energy application device and operating the first and second energy application devices in combination and thereby applying energy to the workpiece during rotation of the drum; and withdrawing the second energy application device from over the first energy application device during rotation of the drum.

43. A method as in claim 42, including traversing the second energy application device along an energy application path over the first energy application device, the first energy application device comprising an anvil, the second energy application device comprising a wheel mounted for rotation about a second axis oriented transverse to the first axis, the method comprising applying energy to the workpiece at a locus moving progressively across the workpiece as the wheel traverses the energy application path.

44. A method as in claim 42, including using an ultrasonic horn as one of the first and second energy application devices, and using an anvil adapted to cooperate with the ultrasonic horn as the other of the energy application devices.

45. A method as in claim 42, including traversing the second energy application device along an energy application path over the first energy application device, the first energy application device comprising an anvil, the second energy application device comprising a rotary ultrasonic horn mounted for rotation about a second axis oriented transverse to the first axis, the method comprising applying energy to the workpiece at a point moving progressively across the workpiece as the rotary ultrasonic horn traverses the energy application path.

46. A method for use in constructing a garment including elastic therein, in a processing system, as one of a series of consecutive workpieces in a continuous web having a width dimension, the method including, with respect to respective workpieces, the steps of:
   (a) stretching elastic;
   (b) incorporating the elastic into the continuous web in stretched condition on a first rotary transport device having a first outer working surface effective to inhibit shrinkage of the web in the width dimension on the first rotary transport device without use of suction; and
   (c) relieving stretch in the elastic at a first portion of each respective workpiece in the web, while maintaining stretch in the elastic at a second portion of each respective workpiece.

47. A method as in claim 46, the first outer working surface of the first rotary transport device including a first set of protuberances, interacting with the web and thereby inhibiting shrinkage of the web in the width dimension on the first rotary transport device, the method including transferring the web from the first rotary transport device to a second outer working surface of a second rotary transport device, the first and second outer working surfaces being aligned with each other at a locus of closest approach of the first and second outer working surfaces, the second outer working surface including a second set of protuberances thereon, the second set of protuberances being aligned with the first set of protuberances along the direction of advance of the web, and interacting with the web and thereby inhibiting shrinkage of the web in the width dimension on the second rotary transport device.

48. A method as in claim 47, including aligning the first and second outer working surfaces at the locus of closest approach of the first and second outer working surfaces, across the entire width of the web, and maintaining such alignment while transferring the web from the first rotary transport device to the second rotary transport device.

49. A method as in claim 46, the first rotary transport device comprising a substrate, the substrate comprising a support for the first outer working surface, the first outer working surface being comprised in a coating on the substrate, the coating incorporating the first set of protuberances, and including a release agent in the composition thereof.

50. A method as in claim 46, the method being effective to retain the width of the web dimensionally stable such that shrinkage in the width dimension, between first and second edges of the web, is no more than about 5%.

51. A method as in claim 46, the relieving of stretch comprising severing the elastic at the first portion without adversely affecting the continuous web.

52. A method as in claim 46, the relieving of stretch comprising applying ultrasonic energy to the outer surface of the workpiece at at least one selected locus at the first portion, sufficient to effect severing of the elastic without corresponding severing of the continuous web.

53. A method as in claim 46, the elastic comprising elastic elements including at least one thread of elastic disposed on the interior of the workpiece, the relieving of stretch comprising applying ultrasonic energy to the outer surface of the workpiece at at least one selected locus at the first portion, sufficient to effect severing of at least one of the threads of elastic on the interior of the workpiece without corresponding severing of the continuous web.

54. A method as in claim 46, including relieving substantially all the stretch in the elastic at the first portion while maintaining substantially all the stretch in the elastic at the second portion.

55. A method for use in constructing a garment including elastic therein, in a processing system, as one of a series of consecutive workpieces in a continuous web, the method including, with respect to respective workpieces, the steps of:
   (a) stretching a continuous elastic;
   (b) incorporating the stretched continuous elastic into the continuous web; and
   (c) relieving stretch in the elastic at a first portion of each respective workpiece in the web, the relieving of stretch comprising using a dancer roll to control tension in the continuous elastic as the continuous elastic is being incorporated into the continuous web, including applying a first active force to the dancer roll in a first direction, and a second active force in a second opposite direction, in cycles, each cycle corresponding to the advance of one of the workpieces in the continuous web into the processing system, each cycle thus causing movement of the dancer roll, including (i) corresponding relieving of tension in the continuous elastic as the continuous elastic is incorporated into the web at the first portion of the corresponding workpiece, and (ii) imposing of tension as the continuous elastic is incorporated into the web at a second portion of the workpiece.

56. A method as in claim 55, velocity of the dancer roll being effected with a prime mover, the method including measuring a first velocity of the web after the dancer roll, measuring a second velocity of the web at the dancer roll, measuring translational velocity of the dancer roll, sensing the position of the dancer roll, measuring web tension before the dancer roll, measuring web tension after the dancer roll, and controlling the prime mover with a computer controller providing control commands to the prime mover based at least in part on the sensed position and the above measured tensions and velocities, and thereby controlling the active force imparted to the dancer roll by the prime mover.

57. A method as in claim 55, including adjusting the value and direction of the active force at least 500 times per second.

58. A method as in claim 56, including adjusting the value and direction of the active force at least 500 times per second.

59. A method as in claim 55, the relieving of stretch comprising severing the elastic at the first portion without adversely affecting the continuous web.

60. A method as in claim 55, the relieving of stretch comprising applying ultrasonic energy to the outer surface of the workpiece at at least one selected locus at the first portion, sufficient to effect severing of the elastic without corresponding severing of the continuous web.

61. A method as in claim 55, the elastic comprising elastic elements including at least one thread of elastic disposed on the interior of the workpiece, the relieving of stretch comprising applying ultrasonic energy to the outer surface of the workpiece at at least one selected locus at the first portion, sufficient to effect severing of at least one of the threads of elastic on the interior of the workpiece without corresponding severing of the continuous web.

62. A method as in claim 55, the method being adapted to process a garment having front and back body portions, and an intervening crotch, and first and second leg openings on opposing sides of the crotch, the continuous elastic comprising (i) a first leg elastic extending along a first front edge of the first leg opening, across the crotch, and along a second front edge of the second leg opening, and (ii) a second leg elastic extending along a first back edge of the second leg opening, across the crotch, and along a second back edge of the second leg opening, the first portion of the workpiece comprising the crotch, the first and second front edges of the first and second leg openings and the first and second back edges of the first and second leg openings, in combination, comprising the second portion of the workpiece.

63. A method as in claim 62, the workpiece being disposed in a transverse orientation in the web, with the front and back body portions of the workpiece being on opposing sides of the web, the method including folding the web such that the front and back body portions of each respective workpiece are facing each other, and forming side seam bonds joining the front body portion to the back body portion in the web, and thereby effectively joining the respective first and second leg elastics at the side seam bonds.

64. A method for use in constructing a garment including elastic, in a processing system, as one of a series of consecutive workpieces in a continuous web, the workpieces having front and back body portions separated by a crotch portion, the method including, with respect to respective workpieces, the steps of:

(a) stretching an elastic;

(b) incorporating the stretched elastic into the continuous web in stretched condition; and (c) subsequently relieving stretch in the elastic at the crotch portion of each respective workpiece in the web, while maintaining the stretch in the elastic at the front and back body portions of each respective workpiece, by applying ultrasonic energy to the outer surface of the workpiece at at least one selected locus at the crotch portion, sufficient to effect severing of the elastic without corresponding severing of the continuous web.

65. A method as in claim 64, the elastic comprising (i) a first leg elastic extending along a first front edge of the first leg opening, across the crotch portion, and along a second front edge of the second leg opening, and (ii) a second leg elastic extending along a first back edge of the first leg opening, across the crotch portion, and along a second back edge of the second leg opening.

66. A method as in claim 65, including stretching third leg elastic, orienting the third leg elastic in a direction essentially transverse to the longitudinal dimension of the web, and incorporating the transverse, stretched third leg elastic, in the web along opposing edges of the crotch portion, with opposing portions of the third leg elastic being disposed adjacent respective ones of the first and second leg elastics.

67. A method as in claim 64, the web having a width dimension, the method including incorporating the elastic into the continuous web on a first rotary transport device having a first outer working surface including a first set of protuberances thereon, interacting with the web and thereby inhibiting shrinkage of the web in the width dimension on the first rotary transport device, transferring the web from the first rotary transport device to a second outer working surface of a second rotary transport device, the second outer working surface including a second set of protuberances thereon, the second set of protuberances being aligned with the first set of protuberances along the direction of advance of the web, and interacting with the web and thereby inhibiting shrinkage of the web in the width dimension on the second rotary transport device.

68. A method as in claim 67, including applying suction to the web at at least one of the first and second outer working surfaces, to assist in inhibiting shrinkage of the web in the width dimension.

69. A method as in claim 67, the first rotary transport device comprising a substrate comprising a support for the first outer working surface, and a coating on the substrate, incorporating the first set of protuberances, and including a release agent in the composition of the coating.

70. A method as in claim 65, the method being effective to retain the width of the web dimensionally stable such that shrinkage in the width dimension, between first and second edges of the web, is no more than about 5%.

71. A method as in claim 65, the method including folding the web such that the front and back body portions of each respective workpiece are facing each other, and forming side seam bonds joining the front body portion to the back body portion in the web, and thereby effectively joining the respective first and second leg elastics at the side seam bonds.

72. A method as in claim 71, and including, after forming the side seam bonds, severing the respective workpiece from the web as a garment.

\* \* \* \* \*